United States Patent
Satou et al.

(10) Patent No.: US 9,790,427 B2
(45) Date of Patent: *Oct. 17, 2017

(54) LIQUID CRYSTAL COMPOUND HAVING A 3,6-DIHYDRO-2H-PYRAN RING, NEGATIVE DIELECTRIC ANISOTROPY, LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Teizi Satou, Ichihara (JP); Sakura Tachinami, Ichihara (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/015,955

(22) Filed: Feb. 4, 2016

(65) Prior Publication Data

US 2016/0230094 A1 Aug. 11, 2016

(30) Foreign Application Priority Data

Feb. 6, 2015 (JP) ................. 2015-022149

(51) Int. Cl.
| C09K 19/34 | (2006.01) |
| C07D 309/20 | (2006.01) |
| C07D 309/22 | (2006.01) |
| C07D 407/04 | (2006.01) |
| C07F 7/08 | (2006.01) |
| C07D 407/10 | (2006.01) |

(52) U.S. Cl.
CPC ........ *C09K 19/3458* (2013.01); *C07D 309/20* (2013.01); *C07D 309/22* (2013.01); *C07D 407/04* (2013.01); *C07D 407/10* (2013.01); *C07F 7/0896* (2013.01); *C09K 19/3402* (2013.01); *C09K 2019/3422* (2013.01); *C09K 2019/3425* (2013.01)

(58) Field of Classification Search
CPC .............................................. C09K 2019/3422
See application file for complete search history.

(56) References Cited

U.S. PATENT DOCUMENTS

2005/0038267 A1* 2/2005 Poetsch ................. C07C 33/483
549/294
2015/0252264 A1* 9/2015 Goto .................. C09K 19/3402
252/299.61

FOREIGN PATENT DOCUMENTS

| JP | 2004352722 A | 12/2004 |
| JP | 2008545669 A | 12/2008 |
| JP | 2008545671 A | 12/2008 |
| JP | 2009507759 A | 2/2009 |

* cited by examiner

*Primary Examiner* — Chanceity Robinson
(74) *Attorney, Agent, or Firm* — Hogan Lovells US LLP

(57) ABSTRACT

A liquid crystal compound is provided that satisfies at least one physical property, such as high stability to heat and light, a high clearing point (or high maximum temperature), a low minimum temperature of a liquid crystal phase, small viscosity, suitable optical anisotropy, large negative dielectric anisotropy, a suitable elastic constant and good compatibility with other liquid crystal compounds, a liquid crystal composition containing the compound, and a liquid crystal display device including the composition. The liquid crystal compound is represented by formula (1):

in which, $R^a$ and $R^b$ are alkyl having 1 to 10 carbons; ring $A^1$, ring $A^2$ and ring $A^3$ are 1,4-cyclohexylene, 1,4-phenylene; and ring $N^1$ is 2,3-difluoro-1,4-phenylene; G is a divalent group represented by formula (pr-1) or (pr-2);

in which, $Z^1$, $Z^2$, $Z^3$ and $Z^4$ are a single bond; and a, b and c are 0, 1 or 2.

13 Claims, No Drawings

LIQUID CRYSTAL COMPOUND HAVING A 3,6-DIHYDRO-2H-PYRAN RING, NEGATIVE DIELECTRIC ANISOTROPY, LIQUID CRYSTAL COMPOSITION AND LIQUID CRYSTAL DISPLAY DEVICE

TECHNICAL FIELD

The invention relates to a liquid crystal compound, a liquid crystal composition and a liquid crystal display device. More specifically, the invention relates to a liquid crystal compound having a 3,6-dihydro-2H-pyran ring and a negative dielectric anisotropy, a liquid crystal composition containing the compound and a liquid crystal display device including the composition.

BACKGROUND ART

In a liquid crystal display device, a classification based on an operating mode for liquid crystal molecules includes a phase change (PC) mode, a twisted nematic (TN) mode, a super twisted nematic (STN) mode, an electrically controlled birefringence (ECB) mode, an optically compensated bend (OCB) mode, an in-plane switching (IPS) mode, a vertical alignment (VA) mode, a fringe field switching (FFS) mode and a field induced photo-reactive alignment (FPA) mode. A classification based on a driving mode in the device includes a passive matrix (PM) and an active matrix (AM). The PM is classified into static or multiplex and so forth, and the AM is classified into a thin film transistor (TFT), a metal insulator metal (MIM) and so forth.

A liquid crystal composition is sealed into the device. Physical properties of the composition are related to characteristics of the device. Specific examples of the physical properties of the composition include stability to heat and ultraviolet light, a temperature range of a nematic phase, viscosity, optical anisotropy, dielectric anisotropy, specific resistance and an elastic constant. The composition is prepared by mixing many liquid crystal compounds. The physical properties required for the compound include a high stability to an environment such as water, air, heat and light, a wide temperature range of a liquid crystal phase, a small viscosity, a suitable optical anisotropy, a large dielectric anisotropy and a good compatibility with other compounds. The compound having a high maximum temperature of the nematic phase is preferred. The compound having a low minimum temperature of the liquid crystal phase such as the nematic phase or a smectic phase is preferred. The compound having the small viscosity contributes to the device having a short response time. A suitable value of optical anisotropy is different depending on a device mode. The compound having a large positive or negative dielectric anisotropy is preferred for driving the device at low voltage. The compound having the good compatibility with other liquid crystal compounds is preferred for preparing the composition. The device may occasionally be used at a temperature below a freezing point, and therefore the compound having a good compatibility at a low temperature is preferred.

A variety of liquid crystal compounds have so far been prepared. Development of a new liquid crystal compound is continued even now because excellent physical properties that are not found in conventional compounds are expected. The reason is that a suitable balance between two of physical properties required upon preparing the liquid crystal composition is expected for the new compound. Only limited examples of reports are found on the compound having a divalent group described below.

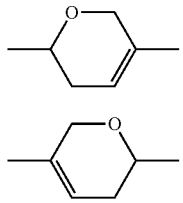

(pr-1)

(pr-2)

JP 2008-545669 A discloses a compound having No. 36 on page 39. The compound is also disclosed on page 41 in JP 2009-507759 A.

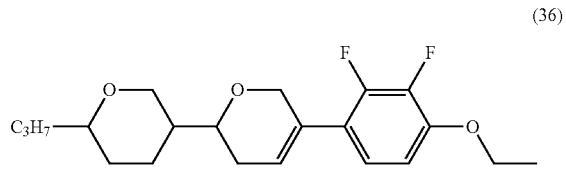

(36)

JP 2008-545671 A discloses a mixture of isomers of 5-(4-ethoxy-2,3-difluorophenyl)-2-pentyldihydro-2H-pyran as a synthetic intermediate on page 18.

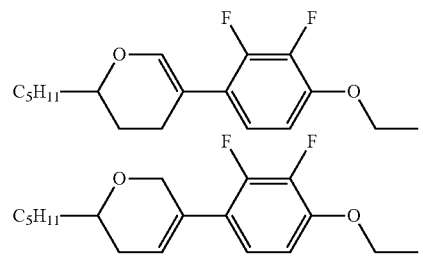

JP 2004-352722 A discloses compound (B1.2 No. 11) on page 100, and compound (B4.1 No. 7) on page 107.

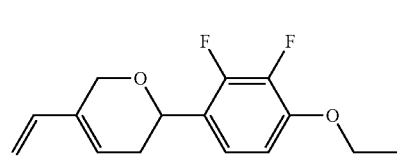

(B1.2 No. 11)

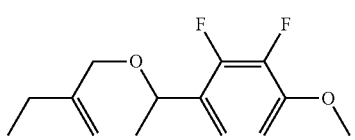

(B4.1 No. 7)

CITATION LIST

Patent Literature

Patent literature No. 1: JP 2008-545669 A
Patent literature No. 2: JP 2009-507759 A
Patent literature No. 3: JP 2008-545671 A
Patent literature No. 4: JP 2004-352722 A

SUMMARY OF INVENTION

Technical Problem

A first object of the invention is to provide a liquid crystal compound satisfying at least one of physical properties such as a high stability to heat and light, a high clearing point (or a high maximum temperature of a nematic phase), a low minimum temperature of a liquid crystal phase, a small viscosity, a suitable optical anisotropy, a large negative dielectric anisotropy, a suitable elastic constant and a good compatibility with other liquid crystal compounds. A second object is to provide a liquid crystal composition containing the compound and satisfying at least one of physical properties such as a high stability to heat and light, a high maximum temperature of a nematic phase, a low minimum temperature of the nematic phase, a small viscosity, a suitable optical anisotropy, a large negative dielectric anisotropy, a large specific resistance and a suitable elastic constant. The object is to provide a liquid crystal composition having a suitable balance regarding at least two of the physical properties. A third object is to provide a liquid crystal display device that includes the composition and has a wide temperature range in which the device can be used, a short response time, a large voltage holding ratio, a low threshold voltage, a large contrast ratio, a small flicker factor and a long service life.

Solution to Problem

The invention concerns a compound represented by formula (1), a liquid crystal composition containing the compound, and a liquid crystal display device including the composition.

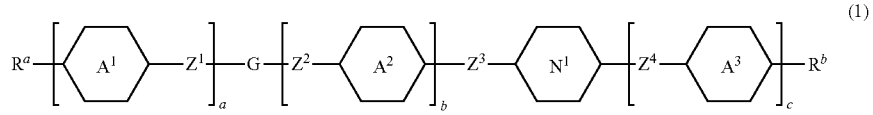

In formula (1), $R^a$ and $R^b$ are independently hydrogen or alkyl having 1 to 10 carbons, and in the alkyl, at least one piece of —$CH_2$— may be replaced by —O—, —S—, —CO— or —$SiH_2$—, at least one piece of —$CH_2CH_2$— may be replaced by —CH=CH— or —C≡C—, and in the groups, at least one piece of hydrogen may be replaced by fluorine or chlorine, and $R^b$ may be fluorine, chlorine, —C≡N or —C≡C—C≡N;

ring $A^1$, ring $A^2$ and ring $A^3$ are independently 1,4-cyclohexylene, decahydronaphthalene-2,6-diyl or 1,4-phenylene, and in the groups, at least one piece of —$CH_2$— may be replaced by —O—, —S—, —CO— or —$SiH_2$—, at least one piece of —$CH_2CH_2$— may be replaced by —CH=CH— or —CH=N—, and in the divalent groups, at least one piece of hydrogen may be replaced by fluorine, chlorine, —C≡N, —$CF_3$, —$CHF_2$, —$CH_2F$, —$OCF_3$, —$OCHF_2$ or —$OCH_2F$;

ring $N^1$ is 1,4-cyclohexylene, decahydronaphthalene-2,6-diyl, 1,2,3,4-tetrahydronaphthalene-2,6-diyl, 2,6,7-trioxabicyclo[2.2.2]octane-1,4-diyl, 1,4-phenylene, naphthalene-2,6-diyl, 9,10-dihydrophenanthrene-2,7-diyl, 9H-xanthene-2,6-diyl or fluorene-2,7-diyl, and in the groups, at least one piece of —$CH_2$— may be replaced by —O—, —S—, —CO— or —$SiH_2$—, at least one piece of —$CH_2CH_2$— may be replaced by —CH=CH— or —CH=N—, and in the divalent groups, at least one piece of hydrogen may be replaced by fluorine, chlorine, —C≡N, —$CF_3$, —$CHF_2$, —$CH_2F$, —$OCF_3$, —$OCHF_2$ or —$OCH_2F$;

G is a divalent group represented by formula (pr-1) or (pr-2);

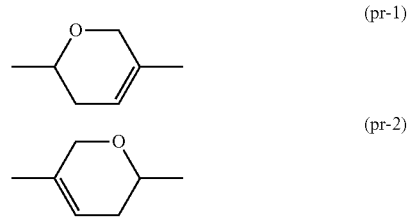

wherein, $Z^1$, $Z^2$, $Z^3$ and $Z^4$ are independently a single bond or alkylene having 1 to 6 carbons, and in the alkylene, at least one piece of —$CH_2$— may be replaced by —O—, —S—, —CO— or —$SiH_2$— one or two pieces of —$CH_2CH_2$— may be replaced by —CH=CH— or —C≡C—, and in the divalent groups, at least one piece of hydrogen may be replaced by fluorine or chlorine;

a, b and c are independently 0, 1 or 2, and a sum of a, b and c is an integer from 0 to 3;

when $R^a$ is —$C_3H_7$, $R^b$ is —$OC_2H_5$, a is 1, b and c are 0, ring $A^1$ is tetrahydropyran-2,5-diyl, $Z^1$ and $Z^3$ are a single bond and ring $N^1$ is 2,3-difluoro-1,4-phenylene, G is a divalent group represented by formula (pr-2); and however, when $R^a$ is —$C_5H_{11}$, $R^b$ is —$OC_2H_5$, a, b and c are 0, $Z^3$ is a single bond and ring $N^1$ is 2,3-difluoro-1,4-phenylene, G is a divalent group represented by formula (pr-2).

However, when $R^a$ is —CH=$CH_2$ or —$C_2H_5$, $R^b$ is —$OC_2H_5$, a, b and c are 0, $Z^3$ is a single bond and ring N is 2,3-difluoro-1,4-phenylene, G is a divalent group represented by formula (pr-1).

Advantageous Effects of Invention

A first advantage of the invention is to provide a liquid crystal compound satisfying at least one of physical properties such as a high stability to heat and light, a high clearing point (or a high maximum temperature of a nematic phase), a low minimum temperature of a liquid crystal phase, a small viscosity, a suitable optical anisotropy, a large negative dielectric anisotropy, a suitable elastic constant, and a good compatibility with other liquid crystal compounds. A second advantage is to provide a liquid crystal composition containing the compound and satisfying at least one of physical properties such as a high stability to heat and light, a high maximum temperature of a nematic phase, a low minimum temperature of the nematic phase, a small viscosity, a suitable optical anisotropy, a large negative dielectric anisotropy, a large specific resistance and a suitable elastic constant. The advantage is to provide a liquid crystal composition having a suitable balance regarding at least two of the physical properties. A third advantage is to provide a liquid crystal display device that includes the composition and has a wide temperature range, a short response time, a large voltage holding ratio, a low threshold voltage, a large contrast ratio, a small flicker factor and a long service life.

DESCRIPTION OF EMBODIMENTS

Usage of terms herein is as described below. Terms "liquid crystal compound," "liquid crystal composition" and "liquid crystal display device" may be occasionally abbreviated as "compound," "composition" and "device," respectively. "Liquid crystal compound" is a generic term for (a) a compound having a liquid crystal phase such as a nematic phase or a smectic phase, and (b) a compound having no liquid crystal phase but being added for the purpose of adjusting physical properties such as a maximum temperature, a minimum temperature, viscosity and dielectric anisotropy. The compound has 1,4-cyclohexylene, 1,4-phenylene and any other six-membered ring, and a rod-like molecular structure. "Liquid crystal display device" is a generic term for a liquid crystal display panel and a liquid crystal display module. "Polymerizable compound" is a compound to be added for the purpose of forming a polymer in the composition.

The liquid crystal composition is prepared by mixing a plurality of liquid crystal compounds. An additive is added to the composition for the purpose of further adjusting the physical properties. The additive such as a polymerizable compound, a polymerization initiator, a polymerization inhibitor, an optically active compound, an antioxidant, an ultraviolet light absorber, a light stabilizer, a heat stabilizer, a dye or an antifoaming agent is added to the liquid crystal composition, when necessary. The liquid crystal compound and the additive are mixed according to such a procedure. A proportion (content) of the liquid crystal compound is expressed in terms of weight percent (% by weight) based on the weight of the liquid crystal composition without containing the additive, even if the composition contains the additive. A proportion (content) of the additive is expressed in terms of weight percent (% by weight) based on the weight of the liquid crystal composition without containing the additive. Weight parts per million (ppm) may be occasionally used. Both proportions of the polymerization initiator and the polymerization inhibitor are exceptionally expressed based on the weight of the polymerizable compound.

"Clearing point" is a transition temperature between the liquid crystal phase and an isotropic phase in the liquid crystal compound. "Minimum temperature of the liquid crystal phase" is a transition temperature between a solid and the liquid crystal phase (the smectic phase, the nematic phase or the like) in the liquid crystal compound. "Higher limit of a temperature range of the nematic phase" is a transition temperature between the nematic phase and the isotropic phase in a mixture of the liquid crystal compound and a base liquid crystal, or in the liquid crystal composition, and may be occasionally abbreviated as "maximum temperature." "Lower limit of the temperature range of the nematic phase" may be occasionally abbreviated as "minimum temperature." An expression "increasing the dielectric anisotropy" means that a value of the dielectric anisotropy positively increases if a composition has a positive dielectric anisotropy, and means that the value of the dielectric anisotropy negatively increases if the composition has a negative dielectric anisotropy. "Having a large voltage holding" means that the device has a large voltage holding ratio at room temperature and also at a temperature close to the maximum temperature in an initial stage, and means that the device has the large voltage holding ratio at room temperature and also at the temperature close to the maximum temperature even after the device has been used for a long period of time. In the composition or the device, characteristics may be occasionally examined before and after a test over time (including an accelerated deterioration test).

A compound represented by formula (1) may be occasionally abbreviated as "compound (1)." At least one compound selected from the group of compounds represented by formula (1) may be occasionally abbreviated as compound (1). "Compound (1)" means a compound represented by formula (1), a mixture of two compounds and a mixture of three or more compounds. A same rule also applies to a compound represented by any other formula. In formula (1) to formula (15), a symbol such as $A^1$, $B^1$ or $C^1$ surrounded by a hexagonal shape corresponds to ring $A^1$, ring $B^1$, ring $C^1$ and so forth, respectively. The hexagonal shape represents a six-membered ring such as cyclohexane and benzene, a condensed ring such as naphthalene, or a bridged ring such as adamantane.

A symbol of terminal group $R^{11}$ is used for a plurality of compounds in chemical formulas of component compounds. In the compounds, two groups represented by two pieces of arbitrary $R^{11}$ may be identical or different. For example, in one case, $R^{11}$ of compound (2) may be ethyl and $R^{11}$ of compound (3) may be ethyl. In another case, $R^{11}$ of compound (2) may be ethyl and $R^{11}$ of compound (3) may be propyl. A same rule also applies to a symbol such as $R^{12}$, $R^{13}$ and $Z^{11}$. In formula (15), when i is 2, two pieces of ring $E^1$ exist. In the compound, two groups represented by two pieces of ring $E^1$ may be identical or different. A same rule also applies to two pieces of arbitrary ring $E^1$ when i is larger than 2. A same rule also applies to any other symbol.

"At least one piece of 'A'" means that the number of 'A' is arbitrary. "At least one piece of 'A' may be replaced by 'B'" means that a position of 'A' is arbitrary when the number of 'A' is 1, and that the positions can be selected within the range of conditions designated therein when the number of 'A' is 2 or more. A same rule also applies to an expression "at least one piece of 'A' is replaced by 'B'." An expression "at least one piece of 'A' may be replaced by 'B' 'C' or 'D'" means a case where arbitrary 'A' is replaced by 'B', a case where arbitrary 'A' is replaced by 'C', and a case where arbitrary 'A' is replaced by 'D', and also a case where a plurality pieces of 'A' are replaced by at least two pieces of 'B', 'C' and/or 'D'. For example, "alkyl in which at least one piece of —$CH_2$— may be replaced by —O— or —CH=CH—" includes alkyl, alkoxy, alkoxyalkyl, alkenyl, alkoxyalkenyl and alkenyloxyalkyl. In addition, a case where replacement of two successive pieces of —$CH_2$— by —O— results informing —O—O— is not preferred. In alkyl or the like, a case where replacement of —$CH_2$— of a methyl part (—$CH_2$—H) by —O— results in forming —O—H is not preferred, either.

Halogen means fluorine, chlorine, bromine and iodine. Preferred halogen is fluorine and chlorine. Further preferred halogen is fluorine. Alkyl in the liquid crystal compound has a straight or branched chain, and includes no cyclic alkyl. Straight-chain alkyl is generally preferred to branched-chain alkyl. A same rule also applies to a terminal group such as alkoxy and alkenyl. With regard to a configuration of 1,4-cyclohexylene, trans is preferred to cis for increasing the maximum temperature. Then, 2-fluoro-1,4-phenylene means two divalent groups described below. In a chemical formula, fluorine may be leftward (L) or rightward (R). A same rule also applies to an asymmetrical divalent group such as tetrahydropyran-2,5-diyl formed by eliminating two pieces of hydrogen from a ring.

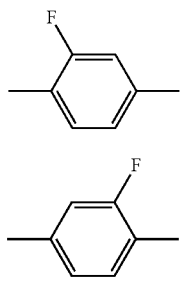

The invention includes the items described below.
Item 1. A compound represented by formula (1):

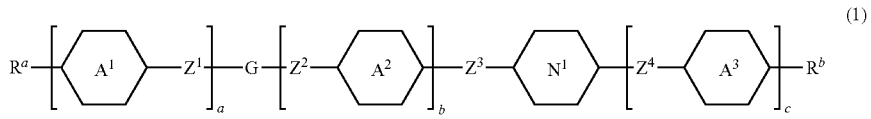

wherein, in formula (1),
$R^a$ and $R^b$ are independently hydrogen or alkyl having 1 to 10 carbons, and in the alkyl, at least one piece of —$CH_2$— may be replaced by —O— or —S—, —CO— or —$SiH_2$—, at least one piece of —$CH_2CH_2$— may be replaced by —CH=CH— or —C≡C—, and in the groups, at least one piece of hydrogen may be replaced by fluorine or chlorine, and $R^b$ may be fluorine, chlorine, —C≡N or —C≡C—C≡N;

ring $A^1$, ring $A^2$ and ring $A^3$ are independently 1,4-cyclohexylene, decahydronaphthalene-2,6-diyl or 1,4-phenylene, and in the groups, at least one piece of —$CH_2$— may be replaced by —O—, —S—, —CO— or —$SiH_2$—, at least one piece of —$CH_2CH_2$— may be replaced by —CH=CH— or —CH=N—, and in the divalent groups, at least one piece of hydrogen may be replaced by fluorine, chlorine, —C≡N, —$CF_3$, —$CHF_2$, —$CH_2F$, —$OCF_3$, —$OCHF_2$ or —$OCH_2F$;

ring $N^1$ is 1,4-cyclohexylene, decahydronaphthalene-2,6-diyl, 1,2,3,4-tetrahydronaphthalene-2,6-diyl, 2,6,7-trioxabicyclo[2.2.2]octane-1,4-diyl, 1,4-phenylene, naphthalene-2,6-diyl, 9,10-dihydrophenanthrene-2,7-diyl, 9H-xanthene-2,6-diyl or 9H-fluorene-2,7-diyl, and in the groups, at least one piece of —$CH_2$— may be replaced by —O—, —S—, —CO— or —$SiH_2$—, at least one piece of —$CH_2CH_2$— may be replaced by —CH=CH— or —CH=N—, and in the divalent groups, at least one piece of hydrogen may be replaced by fluorine, chlorine, —C≡N, —$CF_3$, —$CHF_2$, —$CH_2F$, —$OCF_3$, —$OCHF_2$ or —$OCH_2F$;

G is a divalent group represented by formula (pr-1) or (pr-2);

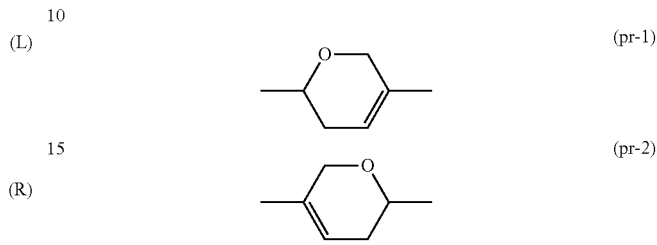

wherein,
$Z^1$, $Z^2$, $Z^3$ and $Z^4$ are independently a single bond or alkylene having 1 to 6 carbons, and in the alkylene, at least one piece of —$CH_2$— may be replaced by —O—, —S—, —CO— or —$SiH_2$— one or two pieces of —$CH_2CH_2$— may be replaced by —CH=CH— or —C≡C—, and in the divalent groups, at least one piece of hydrogen may be replaced by fluorine or chlorine;

a, b and c are independently 0, 1 or 2, and a sum of a, b and c is an integer from 0 to 3;

when $R^a$ is —$C_3H_7$, $R^b$ is —$OC_2H_5$, a is 1, b and c are 0, ring $A^1$ is tetrahydropyran-2,5-diyl, $Z^1$ and $Z^3$ are a single bond and ring $N^1$ is 2,3-difluoro-1,4-phenylene, G is a divalent group represented by formula (pr-2);

when $R^a$ is —$C_5H_{11}$, $R^b$ is —$OC_2H_5$, a, b and c are 0, $Z^3$ is a single bond and ring $N^1$ is 2,3-difluoro-1,4-phenylene, G is a divalent group represented by formula (pr-2);

when $R^a$ is —CH=$CH_2$ or —$C_2H_5$, $R^b$ is —$OC_2H_5$, a, b and c are 0, $Z^3$ is a single bond and ring $N^1$ is 2,3-difluoro-1,4-phenylene, G is a divalent group represented by formula (pr-1).

Item 2. The compound according to item 1, represented by formula (1-1):

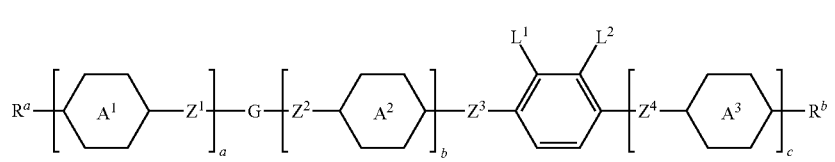

wherein, in formula (1-1),
$R^a$ and $R^b$ are independently hydrogen, alkyl having 1 to 10 carbons, alkoxy having 1 to 9 carbons, alkoxyalkyl having 2 to 9 carbons, alkenyl having 2 to 10 carbons or alkenyloxy having 2 to 9 carbons, and $R^b$ may be fluorine, chlorine, —C≡N, —C≡C—C≡N, alkyl having 1 to 10 carbons in which at least one piece of hydrogen is replaced by fluorine or chlorine, or alkoxy having 1 to 9 carbons in which at least one piece of hydrogen is replaced by fluorine or chlorine;

ring $A^1$, ring $A^2$ and ring $A^3$ are independently 1,4-cyclohexylene, decahydronaphthalene-2,6-diyl or 1,4-phenylene, and in the groups, at least one piece of —$CH_2$— may be replaced by —O—, —S—, —CO or —$SiH_2$—, at least one piece of —$CH_2CH_2$— may be replaced by —CH=CH— or —CH=N—, and in the divalent groups, at least one piece of hydrogen may be replaced by fluorine, chlorine, —C≡N, —$CF_3$, —$CHF_2$, —$CH_2F$, —$OCF_3$, —$OCHF_2$ or —$OCH_2F$;

G is a divalent group represented by formula (pr-1) or (pr-2);

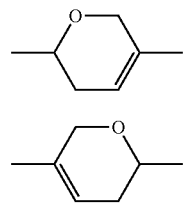

(pr-1)

(pr-2)

wherein, $Z^1$, $Z^2$, $Z^3$ and $Z^4$ are independently a single bond, —COO—, —OCO—, —$CH_2O$—, —$OCH_2$—, —$CF_2O$—, —$OCF_2$— or —$CH_2CH_2$—;

$L^1$ and $L^2$ are independently fluorine, chlorine, —$CF_3$, —$CHF_2$, —$CH_2F$, —$OCF_3$, —$OCHF_2$ or —$OCH_2F$;

a, b and c are independently 0, 1 or 2, and a sum of a, b and c is 0, 1 or 2;

when $R^a$ is —$C_3H_7$, $R^b$ is —$OC_2H_5$, a is 1, b and c are 0, ring $A^1$ is tetrahydropyran-2,5-diyl, $Z^1$ and $Z^3$ are a single bond and $L^1$ and $L^2$ are fluorine, G is a divalent group represented by formula (pr-2);

when $R^a$ is —$C_5H_{11}$, $R^b$ is —$OC_2H_5$, a, b and c are 0, $Z^3$ is a single bond and $L^1$ and $L^2$ are fluorine, G is a divalent group represented by formula (pr-2); and when $R^a$ is —CH=$CH_2$ or —$C_2H_5$, $R^b$ is —$OC_2H_5$, a, b and c are 0, $Z^3$ is a single bond and $L^1$ and $L^2$ are fluorine, G is a divalent group represented by formula (pr-1).

Item 3. The compound according to item 1, represented by formula (1-2) or (1-3):

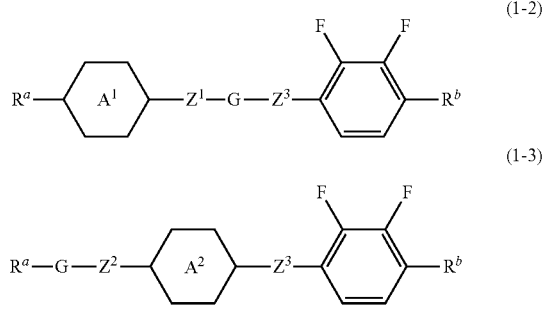

wherein, in formula (1-2) or (1-3), $R^a$ and $R^b$ are independently hydrogen, alkyl having 1 to 10 carbons, alkoxy having 1 to 9 carbons, alkoxyalkyl having 2 to 9 carbons, alkenyl having 2 to 10 carbons or alkenyloxy having 2 to 9 carbons;

ring $A^1$ and ring $A^2$ are independently 1,4-cyclohexylene, 1,4-cyclohexenylene, 1,4-phenylene, 2-fluoro-1,4-phenylene or 2, 3-difluoro-1,4-phenylene;

G is a divalent group represented by formula (pr-1) or (pr-2);

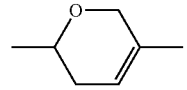

(pr-1)

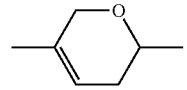

(pr-2)

wherein, $Z^1$, $Z^2$ and $Z^3$ are independently a single bond, —COO—, —OCO—, —$CH_2O$—, —$OCH_2$— or —$CH_2CH_2$—.

Item 4. The compound according to item 1, represented by any one of formulas (1-2-1) to (1-2-6) and formulas (1-3-1) to (1-3-6):

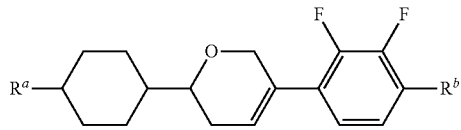

(1-2-1)

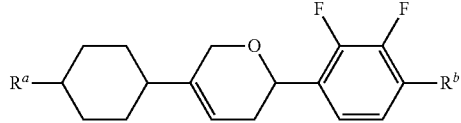

(1-2-2)

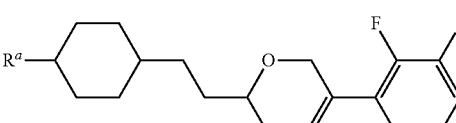

(1-2-3)

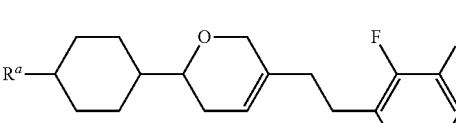

(1-2-4)

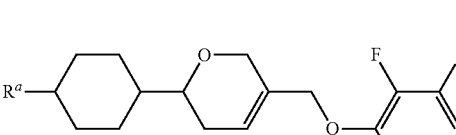

(1-2-5)

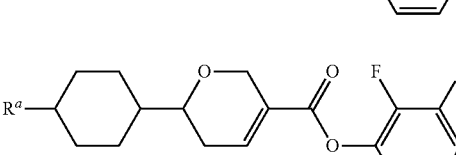

(1-2-6)

-continued

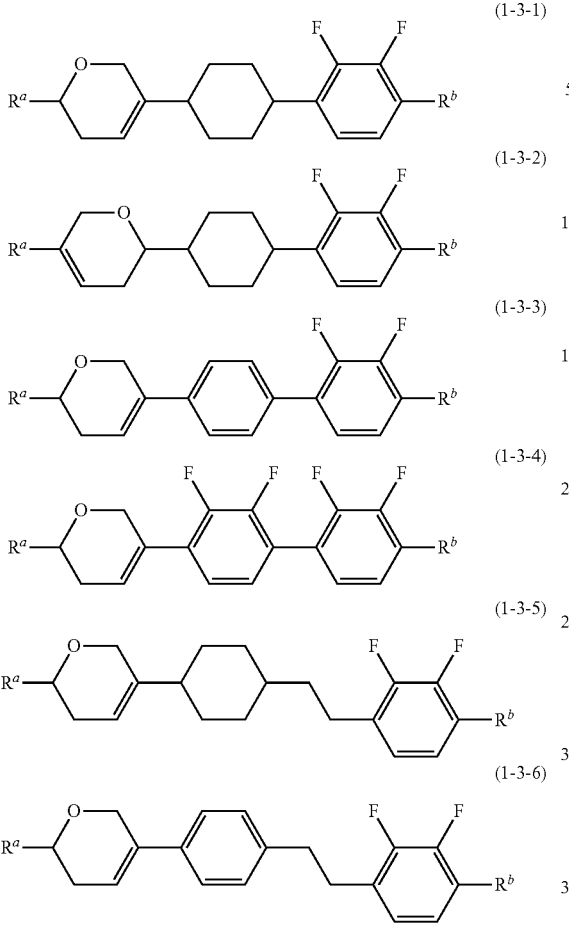

(1-3-1)
(1-3-2)
(1-3-3)
(1-3-4)
(1-3-5)
(1-3-6)

wherein, in formulas (1-2-1) to (1-2-6) and formulas (1-3-1) to (1-3-6), $R^a$ and $R^b$ are independently hydrogen or alkyl having 1 to 10 carbons, alkoxy having 1 to 9 carbons, alkoxyalkyl having 2 to 9 carbons, alkenyl having 2 to 10 carbons or alkenyloxy having 2 to 9 carbons.

Item 5. The compound according to item 4, wherein, in formulas (1-2-1) to (1-2-6) and formulas (1-3-1) to (1-3-6) described in item 4, $R^a$ is alkyl having 1 to 10 carbons, and $R^b$ is alkoxy having carbons 1 to 9.

Item 6. The compound according to item 1, represented by formula (1-4):

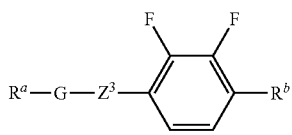

(1-4)

wherein, in formula (1-4), $R^a$ and $R^b$ are independently hydrogen, alkyl having 1 to 10 carbons, alkoxy having carbons 1 to 9, alkoxyalkyl having 2 to 9 carbons, alkenyl having 2 to 10 carbons or alkenyloxy having carbons 2 to 9;

G is a divalent group represented by formula (pr-1) or (pr-2);

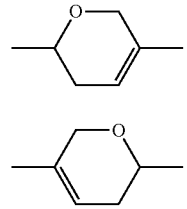

(pr-1)

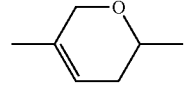

(pr-2)

wherein, $Z^3$ is a single bond, —COO—, —OCO—, —CH$_2$O—, —OCH$_2$— or —CH$_2$CH$_2$—;

when $R^a$ is —C$_5$H$_{11}$, $R^b$ is —OC$_2$H$_5$ and $Z^3$ is a single bond, G is a divalent group represented by formula (pr-2); and when $R^a$ is —CH=CH$_2$ or —C$_2$H$_5$, $R^b$ is —OC$_2$H$_5$ and $Z^3$ is a single bond, G is a divalent group represented by formula (pr-1).

Item 7. The compound according to item 1, represented by any one of formulas (1-4-1) to (1-4-4):

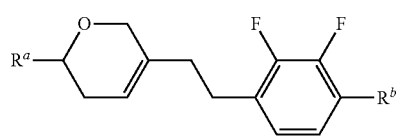

(1-4-1)

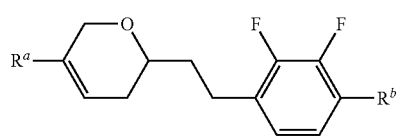

(1-4-2)

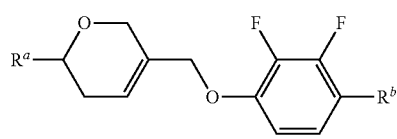

(1-4-3)

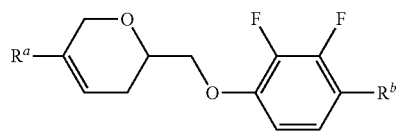

(1-4-4)

wherein, in formulas (1-4-1) to (1-4-4), $R^a$ and $R^b$ are independently hydrogen or alkyl having 1 to 10 carbons, alkoxy having carbons 1 to 9, alkoxyalkyl having 2 to 9 carbons, alkenyl having 2 to 10 carbons or alkenyloxy having carbons 2 to 9.

Item 8. The compound according to item 7, wherein, in formulas (1-4-1) to (1-4-4) described in item 7, $R^a$ is alkyl having 1 to 10 carbons, and $R^b$ is alkoxy having 1 to 9 carbons.

Item 9. A liquid crystal composition containing at least one compound selected from the group of compounds represented by formula (1) and at least one compound selected from the group of compounds represented by formulas (2) to (4):

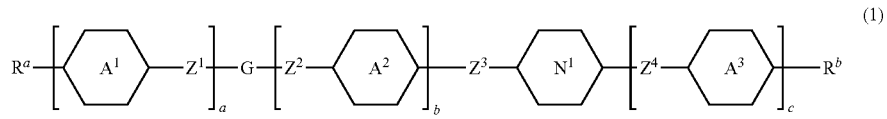

(1)

wherein, in formula (1), $R^a$ and $R^b$ are independently hydrogen or alkyl having 1 to 10 carbons, and in the alkyl, at least one piece of —CH$_2$— may be replaced by —O—, —S—, —CO— or —SiH$_2$—, at least one piece of —CH$_2$CH$_2$— may be replaced by —CH=CH— or —C≡C—, and in the groups, at least one piece of hydrogen may be replaced by fluorine or chlorine, and $R^b$ may be fluorine, chlorine, —C≡N or —C≡C—C≡N;

ring $A^1$, ring $A^2$ and ring $A^3$ are independently 1,4-cyclohexylene, decahydronaphthalene-2,6-diyl, 1,4-phenylene, and in the groups, at least one piece of —CH$_2$— may be replaced by —O—, —S—, —CO— or —SiH$_2$—, at least one piece of —CH$_2$CH$_2$— may be replaced by —CH=CH— or —CH=N—, and in the divalent groups, at least one piece of hydrogen may be replaced by fluorine, chlorine, —C≡N, —CF$_3$, —CHF$_2$, —CH$_2$F, —OCF$_3$, —OCHF$_2$ or —OCH$_2$F;

ring $N^1$ is 1,4-cyclohexylene, decahydronaphthalene-2,6-diyl, 1,2,3,4-tetrahydronaphthalene-2,6-diyl, 2,6,7-trioxabicyclo[2.2.2]octane-1,4-diyl, 1,4-phenylene, naphthalene-2,6-diyl, 9,10-dihydrophenanthrene-2,7-diyl, 9H-xanthene-2,6-diyl or 9H-fluorene-2,7-diyl, and in the groups, at least one piece of —CH$_2$— may be replaced by —O—, —S—, —CO— or —SiH$_2$—, at least one piece of —CH$_2$CH$_2$— may be replaced by —CH=CH— or —CH=N—, and in the divalent groups, at least one piece of hydrogen may be replaced by fluorine, chlorine, —C≡N, —CF$_3$, —CHF$_2$, —CH$_2$F, —OCF$_3$, —OCHF$_2$ or —OCH$_2$F;

G is a divalent group represented by formula (pr-1) or (pr-2);

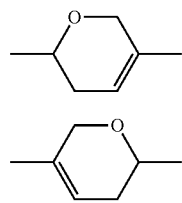

(pr-1)

(pr-2)

wherein, $Z^1$, $Z^2$, $Z^3$ and $Z^4$ are independently a single bond or alkylene having 1 to 6 carbons, and in the alkylene, at least one piece of —CH$_2$— may be replaced by —O—, —S—, —CO— or —SiH$_2$— one or two pieces of —CH$_2$CH$_2$— may be replaced by —CH=CH— or —C≡C—, and in the divalent groups, at least one piece of hydrogen may be replaced by fluorine or chlorine; and a, b and c are independently 0, 1 or 2, and a sum of a, b and c is an integer from 0 to 3;

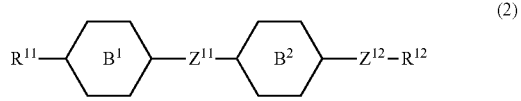

(2)

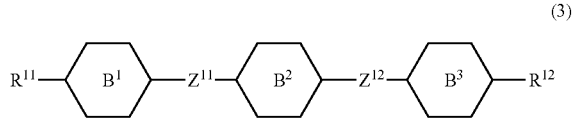

(3)

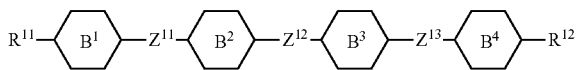

(4)

wherein, in formulas (2) to (4), $R^{11}$ and $R^{12}$ are independently alkyl having 1 to 10 carbons or alkenyl having 2 to 10 carbons, and in the alkyl and the alkenyl, at least one piece of —CH$_2$— may be replaced by —O—, and in the groups, at least one piece of hydrogen may be replaced by fluorine;

ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl; and $Z^{11}$, $Z^{12}$ and $Z^{13}$ are independently a single bond, —COO—, —CH$_2$CH$_2$—, —CH=CH— or —C≡C—.

Item 10. The liquid crystal composition according to item 9, further containing at least one compound selected from the group of compounds represented by formulas (5) to (11):

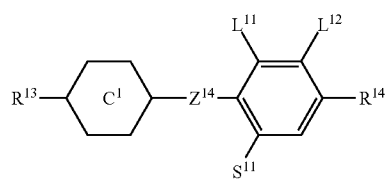

(5)

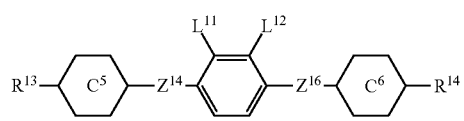

(7)

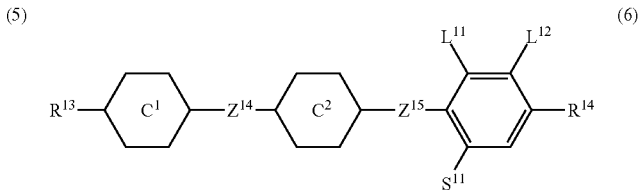

(6)

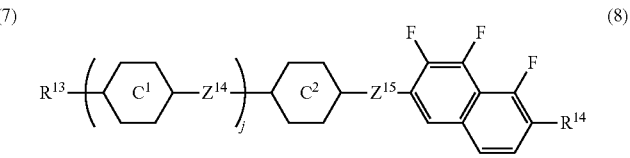

(8)

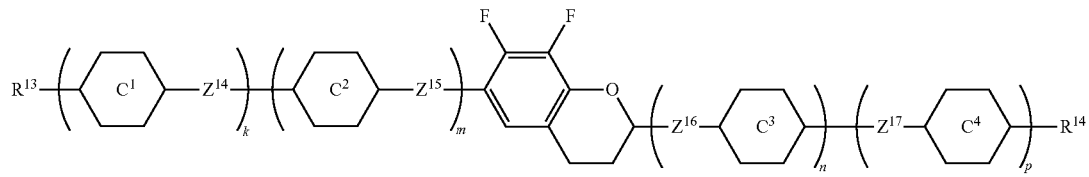

(9)

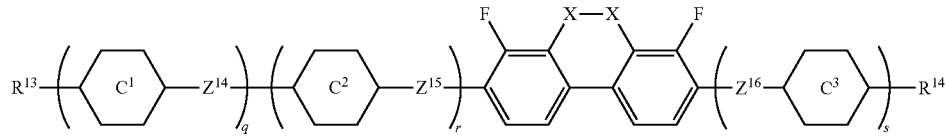

(10)

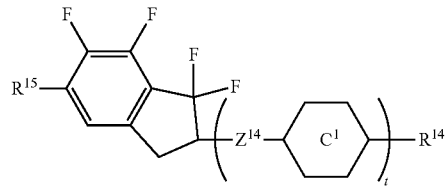

(11)

wherein, in formulas (5) to (11), $R^{13}$, $R^{14}$ and $R^{15}$ are independently alkyl having 1 to 10 carbons or alkenyl having 2 to 10 carbons, and in the alkyl and the alkenyl, at least one piece of —$CH_2$— may be replaced by —O—, and in the groups, at least one piece of hydrogen may be replaced by fluorine, and $R^{15}$ may be hydrogen or fluorine;

ring $C^1$, ring $C^2$, ring $C^3$ and ring $C^4$ are independently 1,4-cyclohexylene, 1,4-cyclohexenylene, 1,4-phenylene in which at least one piece of hydrogen may be replaced by fluorine, tetrahydropyran-2,5-diyl or decahydronaphthalene-2,6-diyl;

ring $C^5$ and ring $C^6$ are independently 1,4-cyclohexylene, 1,4-cyclohexenylene, 1,4-phenylene, tetrahydropyran-2,5-diyl or decahydronaphthalene-2,6-diyl;

$Z^{14}$, $Z^{15}$, $Z^{16}$ and $Z^{17}$ are independently a single bond, —COO—, —$CH_2O$—, —$OCF_2$—, —$CH_2CH_2$— or —$OCF_2CH_2CH_2$—;

$L^{11}$ and $L^{12}$ are independently fluorine or chlorine;

$S^{11}$ is hydrogen or methyl;

X is —CHF— or —$CF_2$—; and j, k, m, n, p, q, r and s are independently 0 or 1, a sum of k, m, n and p is 1 or 2, a sum of q, r and s is 0, 1, 2 or 3 and t is 1, 2 or 3.

Item 11. The liquid crystal composition according to item 9, further containing at least one compound selected from the group of compounds represented by formulas (12) to (14).

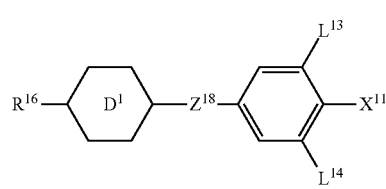

(12)

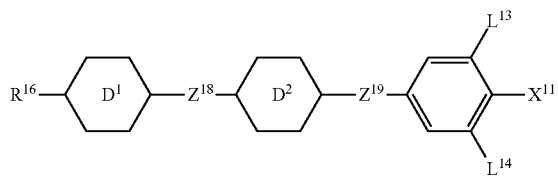

(13)

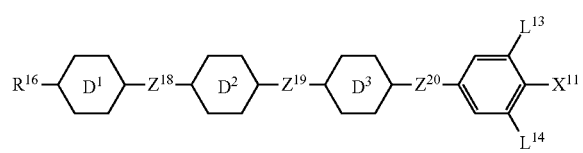

(14)

wherein, in formulas (12) to (14), $R^{16}$ is alkyl having 1 to 10 carbons or alkenyl having 2 to 10 carbons, and in the alkyl and the alkenyl, at least one piece of —$CH_2$— may be replaced by —O—, and in the groups, at least one piece of hydrogen may be replaced by fluorine;

$X^{11}$ is fluorine, chlorine, —$CF_3$, —$CHF_2$, —$CH_2F$, —$OCF_3$, —$OCHF_2$, —$OCF_2CHF_2$ or —$OCF_2CHFCF_3$;

ring $D^1$, ring $D^2$ and ring $D^3$ are independently 1,4-cyclohexylene, 1,4-phenylene in which at least one piece of hydrogen may be replaced by fluorine, tetrahydropyran-2,5-diyl, 1,3-dioxane-2,5-diyl or pyrimidine-2,5-diyl;

$Z^{18}$, $Z^{19}$ and $Z^{20}$ are independently a single bond, —COO—, —$CH_2O$—, —$CF_2O$—, —$OCF_2$—, —$CH_2CH_2$—, —CH=CH—, —C≡C— or —$(CH_2)_4$—; and $L^{13}$ and $L^{14}$ are independently hydrogen or fluorine.

Item 12. The liquid crystal composition according to item 9, further containing at least one compound selected from the group of compounds represented by formula (15):

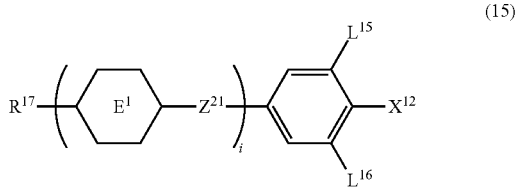

(15)

wherein, in formula (15),

R$^{17}$ is alkyl having 1 to 10 carbons or alkenyl having 2 to 10 carbons, and in the alkyl and the alkenyl, at least one piece of —CH$_2$— may be replaced by —O—, and in the groups, at least one piece of hydrogen may be replaced by fluorine;

X$^{12}$ is —C≡N or —C≡C—C≡N;

ring E$^1$ is 1,4-cyclohexylene, 1,4-phenylene in which at least one piece of hydrogen may be replaced by fluorine, tetrahydropyran-2,5-diyl, 1,3-dioxane-2,5-diyl or pyrimidine-2,5-diyl;

Z$^{21}$ is a single bond, —COO—, —CH$_2$O—, —CF$_2$O—, —OCF$_2$—, —CH$_2$CH$_2$— or —C≡C—;

L$^{15}$ and L$^{16}$ are independently hydrogen or fluorine; and i is 1, 2, 3 or 4.

Item 13. A liquid crystal display device including the liquid crystal composition according to item 9.

The invention further includes the following items: (a) the composition, further containing at least one optically active compound and/or polymerizable compound; and (b) the composition, further containing at least one antioxidant and/or ultraviolet light absorber.

The invention further includes the following items: (c) the composition, further containing one, two or at least three of additives selected from the group of a polymerizable compound, a polymerization initiator, a polymerization inhibitor, a optically active compound, an antioxidant, an ultraviolet light absorber, a light stabilizer, a heat stabilizer, a dye and an antifoaming agent; and (d) the composition in which a maximum temperature of a nematic phase is 70° C. or more, optical anisotropy (measured at 25° C.) at a wavelength of 589 nm is 0.08 or more, and dielectric anisotropy (measured at 25° C.) at a frequency of 1 kHz is −2 or less.

The invention still further includes the following items: (e) a device including the composition and having a PC, TN, STN, ECB, OCB, IPS, VA, FFS, FPA or PSA mode; (f) an AM device including the composition; (g) a transmissive device, including the composition; (h) use of the composition as a composition having a nematic phase; and (i) use of an optically active composition by adding an optically active compound to the composition.

An embodiment of compound (1), a synthetic method, the liquid crystal composition and the liquid crystal display device will be described in the order.

1. Embodiment of Compound (1)

Compound (1) has a feature having a divalent group represented by formula (pr-1) or (pr-2) below.

(pr-1)

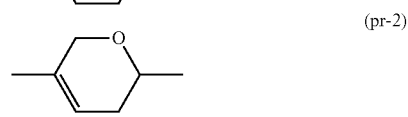

(pr-2)

The compound is physically and chemically significantly stable under conditions in which the device is ordinarily used, and has a good compatibility with other liquid crystal compounds. The composition containing the compound is stable under conditions in which the device is ordinarily used. Even if the composition is stored at a low temperature, the compound has a low trend of causing precipitation in the form of crystals (or the smectic phase). The compound has general physical properties required for the component of the composition, namely a suitable optical anisotropy and a suitable dielectric anisotropy.

Preferred examples of terminal groups R$^a$ and R$^b$, rings A$^1$, A$^2$ and A$^3$, ring N$^1$, bonding groups Z$^1$, Z$^2$ and Z$^3$ and lateral groups L$^1$ and L$^2$ in compound (1) and compound (1-1) are as described below. A same rule also applies to a subordinate formula of compound (1) and compound (1-1). The physical properties can be arbitrarily adjusted by suitably combining the groups in compound (1). Compound (1) may contain an isotope such as $^2$H (deuterium) or $^{13}$C in an amount larger than an amount of natural abundance because no significant difference exists in the physical properties of the compound. Moreover, a definition of the symbol in compound (1) is as described in item 1.

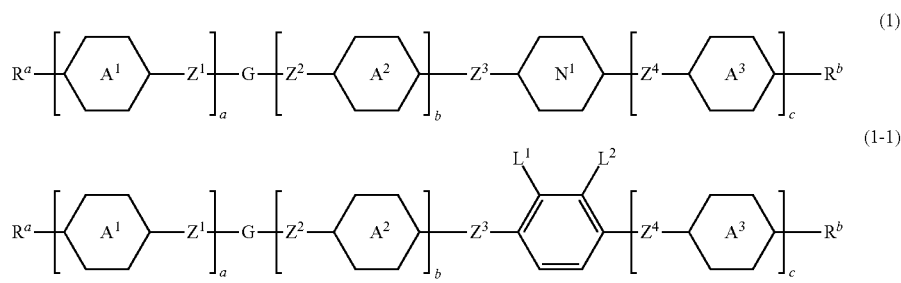

In formulas (1) and (1-1), R$^a$ and R$^b$ are independently hydrogen or alkyl having 1 to 10 carbons, and in the alkyl, at least one piece of —CH$_2$— may be replaced by —O—, —S—, —CO— or —SiH$_2$—, at least one piece of —CH$_2$CH$_2$— may be replaced by —CH═CH— or —C≡C—, and in the groups, at least one piece of hydrogen may be replaced by fluorine or chlorine, and R$^b$ may be fluorine, chlorine, —C≡N or —C≡C—C≡N.

Preferred R$^a$ or R$^b$ is hydrogen, alkyl, alkoxy, alkoxyalkyl, alkoxyalkoxy, alkylthio, alkylthioalkoxy, acyl, acylalkyl, acyloxy, acyloxyalkyl, alkoxycarbonyl, alkoxycarbonylalkyl, alkenyl, alkenyloxy, alkenyloxyalkyl, alkoxyalkenyl, alkynyl, alkynyloxy, silaalkyl and disilaalkyl, and in the groups, at least one piece of hydrogen may be replaced by fluorine or chlorine. The example includes a group in which at least two pieces of hydrogen is replaced by both fluorine and chlorine. The group in which at least one piece of hydrogen is replaced by fluorine is further preferred. In the groups, a straight chain is preferred to a branched chain. Even when $R^a$ or $R^b$ has the branched chain, a case where the branched chain is optically active is preferred. Further preferred $R^a$ or $R^b$ is alkyl, alkoxy, alkoxyalkyl, alkenyl, monofluoroalkyl, polyfluoroalkyl, monofluoroalkoxy and polyfluoroalkoxy. In addition to the groups, $R^b$ may be fluorine, chlorine, —C≡N or —C≡C—C≡N.

A preferred configuration of —CH═CH— in alkenyl depends on a position of a double bond. Trans is preferred in alkenyl such as 1-propenyl, 1-butenyl, 1-pentenyl, 1-hexenyl, 3-pentenyl and 3-hexenyl. Cis is preferred in alkenyl such as 2-butenyl, 2-pentenyl and 2-hexenyl.

Specific $R^a$ or $R^b$ includes methyl, ethyl, propyl, butyl, pentyl, hexyl, heptyl, octyl, methoxy, ethoxy, propoxy, butoxy, pentyloxy, hexyloxy, heptyloxy, ethoxymethyl, methoxyethyl, methoxypropyl, ethoxymethyl, ethoxyethyl, ethoxypropyl, propoxymethyl, butoxymethyl, pentoxymethyl, vinyl, 1-propenyl, 2-propenyl, 1-butenyl, 2-butenyl, 3-butenyl, 1-pentenyl, 2-pentenyl, 3-pentenyl, 4-pentenyl, 2-propenyloxy, 2-butenyloxy, 2-pentenyloxy, 1-propynyl and 1-pentenyl.

Specific $R^a$ or $R^b$ also includes 2-fluoroethyl, 3-fluoropropyl, 2,2,2-trifluoroethyl, 2-fluorovinyl, 2,2-difluorovinyl, 2-fluoro-2-vinyl, 3-fluoro-1-propenyl, 3,3,3-trifluoro-1-propenyl, 4-fluoro-1-propenyl and 4,4-difluoro-3-butenyl.

Specific $R^b$ includes fluorine, chlorine, —C≡N, —CF$_3$, —CHF$_2$, —CH$_2$F, —CF$_2$CF$_3$, —CF$_2$CHF$_2$, —CF$_2$CH$_2$F, —CF$_2$CF$_2$CF$_3$, —CF$_2$CHFCF$_3$, —CHFCF$_2$CF$_3$, —OCF$_3$, —OCHF$_2$, —OCH$_2$F, —OCF$_2$CF$_3$, —OCF$_2$CHF$_2$, —OCF$_2$CH$_2$F, —OCF$_2$CF$_2$CF$_3$, —OCF$_2$CHFCF$_3$ and —OCHFCF$_2$CF$_3$.

Further preferred $R^a$ or $R^b$ is ethyl, propyl, butyl, pentyl, methoxy, ethoxy, propoxy, butoxy, pentyloxy, methoxymethyl, ethoxymethyl, propoxymethyl, vinyl, 1-propenyl, 2-propenyl, 1-butenyl, 2-butenyl, 3-butenyl, 1-pentenyl, 2-pentenyl, 3-pentenyl, 4-pentenyl, 2-propenyloxy, 2-butenyloxy, 2-pentenyloxy, —OCF$_3$, —OCHF$_2$, —OCH$_2$F, —OCF$_2$CF$_3$, —OCF$_2$CHF$_2$, —OCF$_2$CH$_2$F, —OCF$_2$CF$_2$CF$_3$, —OCF$_2$CHFCF$_3$, —OCHFCF$_2$CF$_3$, fluorine, chlorine and —C≡N. Most preferred $R^a$ or $R^b$ is ethyl, propyl, butyl, pentyl, methoxy, ethoxy, propoxy, methoxymethyl, vinyl, 1-propenyl, 3-butenyl, 3-pentenyl, —OCF$_3$, —OCHF$_2$, —CF$_3$, —CHF$_2$, —CH$_2$F, —OCF$_2$CHF$_2$, —OCF$_2$CHFCF$_3$, fluorine and —C≡N.

In formulas (1) and (1-1), ring $A^1$, ring $A^2$ and ring $A^3$ are independently 1,4-cyclohexylene, decahydronaphthalene-2,6-diyl, 1,4-phenylene, and in the groups, at least one piece of —CH$_2$— may be replaced by —O—, —S—, —CO— or —SiH$_2$—, at least one piece of —CH$_2$CH$_2$— may be replaced by —CH═CH— or —CH═N—, and in the divalent groups, at least one piece of hydrogen may be replaced by fluorine, chlorine, —C≡N, —CF$_3$, —CHF$_2$, —CH$_2$F, —OCF$_3$, —OCHF$_2$ or —OCH$_2$F.

Preferred examples of "in the groups, at least one piece of —CH$_2$— may be replaced by —O—, —S—, —CO— or —SiH$_2$—, and at least one piece of —CH$_2$CH$_2$— may be replaced by —CH═CH— or —CH═N—" include a divalent group represented by formulas (16-1) to (16-50) below. Further preferred examples include a divalent group represented by formulas (16-1) to (16-4), formula (16-15), formula (16-23), formulas (16-27) to (16-29), formula (16-36), formula (16-39) and formula (16-45).

(16-15)
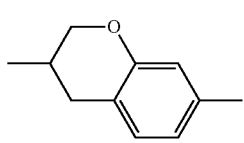
(16-16)
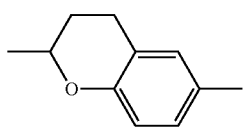
(16-17)
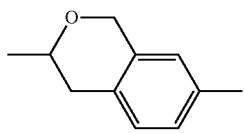
(16-18)
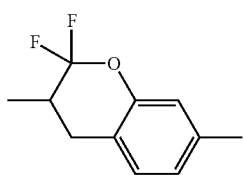
(16-19)
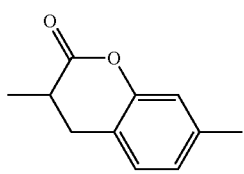
(16-20)
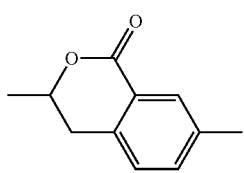
(16-21)
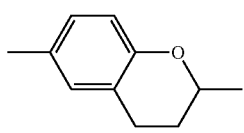
(16-22)
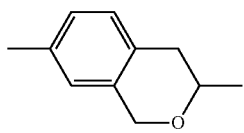
(16-23)
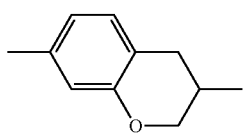
(16-24)
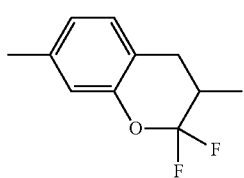
(16-25)
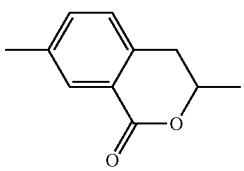
(16-26)
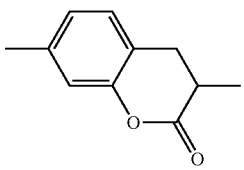
(16-27)
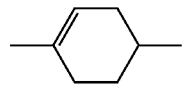
(16-28)
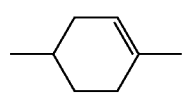
(16-29)
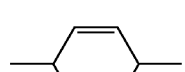
(16-30)
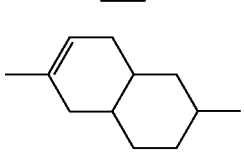
(16-31)
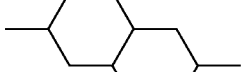
(16-32)
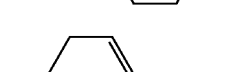
(16-33)
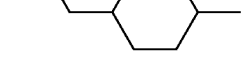
(16-34)
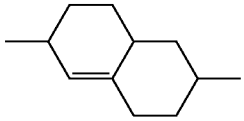
(16-35)
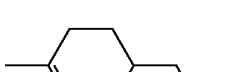
(16-36)
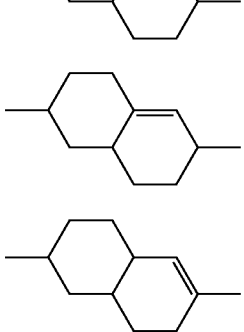

(16-37) 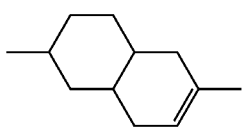
(16-38) 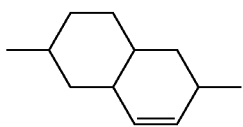
(16-39) 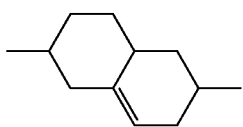
(16-40) 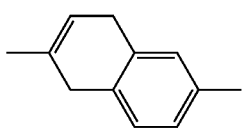
(16-41) 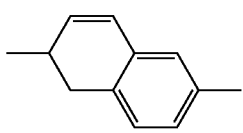
(16-42) 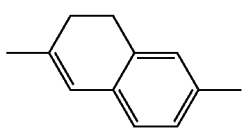
(16-43) 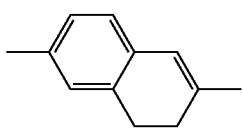
(16-44) 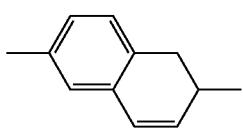
(16-45) 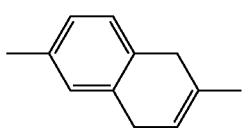
(16-46) 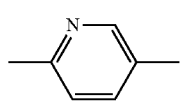
(16-47) 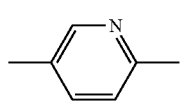
(16-48) 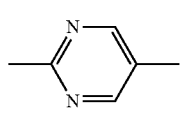
(16-49) 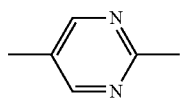
(16-50) 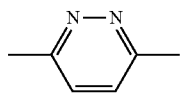
Preferred examples of "in the divalent groups, at least one piece of hydrogen may be replaced by fluorine, chlorine, —CF$_3$, —CHF$_2$, —CH$_2$F, —OCF$_3$, —OCHF$_2$ or —OCH$_2$F" include a divalent group represented by formulas (17-1) to (17-71) below. Further preferred examples include a divalent group represented by formulas (17-1) to (17-4), formula (17-6), formulas (17-10) to (17-15) and formulas (17-54) to (17-59).
(17-1) 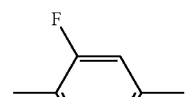
(17-2) 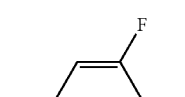
(17-3) 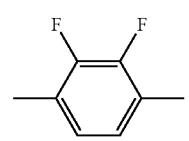
(17-4) 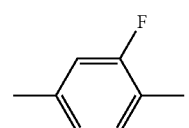
(17-5) 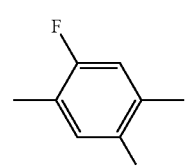
(17-6) 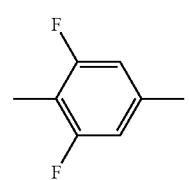
(17-7) 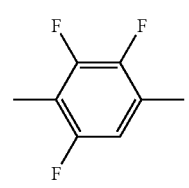

-continued
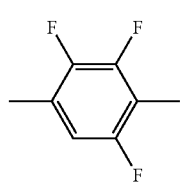 (17-8)
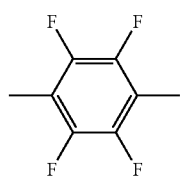 (17-9)
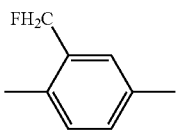 (17-10)
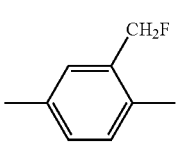 (17-11)
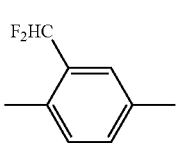 (17-12)
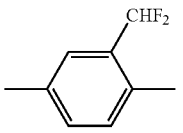 (17-13)
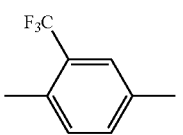 (17-14)
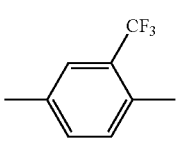 (17-15)
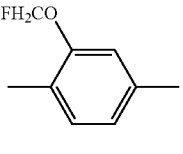 (17-16)
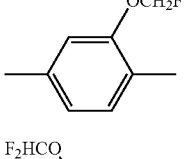 (17-17)
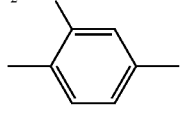 (17-18)
-continued
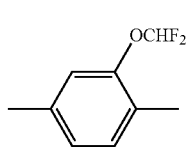 (17-19)
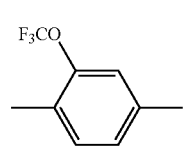 (17-20)
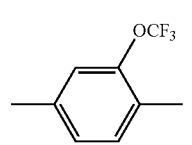 (17-21)
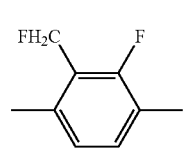 (17-22)
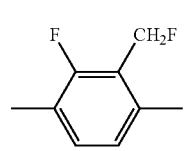 (17-23)
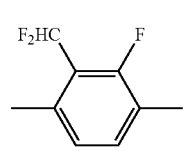 (17-24)
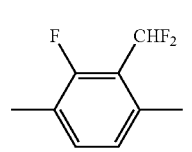 (17-25)
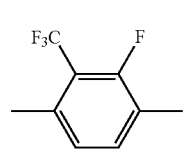 (17-26)
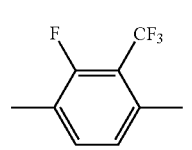 (17-27)
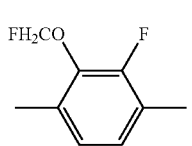 (17-28)
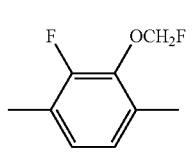 (17-29)

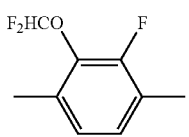 (17-30)
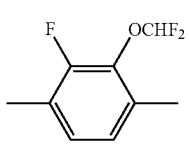 (17-31)
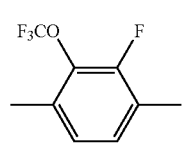 (17-32)
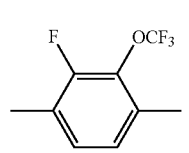 (17-33)
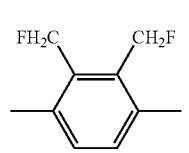 (17-34)
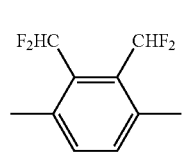 (17-35)
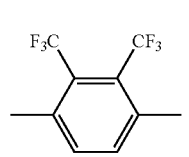 (17-36)
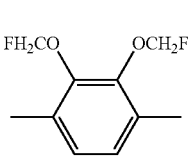 (17-37)
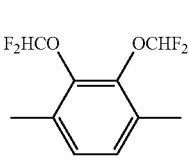 (17-38)
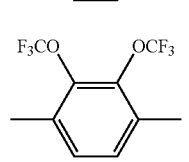 (17-39)
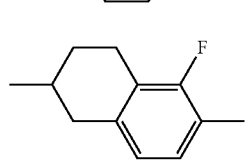 (17-40)
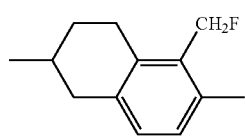 (17-41)
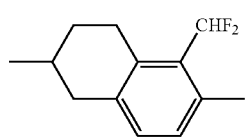 (17-42)
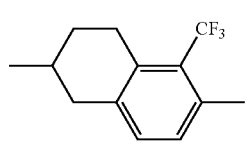 (17-43)
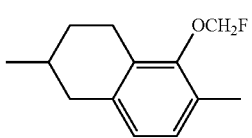 (17-44)
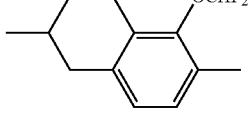 (17-45)
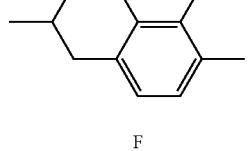 (17-46)
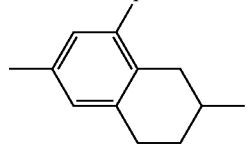 (17-47)
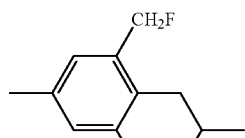 (17-48)
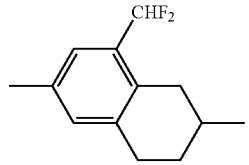 (17-49)
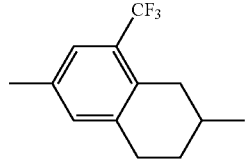 (17-50)

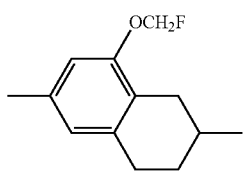 (17-51)
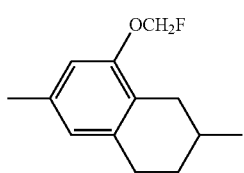 (17-52)
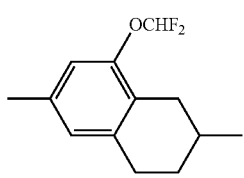 (17-53)
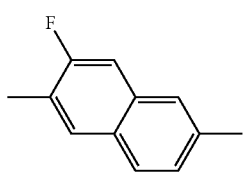 (17-54)
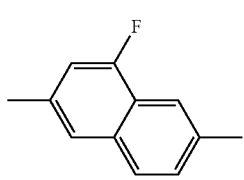 (17-55)
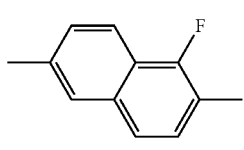 (17-56)
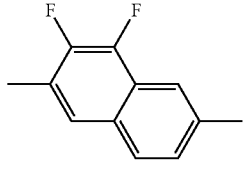 (17-57)
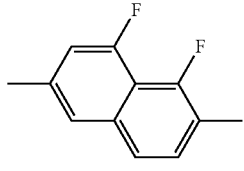 (17-58)
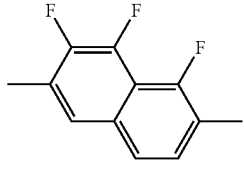 (17-59)
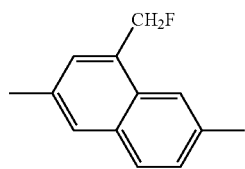 (17-60)
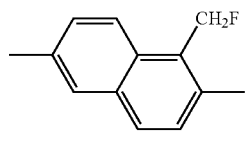 (17-61)
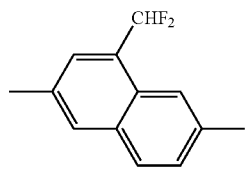 (17-62)
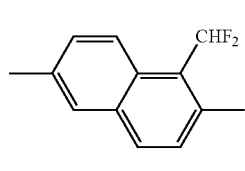 (17-63)
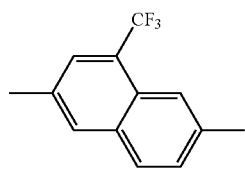 (17-64)
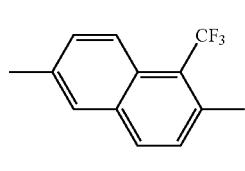 (17-65)
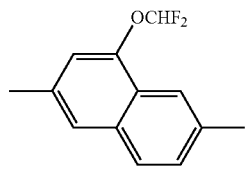 (17-66)
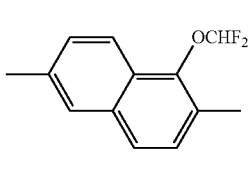 (17-67)
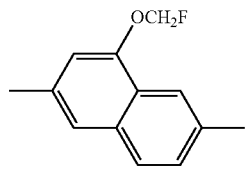 (17-68)
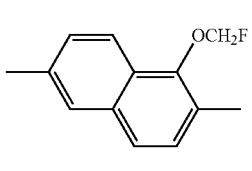 (17-69)

(17-70)

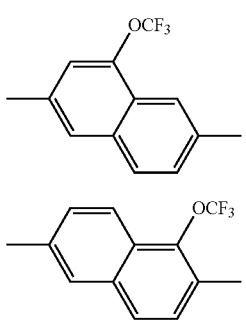

(17-71)

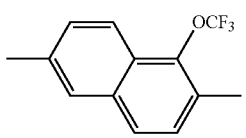

Further preferred ring A¹, ring A² or ring A³ is 1,4-cyclohexylene, 1,4-cyclohexenylene, 1,3-dioxane-2,5-diyl, 1,4-phenylene, 2-fluoro-1,4-phenylene, 2,3-difluoro-1,4-phenylene, 2,5-difluoro-1,4-phenylene, 2,6-difluoro-1,4-phenylene, 2,3,5-trifluoro-1,4-phenylene, pyridine-2,5-diyl, 3-fluoropyridine-2,5-diyl, pyrimidine-2,5-diyl, pyridazine-2,5-diyl, decahydronaphthalene-2,6-diyl, 1,2,3,4-tetrahydronaphthalene-2,6-diyl and naphthalene-2,6-diyl. With regard to a configuration of 1,4-cyclohexylene and 1,3-dioxane-2,5-diyl each, trans is preferred to cis.

Particularly preferred ring A¹, ring A² or ring A³ is 1,4-cyclohexylene, 1,3-dioxane-2,5-diyl, 1,4-phenylene, 2-fluoro-1,4-phenylene, 2,3-difluoro-1,4-phenylene, 2,5-difluoro-1,4-phenylene, 2,6-difluoro-1,4-phenylene, pyridine-2,5-diyl and pyrimidine-2,5-diyl. Most preferred ring A¹, ring A² or ring A³ is 1,4-cyclohexylene and 1,4-phenylene.

In formula (1), ring N¹ includes 1,4-cyclohexylene, decahydronaphthalene-2,6-diyl, 1,2,3,4-tetrahydronaphthalene-2,6-diyl, 2,6,7-trioxabicyclo[2.2.2]octane-1,4-diyl, 1,4-phenylene, naphthalene-2,6-diyl, 9,10-dihydrophenanthrene-2,7-diyl, 9H-xanthene-2,6-diyl or 9H-fluorene-2,7-diyl, and in the groups, at least one piece of —CH₂— may be replaced by —O—, —S—, —CO— or —SiH₂—, at least one piece of —CH₂CH₂— may be replaced by —CH=CH— or —CH=N—, and in the divalent groups, at least one piece of hydrogen may be replaced by fluorine, chlorine, —C≡N, —CF₃, —CHF₂, —CH₂F, —OCF₃, —OCHF₂ or —OCH₂F.

Preferred examples of "in the groups, at least one piece of —CH₂— may be replaced by —O—, —S—, —CO— or —SiH₂—, at least one piece of —CH₂CH₂— may be replaced by —CH=CH— or —CH=N—, and in the divalent groups, at least one piece of hydrogen may be replaced by fluorine, chlorine, —C≡N, —CF₃, —CHF₂, —CH₂F, —OCF₃, —OCHF₂ or —OCH₂F" include a divalent group represented by formulas (17-1) to (17-77). Further preferred specific examples include a divalent group represented by formulas (17-1) to (17-4), formula (17-6), formulas (17-10) to (17-15), formulas (17-54) to (17-59) and formulas (17-72) to (17-77).

(17-1)

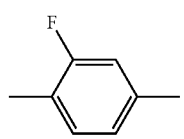

(17-2)

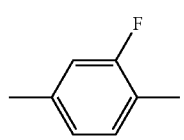

(17-3)

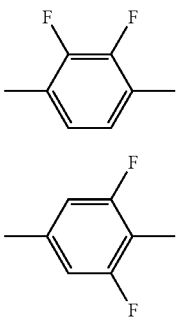

(17-4)

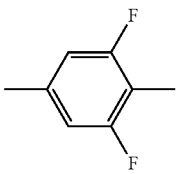

(17-5)

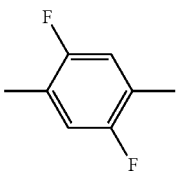

(17-6)

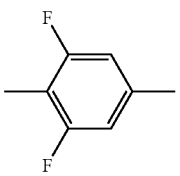

(17-7)

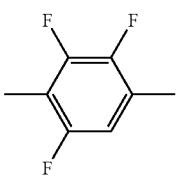

(17-8)

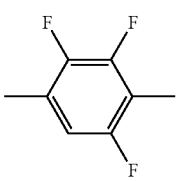

(17-9)

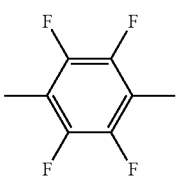

(17-10)

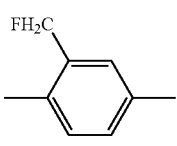

(17-11)

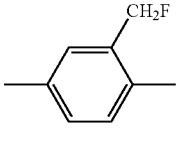

(17-12)

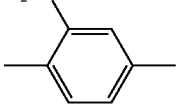

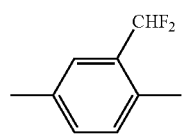 (17-13)
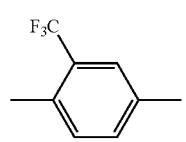 (17-14)
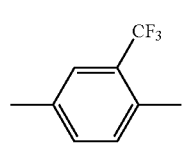 (17-15)
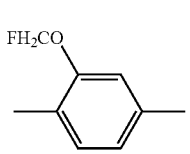 (17-16)
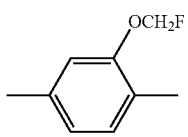 (17-17)
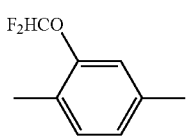 (17-18)
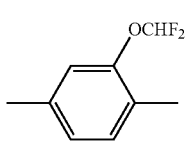 (17-19)
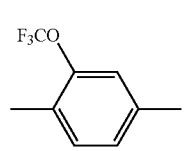 (17-20)
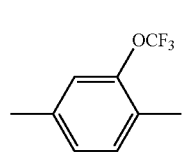 (17-21)
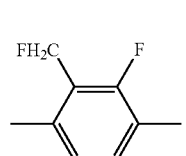 (17-22)
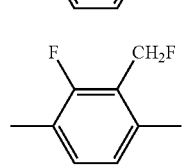 (17-23)
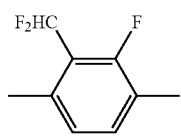 (17-24)
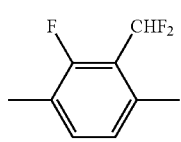 (17-25)
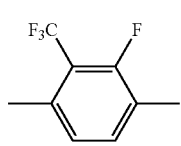 (17-26)
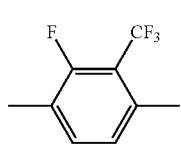 (17-27)
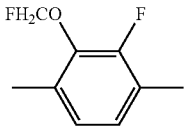 (17-28)
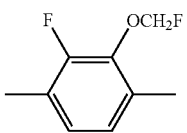 (17-29)
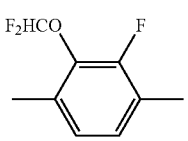 (17-30)
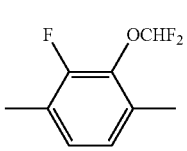 (17-31)
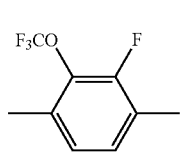 (17-32)
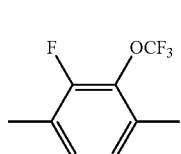 (17-33)
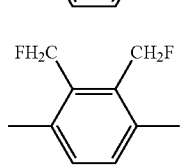 (17-34)

(17-35) (17-36) (17-37) (17-38) (17-39) (17-40) (17-41) (17-42) (17-43) (17-44) (17-45) (17-46) (17-47) (17-48) (17-49) (17-50) (17-51) (17-52) (17-53) (17-54)

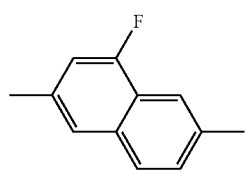 (17-55)
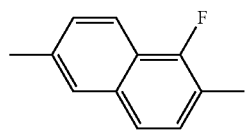 (17-56)
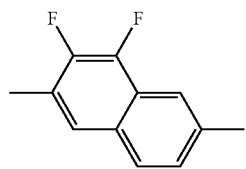 (17-57)
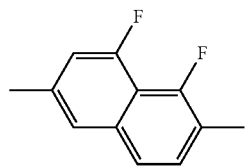 (17-58)
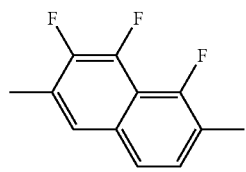 (17-59)
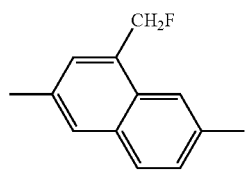 (17-60)
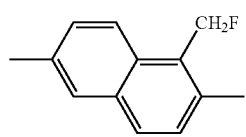 (17-61)
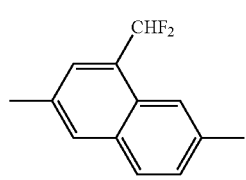 (17-62)
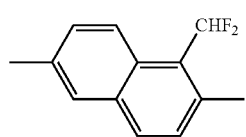 (17-63)
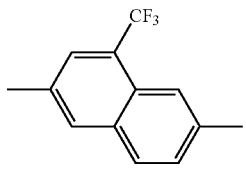 (17-64)
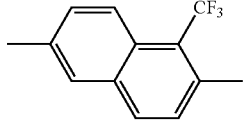 (17-65)
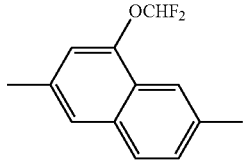 (17-66)
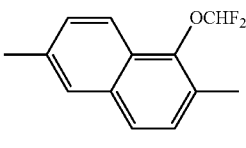 (17-67)
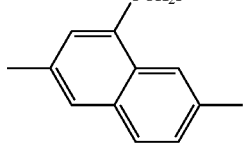 (17-68)
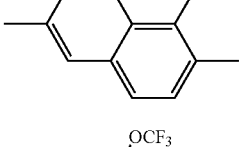 (17-69)
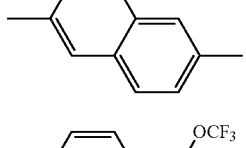 (17-70)
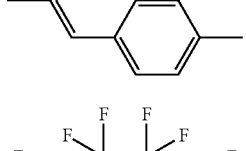 (17-71)
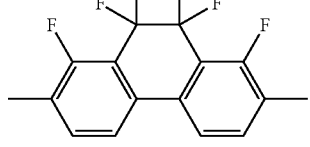 (17-72)
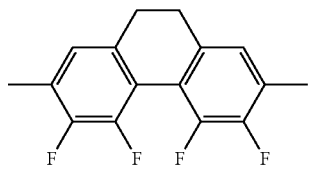 (17-73)

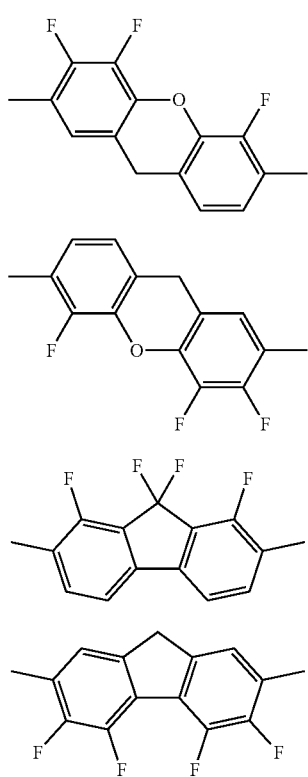

(17-74)

(17-75)

(17-76)

(17-77)

Further preferred ring $N^1$ is 2-fluoro-1,4-phenylene, 2,3-difluoro-1,4-phenylene, 2,5-difluoro-1,4-phenylene, 2,6-difluoro-1,4-phenylene, 2,3,5-trifluoro-1,4-phenylene and 3-fluoro pyridine-2,5-diyl.

Particularly preferred ring $N^1$ is 2-fluoro-1,4-phenylene and 2,3-difluoro-1,4-phenylene. Most preferred ring $N^1$ is 2,3-difluoro-1,4-phenylene.

In formulas (1) and (1-1), G is a divalent group represented by formula (pr-1) or (pr-2).

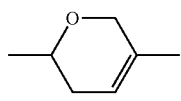

(pr-1)

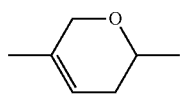

(pr-2)

A compound having the divalent group represented by formula (pr-1) is preferred in view of the large negative dielectric anisotropy. A compound having the divalent group represented by formula (pr-2) is also preferred in view of the large negative dielectric anisotropy.

In formulas (1) and (1-1), $Z^1$, $Z^2$, $Z^3$ and $Z^4$ are independently a single bond or alkylene having 1 to 6 carbons, and in the alkylene, at least one piece of —$CH_2$— may be replaced by —O—, —S—, —CO— or —$SiH_2$—, one or two pieces of —$CH_2CH_2$— may be replaced by —CH═CH— or —C≡C—, and in the divalent groups, at least one piece of hydrogen may be replaced by fluorine or chlorine.

Specific examples of $Z^1$, $Z^2$, $Z^3$ or $Z^4$ include a single bond, —COO—, —OCO—, —$CH_2O$—, —$OCH_2$—, —$CF_2O$—, —$OCF_2$—, —$CH_2CH_2$—, —CH═CH—, —CF═CH—, —CH═CF—, —CF═CF—, —$CH_2CO$—, —$COCH_2$—, —$CH_2SiH_2$—, —$SiH_2CH_2$—, —$(CH_2)_4$—, —$(CH_2)_2COO$—, —$(CH_2)_2OCO$—, —$OCO(CH_2)_2$—, —$COO(CH_2)_2$—, —$(CH_2)_2CF_2O$—, —$(CH_2)_2OCF_2$—, —$OCF_2(CH_2)_2$—, —$CF_2O(CH_2)_2$—, —$(CH_2)_3O$— or —$O(CH_2)_3$—.

Regarding to a configuration of a double bond of a bonding group such as —CH═CH—, —CF═CF—, —CH═CH—$(CH_2)_2$— or —$(CH_2)_1$—CH═CH—, trans is preferred to cis.

Preferred $Z^1$, $Z^2$, $Z^3$ or $Z^4$ is a single bond, —COO—, —OCO—, —$CH_2O$—, —$OCH_2$—, —$CF_2O$—, —$OCF_2$—, —$CH_2CH_2$—, —CH═CH—, —CF═CF—, —C≡C— and —$(CH_2)_4$—. Further preferred $Z^1$, $Z^2$ or $Z^3$ is a single bond, —COO—, —OCO—, —$CF_2O$—, —$OCF_2$—, —CH═CH—, —$CH_2CH_2$— and —C≡C—. Most Preferred $Z^1$, $Z^2$, $Z^3$ or $Z^4$ is a single bond.

In formula (1-1), $L^1$ and $L^2$ are independently fluorine, chlorine, —C≡N, —$CF_3$, —$CHF_2$, —$CH_2F$, —$OCF_3$, —$OCHF_2$ or —$OCH_2F$. Preferred $L^1$ or $L^2$ is fluorine, chlorine, —$CF_3$, —$CHF_2$, —$CH_2F$, —$OCF_3$, —$OCHF_2$ or —$OCH_2F$. Further preferred $L^1$ or $L^2$ is fluorine or chlorine. Particularly preferred $L^1$ or $L^2$ is fluorine.

In formulas (1) and (1-1), a, b and c are independently 0, 1 or 2, and a sum of a, b and c is an integer from 0 to 3. Compound (1) has a bicycle to a pentacycle. The rings include a condensed ring and a bridged ring in addition to an ordinary six-membered ring. When compound (1) has the bicycle, the compatibility with other liquid crystal compounds is good. When compound (1) has the bicycle or a tricycle, the viscosity is small. When compound (1) has the tricycle or a tetracycle, the maximum temperature is high. When compound (1) has the tetracycle, the temperature range of the liquid crystal phase is wide.

The physical properties such as the optical anisotropy and the dielectric anisotropy can be arbitrarily adjusted by suitably selecting the terminal group, the ring and the bonding group in compound (1). An effect of a kind of terminal groups $R^a$ and $R^b$, rings $A^1$, $A^2$ and $A^3$ and bonding groups $Z^1$, $Z^2$, $Z^3$ and $Z^4$ on the physical properties of compound (1) is as described below.

In compound (1), when $R^a$ or $R^b$ is the straight chain, the temperature range of the liquid crystal phase is wide, and the viscosity is small. When $R^a$ or $R^b$ is the branched chain, the compatibility with other liquid crystal compounds is good. The compound in which $R^a$ or $R^b$ is an optically active group is useful as a chiral dopant. A reverse twisted domain to be generated in the device can be prevented by adding the compound to the composition. The compound in which $R^a$ or $R^b$ is not the optically active group is also useful as a component of the composition. When $R^a$ or $R^b$ is alkenyl, the preferred configuration depends on the position of the double bond. An alkenyl compound having the preferred configuration has a high maximum temperature or a wide temperature range of the liquid crystal phase. A detailed description is found in Mol. Cryst. Liq. Cryst., 1985, 131, 109 and Mol. Cryst. Liq. Cryst., 1985, 131, 327.

When ring $A^1$, ring $A^2$ or ring $A^3$ is 1,4-phenylene in which at least one piece of hydrogen may be replaced by fluorine or chlorine, pyridine-2,5-diyl, pyrimidine-2,5-diyl or pyridazine-3,6-diyl, the optical anisotropy is large. When the ring is 1,4-cyclohexylene, 1-cyclohexene-1,4-ylene, 2-cyclohexene-1,4-ylene or 1,3-dioxane-2,5-diyl, the optical anisotropy is small.

When at least two rings are 1,4-cyclohexylene, the maximum temperature is high, the optical anisotropy is small and the viscosity is small. When at least one ring is 1,4-phenylene, the optical anisotropy is comparatively large, and an orientational order parameter is large. When at least two rings are 1,4-phenylene, the optical anisotropy is large, the temperature range of the liquid crystal phase is wide and the maximum temperature is high.

When bonding group $Z^1$, $Z^2$, $Z^3$ or $Z^4$ is a single bond, —CH$_2$O—, —CF$_2$O—, —OCF$_2$—, —CH$_2$CH$_2$—, —CH═CH—, —CF═CF— or —(CH$_2$)$_4$—, the viscosity is small. When the bonding group is a single bond, —OCF$_2$—, —CF$_2$O—, —CH$_2$CH$_2$—, or —CH═CH—, the viscosity is smaller. When the bonding group is —CH═CH—, the temperature range of the liquid crystal phase is wide, and an elastic constant ratio $K_{33}/K_{11}$ ($K_{33}$: a bend elastic constant, $K_{11}$: a splay elastic constant) is large. When the bonding group is —C≡C—, the optical anisotropy is large.

When compound (1) has the bicycle or tricycle, the viscosity is small. When compound (1) has the tetracycle or pentacycle, the maximum temperature is high. As described above, a compound having required physical properties can be obtained by suitably selecting a kind of the terminal group, the ring and the bonding group, and the number of rings. Accordingly, compound (1) is useful as the component of the composition to be used for the device having the mode such as the PC mode, the TN mode, the STN mode, the ECB mode, the OCB mode, the IPS mode and the VA mode.

In formula (1-1), when $L^1$ or $L^2$ is fluorine, chlorine, —CF$_3$ or —CHF$_2$, the compound is preferred. When $L^1$ or $L^2$ is fluorine or chlorine, the compound is further preferred. When $L^1$ and $L^2$ are fluorine, the compound is most preferred.

Preferred examples of compound (1) include compound (1-1) described in item 2. Further preferred examples include the compound represented by the subordinate formula in item 3 or the like. Compound (1) is suitable for the device having the mode such as the VA mode and the PSA mode.

2. Synthesis of Compound (1)

The synthetic method of compound (1) will be described. Compound (1) can be prepared by suitably combining methods in synthetic organic chemistry. A method for introducing an required terminal group, ring or bonding group into a starting material is described in books such as "Organic Syntheses" (John Wiley & Sons, Inc.), "Organic Reactions" (John Wiley & Sons, Inc.), "Comprehensive Organic Synthesis" (Pergamon Press) and "New Experimental Chemistry Course (Shin Jikken Kagaku Koza in Japanese)" (Maruzen Co., Ltd.).

2-1. Formation of Bonding Group Z

With regard to a method of synthesizing bonding groups $Z^1$ to $Z^4$, a scheme is first shown. Next, reactions described in the scheme will be described in methods described in sections (1) to (11). In the schemes, MSG$^1$ (or MSG$^2$) is a monovalent organic group having at least one ring. The monovalent organic groups represented by a plurality of MSG$^1$ (or MSG$^2$) used in the scheme may be identical or different. Compounds (1A) to compound (1J) correspond to compound (1).

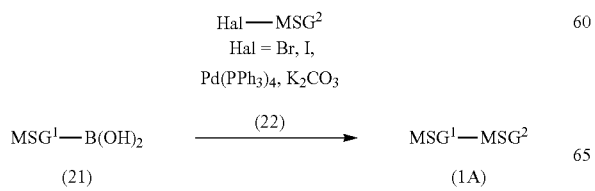

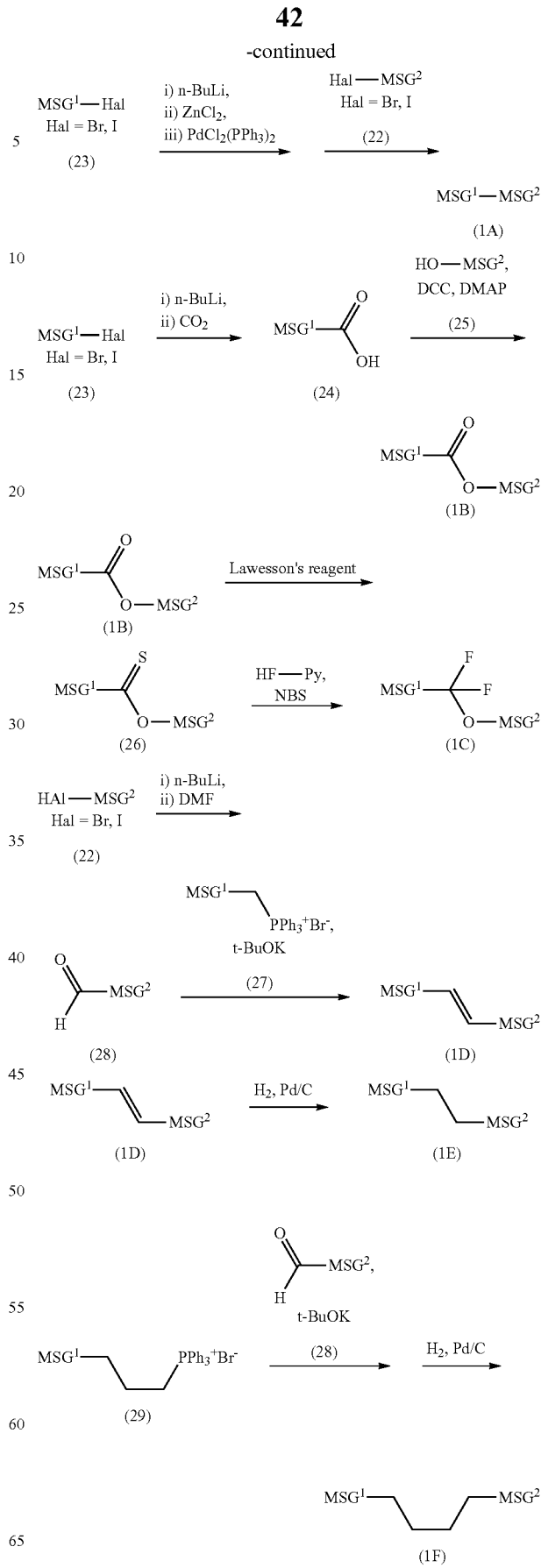

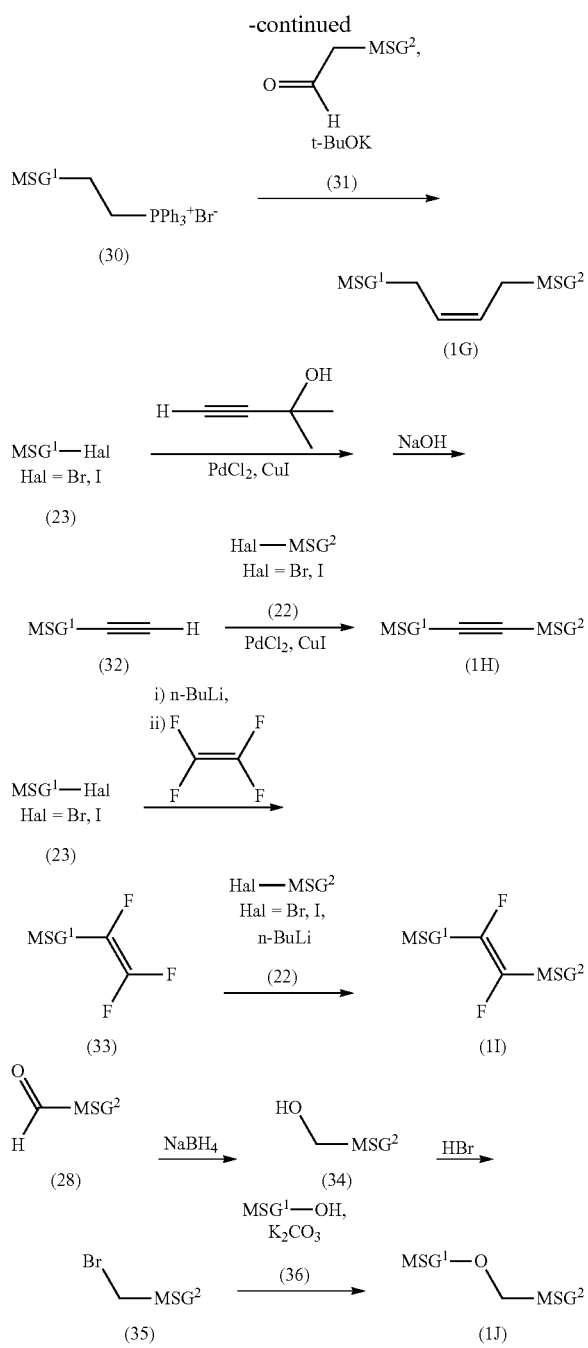

(1) Formation of Single Bond

Compound (1A) is prepared by allowing arylboronic acid (21) prepared by a known method to react with halide (22) in the presence of a catalyst such as carbonate and tetrakis(triphenylphosphine)palladium. Compound (1A) is also prepared by allowing halide (23) prepared by a known method to react with n-butyllithium and subsequently with zinc chloride, and further with halide (22) in the presence of a catalyst such as dichlorobis(triphenylphosphine)palladium.

(2) Formation of —COO—

Carboxylic acid (24) is obtained by allowing halide (23) to react with n-butyllithium and subsequently with carbon dioxide. Compound (1B) is prepared by dehydrating compound (25) prepared by a known method and carboxylic acid (24) in the presence of 1,3-dicyclohexylcarbodiimide (DCC) and 4-dimethylaminopyridine (DMAP).

(3) Formation of —CF$_2$O—

Thionoester (26) is obtained by treating compound (1B) with a thiation reagent such as Lawesson's reagent. Compound (1C) is prepared by fluorinating thionoester (26) with a hydrogen fluoride-pyridine complex and N-bromosuccinimide (NBS). Refer to M. Kuroboshi et al., Chem. Lett., 1992, 827. Compound (1C) is also prepared by fluorinating thionoester (26) with DAST ((diethylamino) sulfur trifluoride). Refer to W. H. Bunnelle et al., J. Org. Chem. 1990, 55, 768. The bonding group can be also formed according to the method described in Peer. Kirsch et al., Angew. Chem. Int. Ed. 2001, 40, 1480.

(4) Formation of —CH═CH—

Aldehyde (28) is obtained by treating halide (22) with n-butyllithium and subsequently allowing the resulting material to react with N,N-dimethylformamide (DMF). Phosphorus ylide is generated by treating phosphonium salt (27) prepared by a known method with a base such as potassium t-butoxide. Compound (1D) is prepared by allowing the phosphorus ylide to react with aldehyde (28). A cis isomer may be generated depending on reaction conditions, and the cis isomer is isomerized into a trans isomer by a known method, when necessary.

(5) Formation of —CH$_2$CH$_2$—

Compound (1E) is prepared by hydrogenating compound (1D) in the presence of a catalyst such as palladium on carbon.

(6) Formation of —(CH$_2$)$_4$—

A compound having —(CH$_2$)$_2$—CH═CH— is obtained by using phosphonium salt (29) in place of phosphonium salt (27) according to the method in section (4). The compound obtained is subjected to catalytic hydrogenation to give compound (1F).

(7) Formation of —CH$_2$CH═CHCH$_2$—

Compound (1G) is prepared, according to the method in section (4), by using phosphonium salt (30) in place of phosphonium salt (27) and aldehyde (31) in place of aldehyde (28). A trans isomer may be generated depending on reaction conditions, and the trans isomer is isomerized into a Cis isomer by a known method, when necessary.

(8) Formation of —C≡C—

Compound (32) is obtained by allowing halide (23) to react with 2-methyl-3-butyn-2-ol in the presence of a catalyst including dichloropalladium and copper halide, and then performing deprotection under basic conditions. Compound (1H) is prepared by allowing compound (32) to react with halide (22) in the presence of the catalyst such as dichloropalladium and copper halide.

(9) Formation of —CF═CF—

Compound (33) is obtained by treating compound (23) with n-butyllithium, and subsequently allowing the resulting material to react with tetrafluoroethylene. Compound (11) is prepared by treating compound (22) with n-butyllithium, and then allowing the resulting material to react with compound (33).

(10) Formation of —OCH$_2$—

Compound (34) is obtained by reducing aldehyde (28) with a reducing agent such as sodium borohydride. Bromide (35) is obtained by brominating compound (34) with hydrobromic acid and so forth. Compound (1J) is prepared by allowing bromide (35) to react with compound (36) in the presence of base such as potassium carbonate.

(11) Formation of —(CH$_2$)$_2$—

A compound having —(CF$_2$)$_2$— is obtained by fluorinating diketone (—COCO—) with sulfur tetrafluoride, in the presence of a hydrogen fluoride catalyst, according to a method described in J. Am. Chem. Soc., 2001, 123, 5414.

2-2. Formation of Rings $A^1$ to $A^3$ and ring N

Next, a method of synthesizing rings $A^1$ to $A^3$ and ring $N^1$ will be described. A starting material is commercially available or a synthetic method thereof is well known among those skilled in the art with regard to a ring such as 1,4-cyclohexylene, 1,3-dioxane-2,5-diyl, 1,4-phenylene, 2-fluoro-1,4-phenylene, 2,3-difluoro-1,4-phenylene, pyridine-2,5-diyl and pyrimidine-2,5-diyl. Thus, compounds (64), (67) and (71) below will be described.

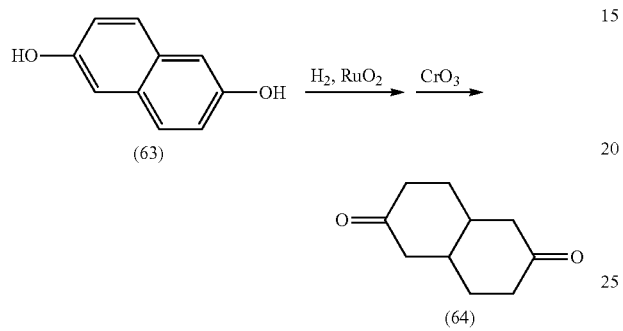

Decahydronaphthalene-2,6-dione (64) is a starting material of a compound having decahydronaphthalene-2,6-diyl. Compound (64) is obtained by reducing diol (63) with hydrogen in the presence of ruthenium oxide, and subsequently oxidizing the resulting material with chromic oxide, according to a method described in JP 2000-239564 A. The compound is converted into compound (1) according to a method generally known for those skilled in the art.

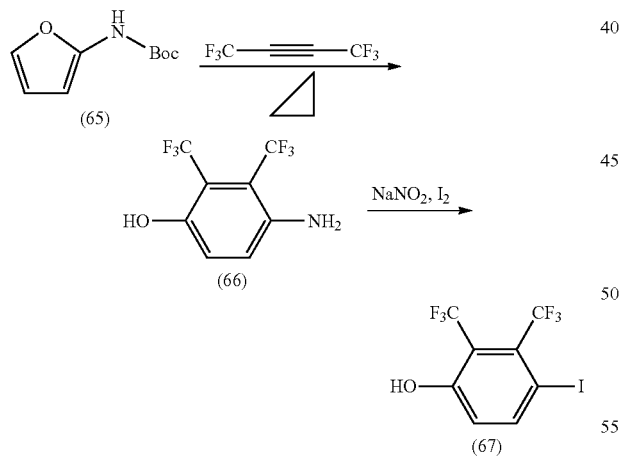

A structural unit of 2,3-(bistrifluoromethyl)phenylene is prepared according to a method described in Org. Lett., 2000, 2 (21), 3345. Aniline (66) is prepared by performing Diels Alder reaction between furan (65) and 1,1,1,4,4,4-hexafluoro-2-butyne at a high temperature. Iodide (67) is obtained by performing a Sandmeyer reaction according to a method described in Org. Synth. Coll., Vol. 2, 1943, and the compound is converted into compound (1) according to a method generally known for those skilled in the art.

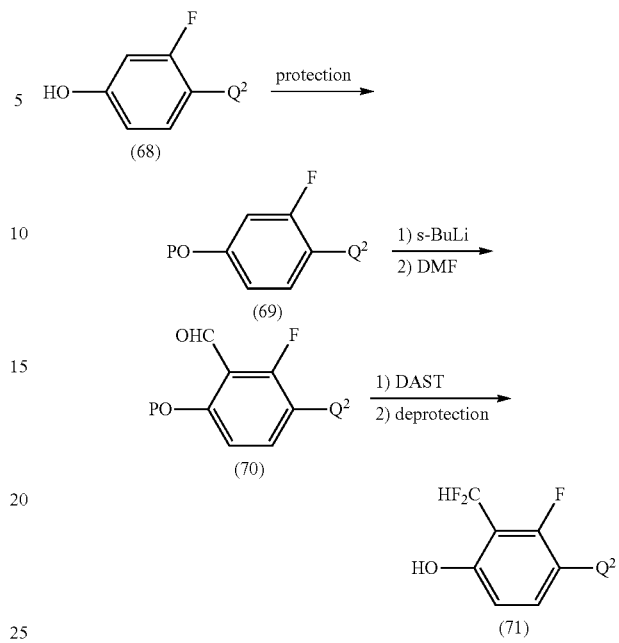

A structural unit of 2-difluoromethyl-3-fluorophenylene is prepared by the method as described below. Compound (69) is obtained by protecting a hydroxy group of compound (68) with a suitable protective group. P means the protective group. Aldehyde (70) is obtained by treating compound (69) with s-butyllithium, and subsequently allowing the resulting material to react with N,N-dimethylformamide (DMF). Phenol (71) is obtained by fluorinating the compound by diethylamino sulfur trifluoride (DAST), and then deprotecting the resulting material. The compound is converted into compound (1) according to a method generally known for those skilled in the art.

2-3. Formation of 3,6-dihydro-2H-pyran ring

A method of preparing the ring will be described by using compounds (1a) and (1b) each having a divalent group represented by formula (pr-1). A compound having a divalent group represented by formula (pr-2) can also be prepared by the method. A synthetic scheme of compound (1a) is as described below.

Compound (s-1) is prepared by a method described in JP 2011-136924 A. Compound (s-2) is obtained by reducing compound (s-1) with a reducing agent such as sodium borohydride. An objective compound (1a) is obtained by halogenating the compound with triphenyl phosphine and carbon tetrahalide, and subsequently treating the resulting material with a dehalogenation agent such as diazabicycloundecen (DBU).

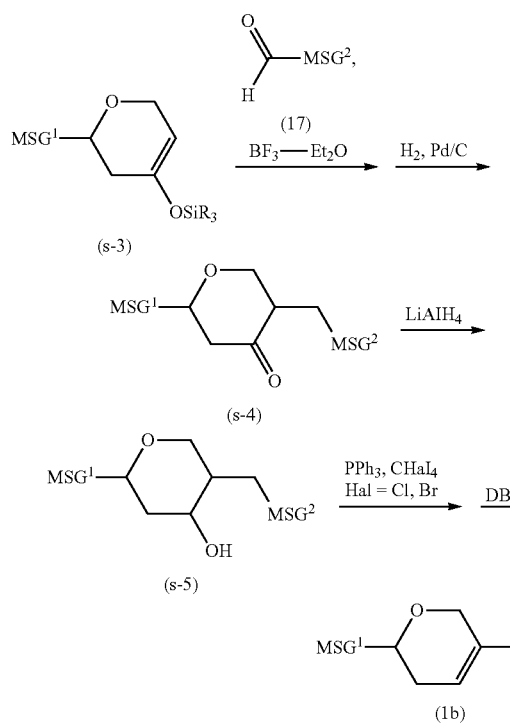

A synthetic scheme of compound (1b) is as described above. Compound (s-4) is obtained by allowing compound (s-3) to react with aldehyde (17) in the presence of Lewis acid such as a boron trifluoride-diethyl ether complex, and subsequently hydrogenating the resulting material. Compound (s-5) is obtained by reducing the compound with a reducing agent such as lithium aluminum hydride or the like. Compound (1b) is obtained by halogenating the compound with triphenyl phosphine and carbon tetrahalide, and subsequently by treating the resulting material with a dehalogenation agent such as diazabicycloundecen (DBU).

3. Liquid Crystal Composition 3-1. Component Compound

A liquid crystal composition of the invention is described. The composition contains at least one compound (1) as component (a). The composition may contain two or three or more compounds (1). The component of the composition may be only compound (1). The composition preferably contains at least one compound (1) in the range of approximately 1 to approximately 99% by weight in order to develop good physical properties. In the composition having the negative dielectric anisotropy, a preferred content of compound (1) is in the range of approximately 5 to approximately 60% by weight. In the composition having the positive dielectric anisotropy, a preferred content of compound (1) is approximately 30% by weight or less.

TABLE 1

| Component compounds in composition | | |
|---|---|---|
| Component | Component compound | Dielectric anisotropy |
| Component (a) | Compound (1) | Negatively large |
| Component (b) | Compound (2) to compound (4) | Small |
| Component (c) | Compound (5) to compound (11) | Negatively large |
| Component (d) | Compound (12) to compound (14) | Positively large |
| Component (e) | Compound (15) | Positively large |

The composition contains compound (1) as component (a). The composition preferably further contains a liquid crystal compound selected from components (b) to (e) described in Table 1. Upon preparing the composition, components (b) to (e) are preferably selected in taking into account the positive or negative dielectric anisotropy and a value thereof. The composition may contain a liquid crystal compound different from compounds (1) to (15). Meanwhile, the composition needs not contain such a liquid crystal compound.

Component (b) is a compound in which two terminal groups are alkyl or the like. Preferred examples of component (b) include compounds (2-1) to (2-11), compounds (3-1) to (3-19) and compounds (4-1) to (4-7). In the compounds, $R^{11}$ and $R^{12}$ are independently alkyl having 1 to 10 carbons or alkenyl having 2 to 10 carbons, and in the alkyl and the alkenyl, at least one piece of —$CH_2$— may be replaced by —O—, and in the groups, at least one piece of hydrogen may be replaced by fluorine.

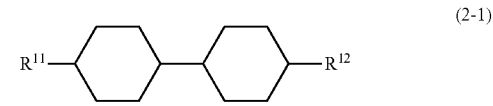
(2-1)

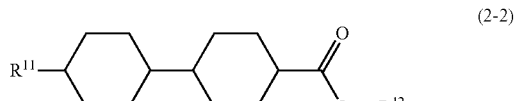
(2-2)

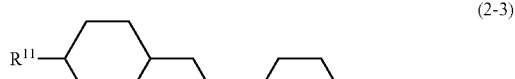
(2-3)

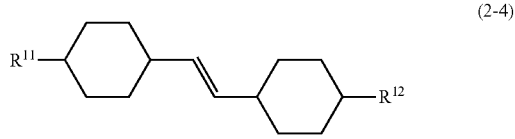
(2-4)

(2-5)

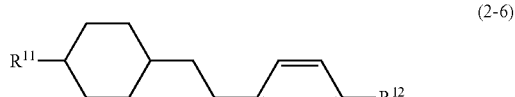
(2-6)

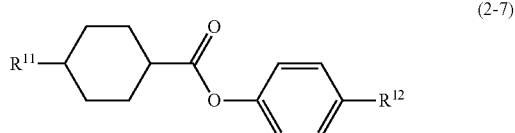
(2-7)

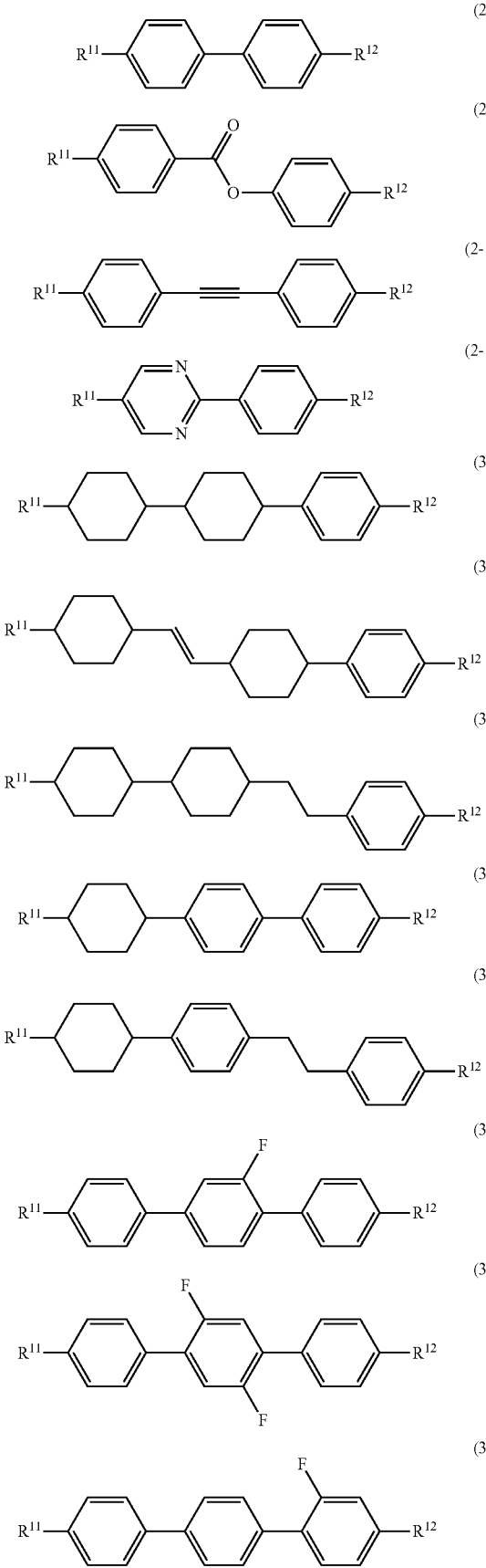
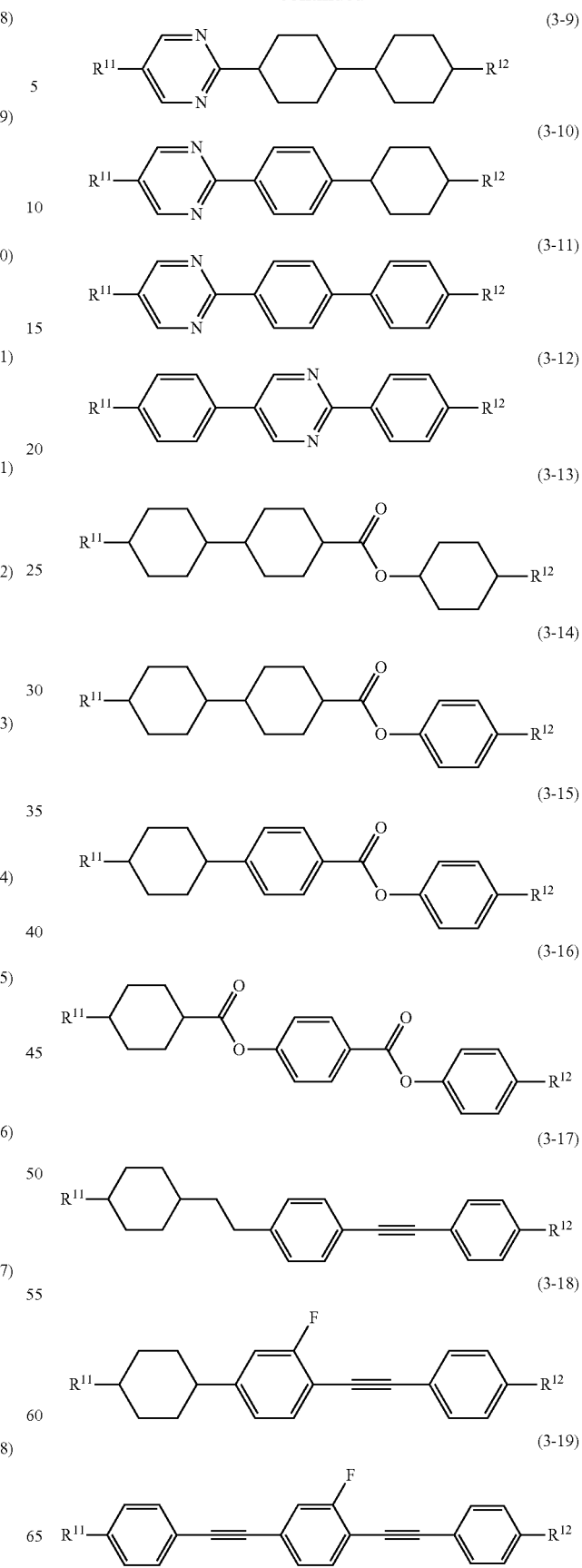

(4-1)
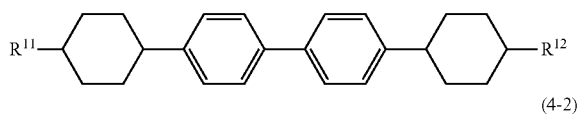

(4-2)
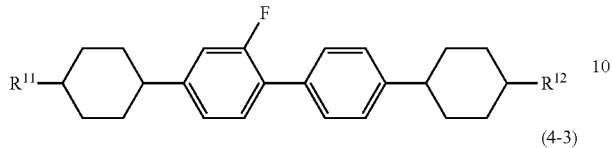

(4-3)
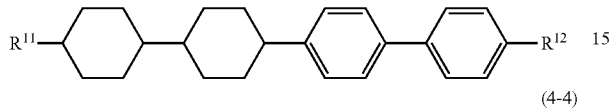

(4-4)
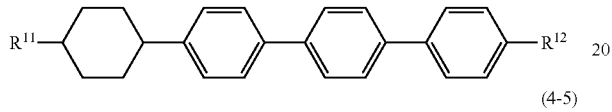

(4-5)
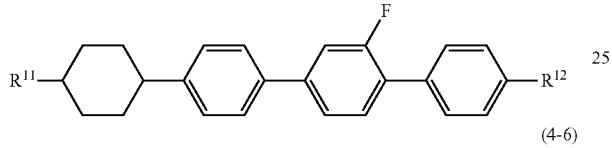

(4-6)
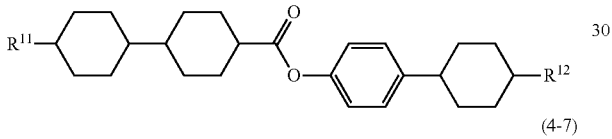

(4-7)
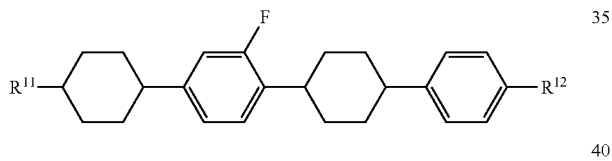

Component (b) has a small dielectric anisotropy. Component (b) is close to neutrality. Containing of compound (2) is effective in decreasing the viscosity or adjusting the optical anisotropy. Containing of compounds (3) and (4) is effective in extending the temperature range of the nematic phase by increasing the maximum temperature, or in adjusting the optical anisotropy.

As a content of component (b) is increased, the viscosity of the composition becomes smaller. As the content of component (b) is increased, the dielectric anisotropy becomes smaller. Thus, as long as a desired value of a threshold voltage of the device is met, the content is preferably as large as possible. When a composition for the IPS mode, the VA mode or the like is prepared, the content of component (b) is preferably approximately 30% by weight or more, and further preferably approximately 40% by weight or more, based on the weight of the liquid crystal composition.

Component (c) includes compounds (5) to (11). The compounds have phenylene in which two pieces of hydrogen in lateral positions are replaced by two pieces of halogen, such as 2,3-difluoro-1,4-phenylene. Preferred examples of component (c) include compounds (5-1) to (5-8), compounds (6-1) to (6-17), compound (7-1), compounds (8-1) to (8-3), compounds (9-1) to (9-11), compound (10-1) to (10-3) and compounds (11-1) to (11-3). In the compounds, $R^{13}$, $R^{14}$ and $R^{15}$ are independently alkyl having 1 to 10 carbons or alkenyl having 2 to 10 carbons, and in the alkyl and the alkenyl, at least one piece of —CH$_2$— may be replaced by —O—, and in the groups, at least one piece of hydrogen may be replaced by fluorine, and $R^{15}$ may be hydrogen or fluorine.

(5-1)
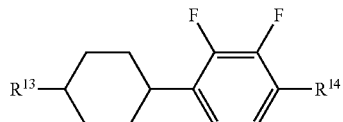

(5-2)
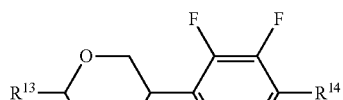

(5-3)
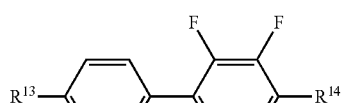

(5-4)
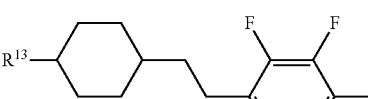

(5-5)
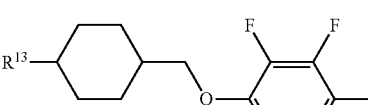

(5-6)
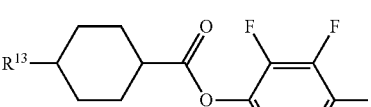

(5-7)
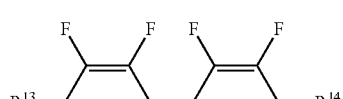

(5-8)
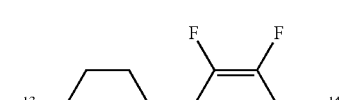

(6-1)
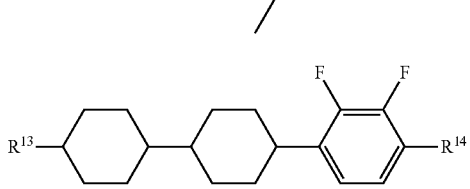

(6-2)
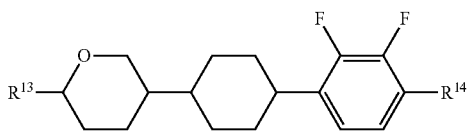

(6-3) 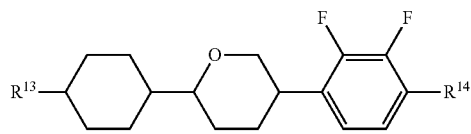
(6-4) 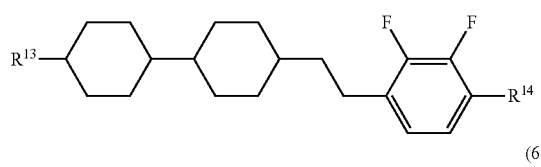
(6-5) 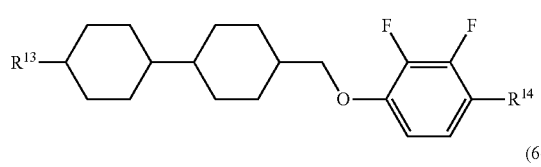
(6-6) 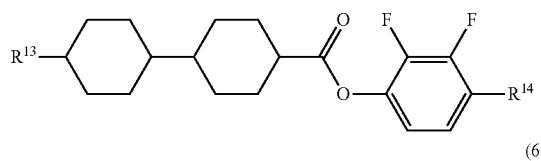
(6-7) 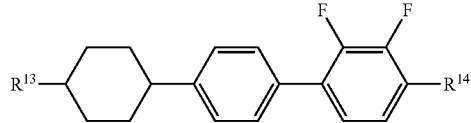
(6-8) 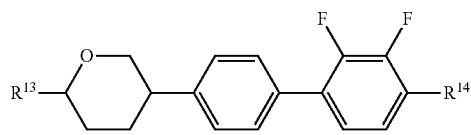
(6-9) 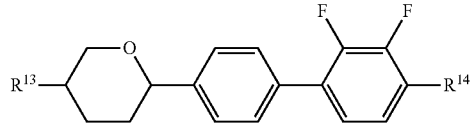
(6-10) 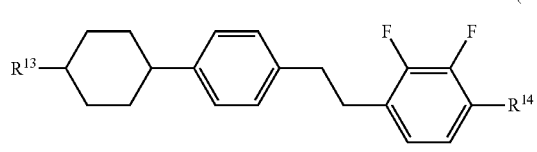
(6-11) 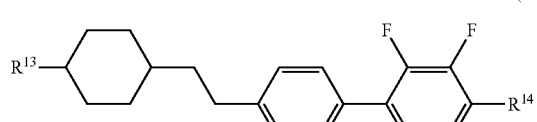
(6-12) 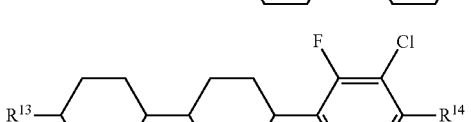
(6-13) 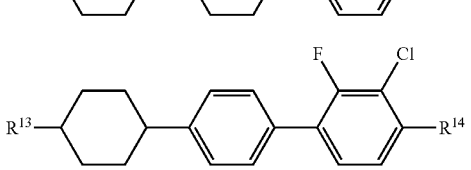
(6-14) 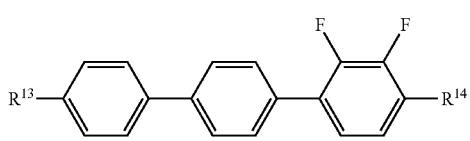
(6-15) 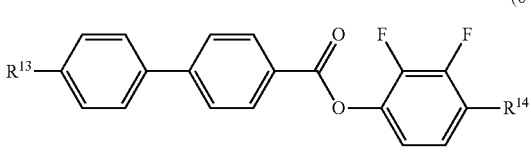
(6-16) 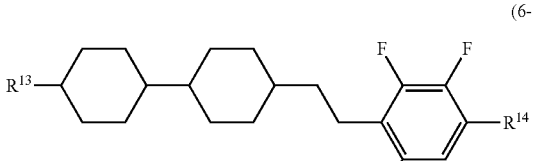
(6-17) 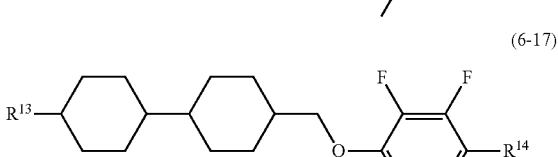
(7-1) 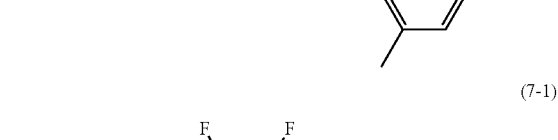
(8-1) 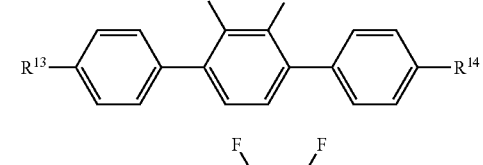
(8-2) 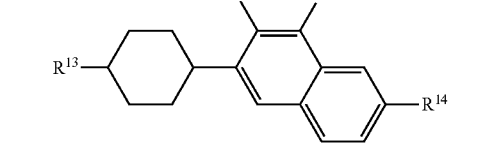
(8-3) 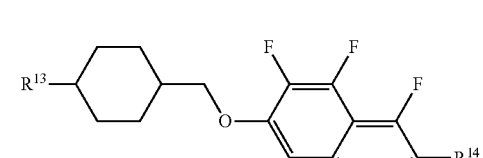
(9-1) 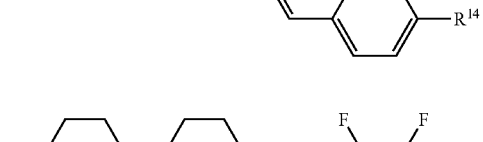

(9-2) 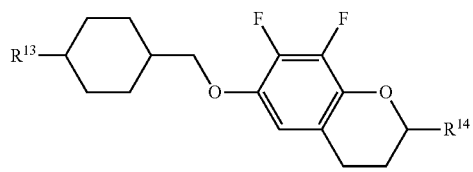
(9-3) 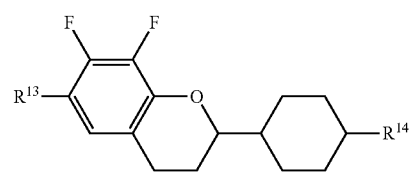
(9-4) 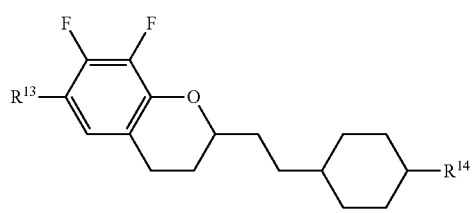
(9-5) 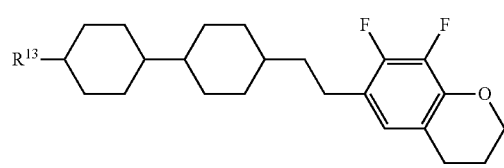
(9-6) 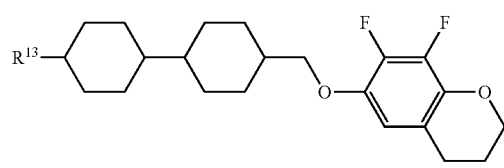
(9-7) 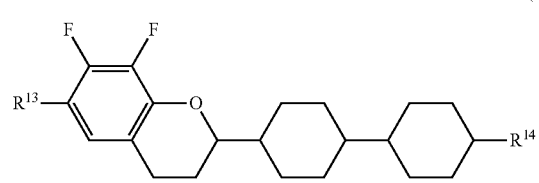
(9-8) 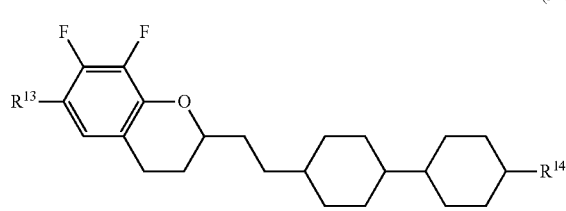
(9-9) 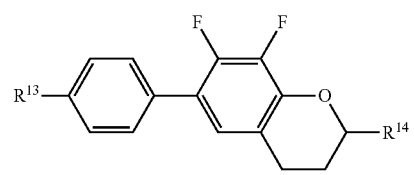
(9-10) 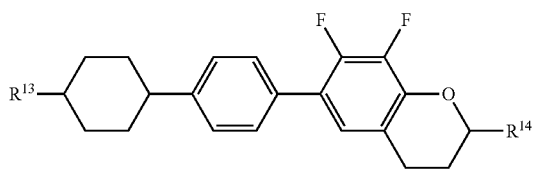
(9-11) 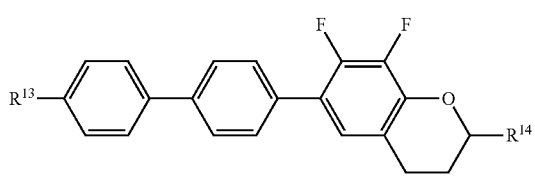
(10-1) 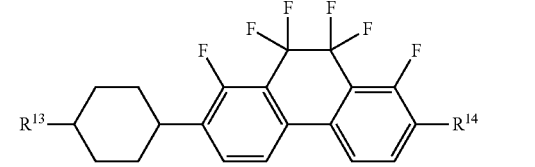
(10-2) 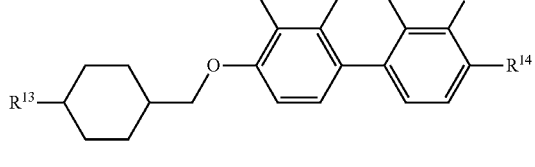
(10-3) 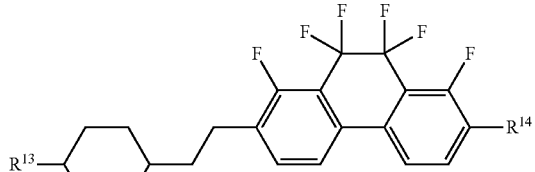
(11-1) 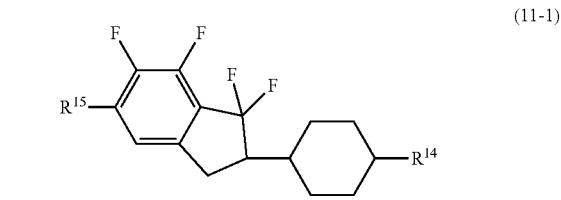
(11-2)

(11-3)

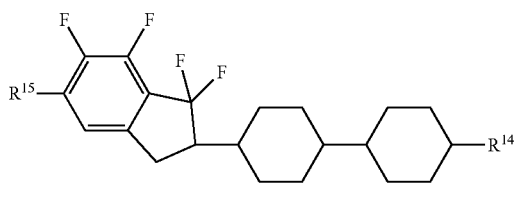

Component (c) has the negatively large dielectric anisotropy. Component (c) is used when a composition for the IPS mode, the VA mode, the PSA mode or the like is prepared. As a content of component (c) is increased, the dielectric anisotropy of the composition becomes negatively larger. As the content of component (c) is increased, the viscosity of the composition becomes larger. Thus, as long as a desired value of the threshold voltage of the device is met, the content is preferably as small as possible. The content is preferably approximately 40% by weight or more to allow sufficient voltage driving in taking into account the dielectric anisotropy being approximately −5.

In component (c), compound (5) is a bicyclic compound, and containing thereof is effective in decreasing the viscosity, adjusting the optical anisotropy or increasing the dielectric anisotropy. Compound (5) and compound (6) are a tricyclic compound, and therefore containing thereof is effective in increasing the maximum temperature, the optical anisotropy or the dielectric anisotropy. Containing of compounds (8) to (11) is effective in increasing the dielectric anisotropy.

When the composition for the IPS mode, the VA mode or the PSA mode is prepared, the content of component (c) is preferably approximately 40% by weight or more, and further preferably in the range of approximately 50 to approximately 95% by weight, based on the weight of the composition. When component (c) is added to a composition having the positive dielectric anisotropy, a preferred content of component (c) is approximately 30% by weight or less. The elastic constant of the composition and a voltage-transmittance curve of the device can be adjusted by adding component (c) thereto.

Component (d) is a compound having a halogen-containing or fluorine-containing group at a right terminal. Preferred examples of component (d) include compounds (12-1) to (12-16), compounds (13-1) to (13-113) and compounds (14-1) to (14-57). In the compounds, $R^{16}$ is alkyl having 1 to 10 carbons or alkenyl having 2 to 10 carbons, and in the alkyl and the alkenyl, at least one piece of —CH$_2$— may be replaced by —O—, and in the groups, at least one piece of hydrogen may be replaced by fluorine. $X^{11}$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$.

(12-1)

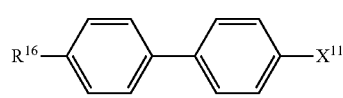

(12-2)

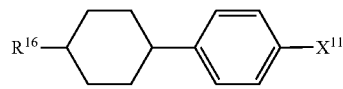

(12-3)

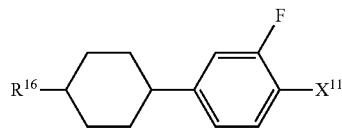

(12-4)

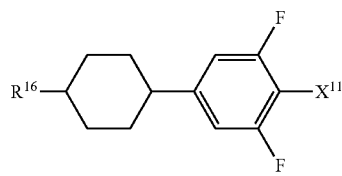

(12-5)

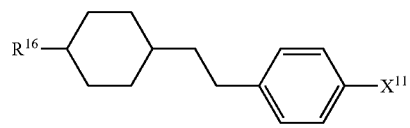

(12-6)

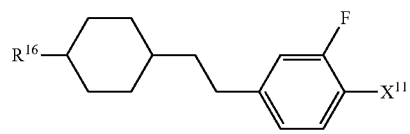

(12-7)

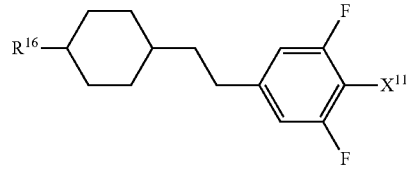

(12-8)

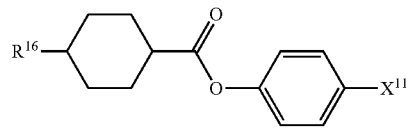

(12-9)

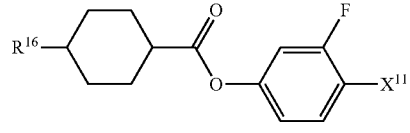

(12-10)

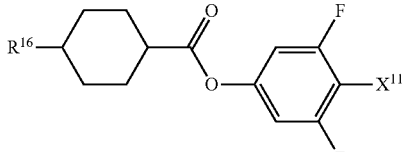

(12-11)

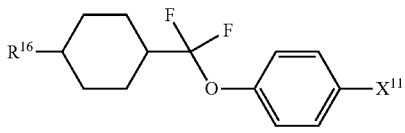

(12-12)

(12-13) 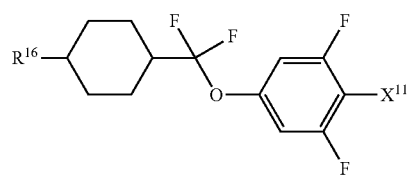
(12-14) 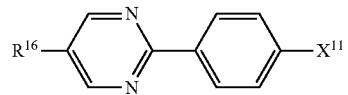
(12-15) 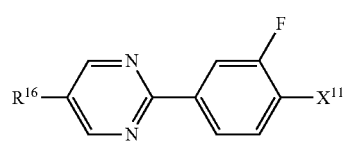
(12-16) 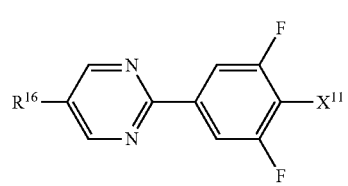
(13-1) 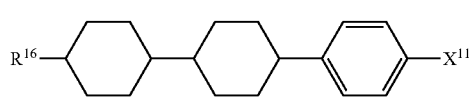
(13-2) 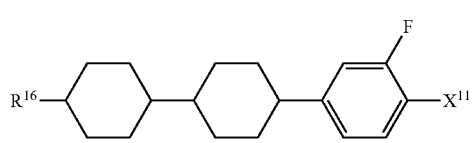
(13-3) 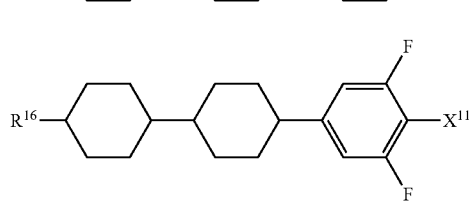
(13-4) 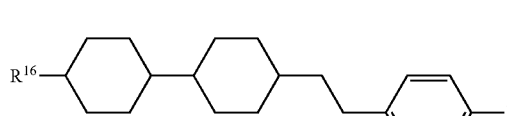
(13-5) 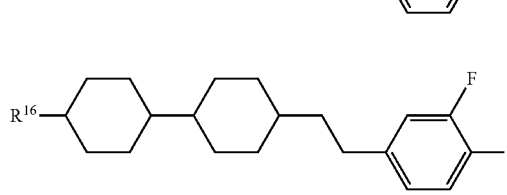
(13-6) 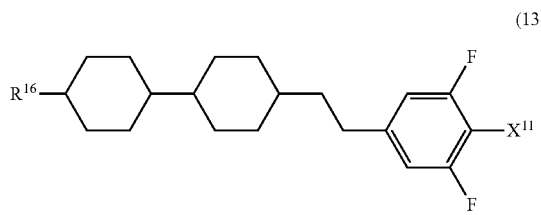
(13-7) 
(13-8) 
(13-9) 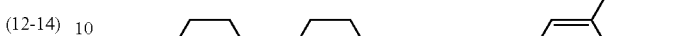
(13-10) 
(13-11) 
(13-12) 
(13-13) 
(13-14) 
(13-15) 

(13-16)
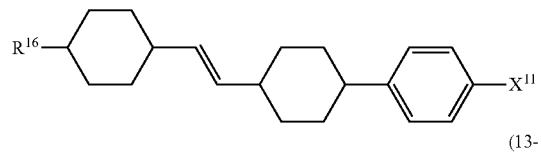
(13-17)
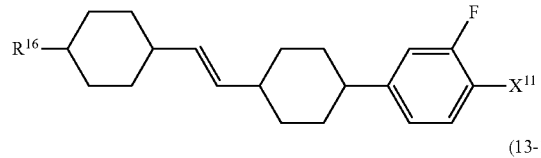
(13-18)
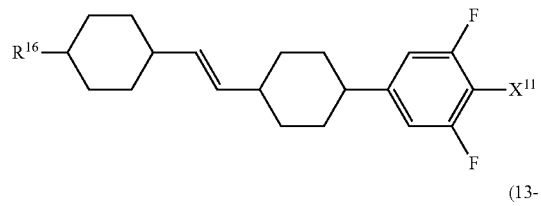
(13-19)
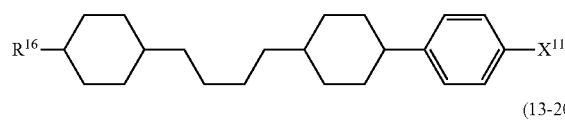
(13-20)
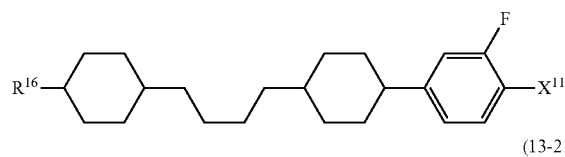
(13-21)
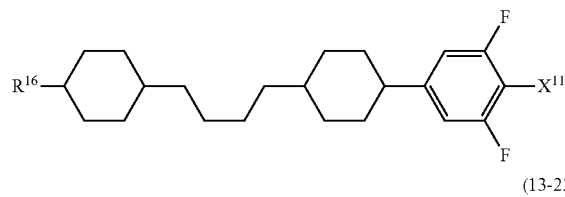
(13-22)
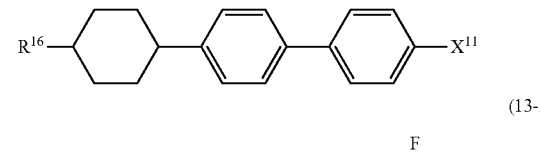
(13-23)
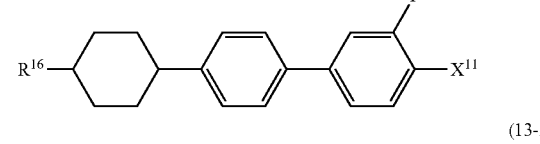
(13-24)
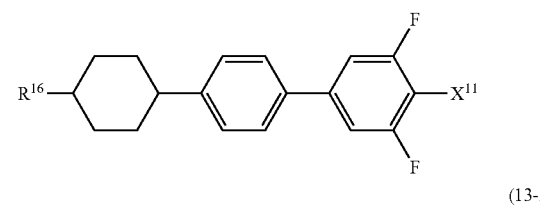
(13-25)
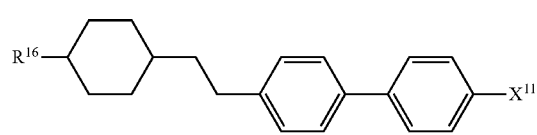
(13-26)
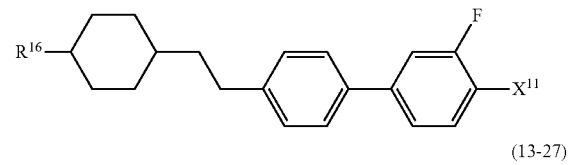
(13-27)
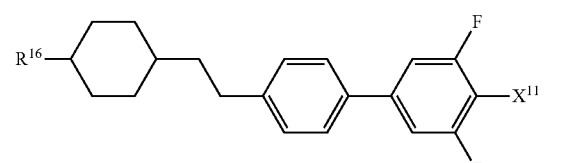
(13-28)
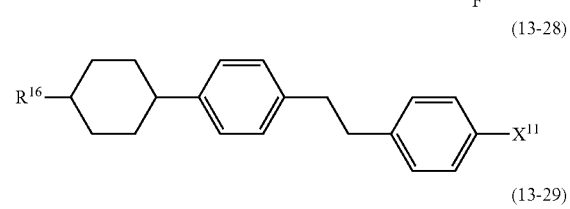
(13-29)
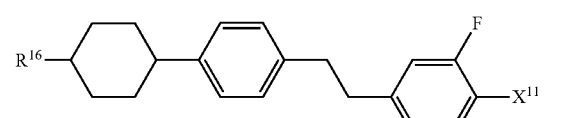
(13-30)
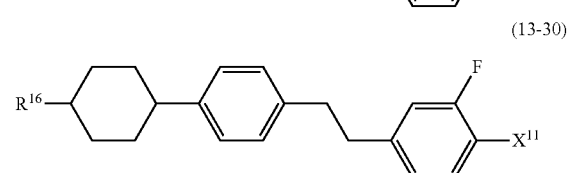
(13-31)
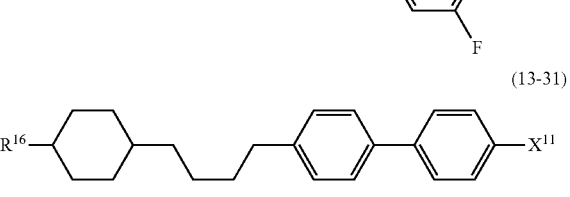
(13-32)
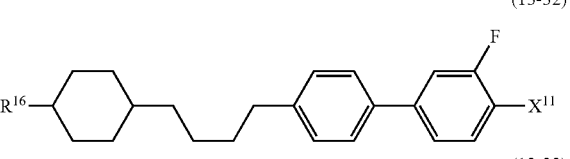
(13-33)
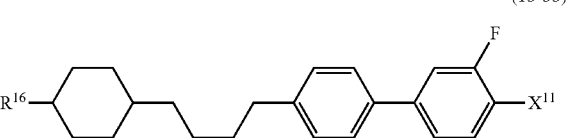
(13-34)
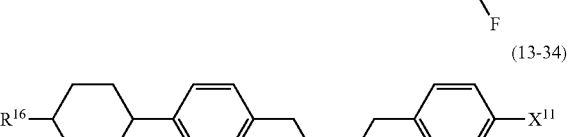
(13-35)
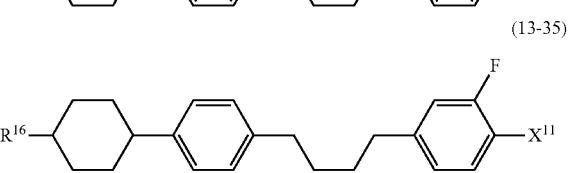

(13-36) 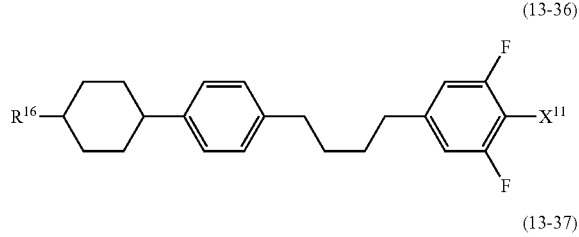
(13-37) 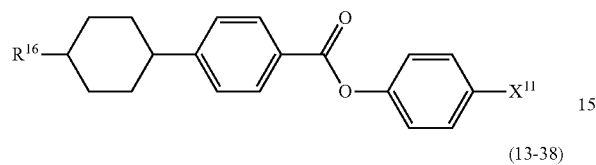
(13-38) 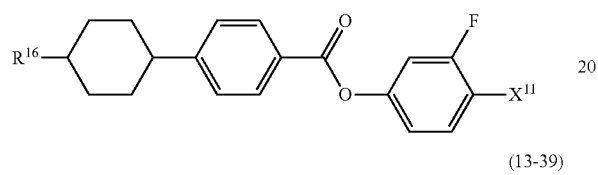
(13-39) 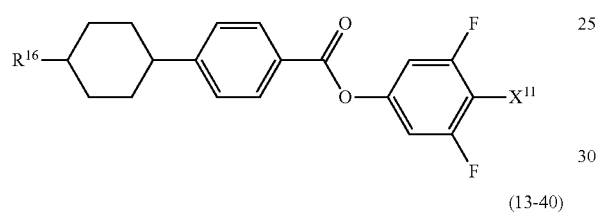
(13-40) 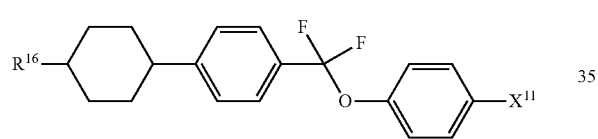
(13-41) 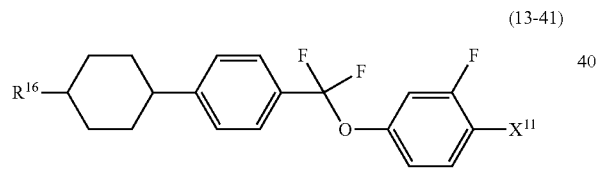
(13-42) 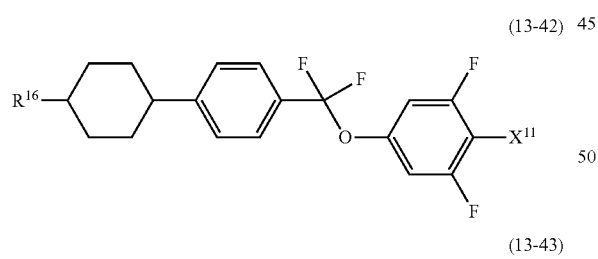
(13-43) 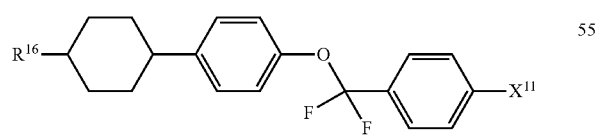
(13-44) 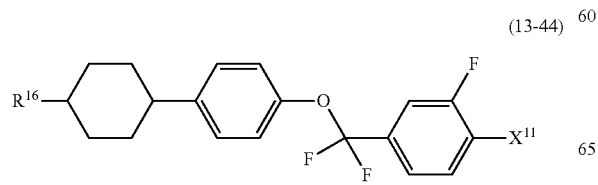
(13-45) 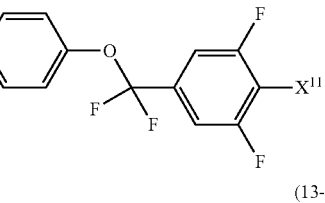
(13-46) 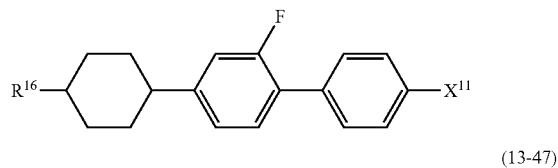
(13-47) 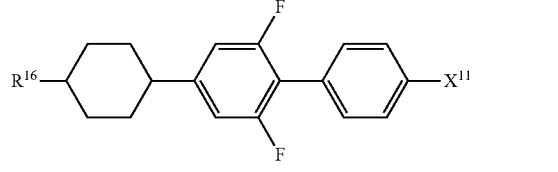
(13-48) 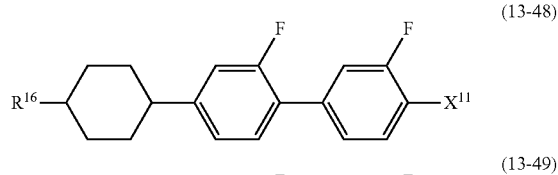
(13-49) 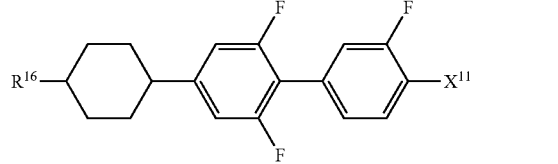
(13-50) 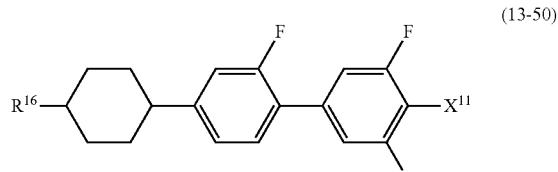
(13-51) 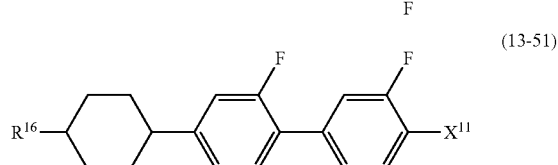
(13-52) 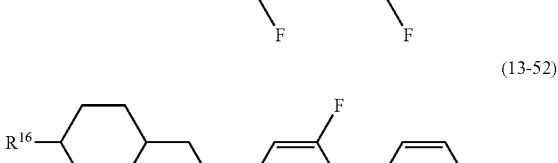
(13-53) 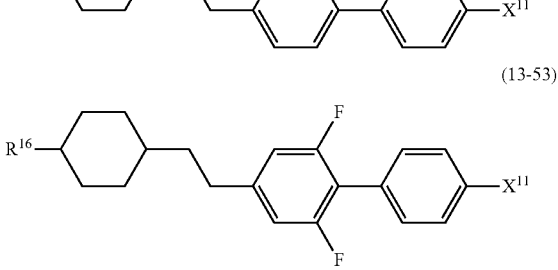

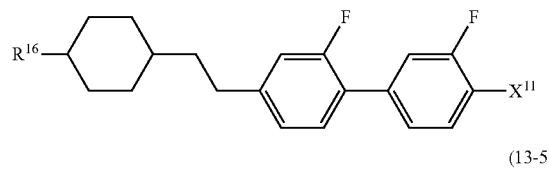
(13-54)
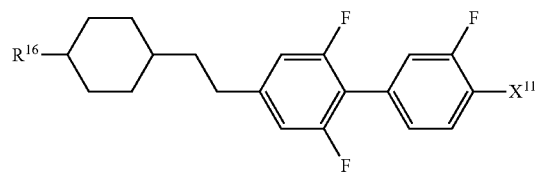
(13-55)
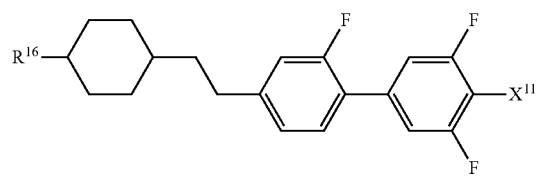
(13-56)
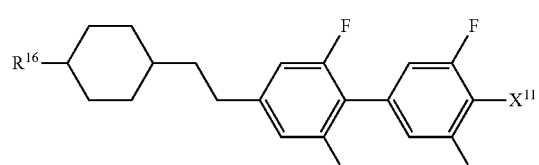
(13-57)
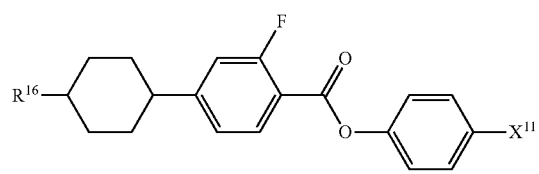
(13-58)
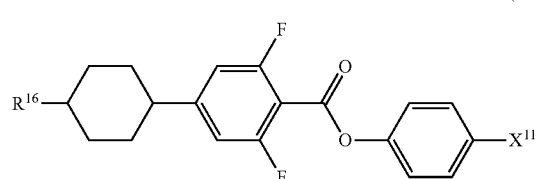
(13-59)
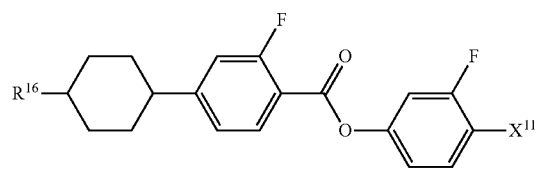
(13-60)
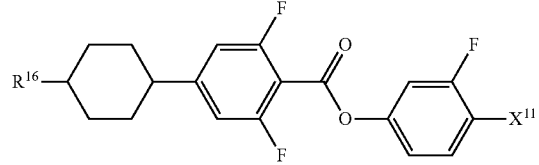
(13-61)
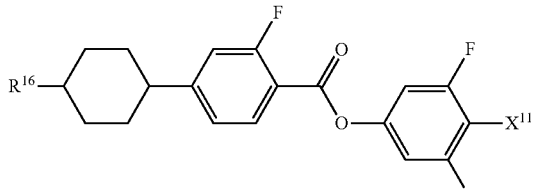
(13-62)
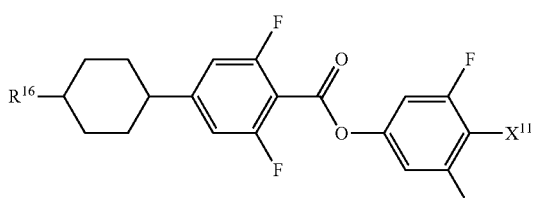
(13-63)
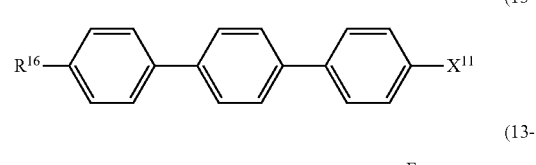
(13-64)
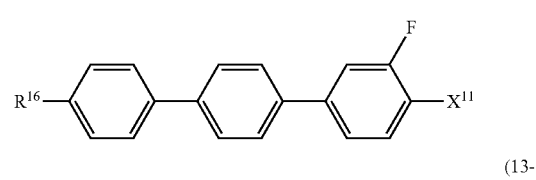
(13-65)
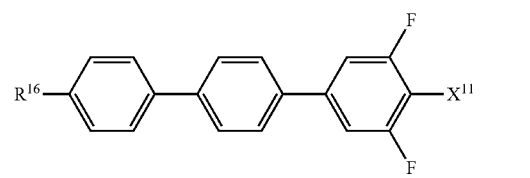
(13-66)
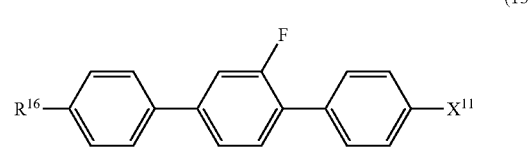
(13-67)
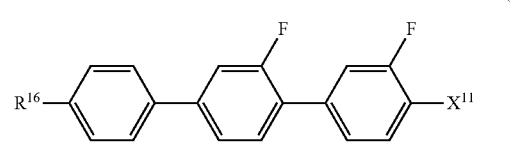
(13-68)
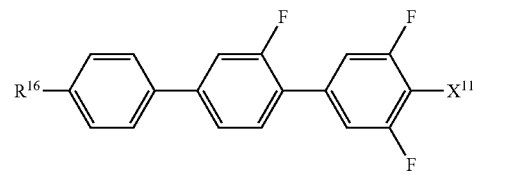
(13-69)

(13-70) 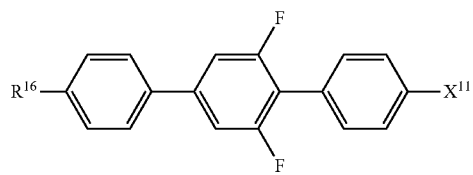
(13-71) 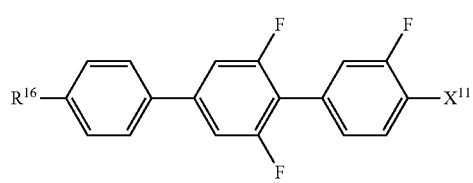
(13-72) 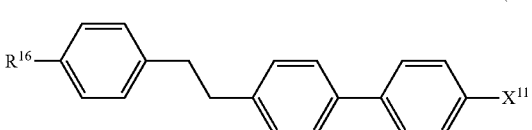
(13-73) 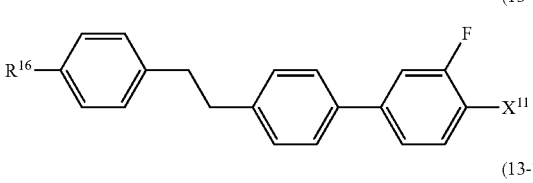
(13-74) 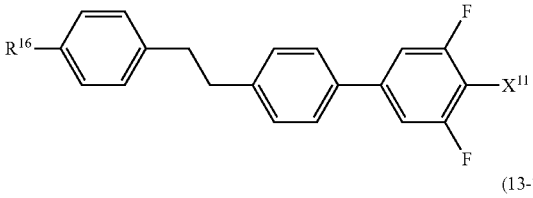
(13-75) 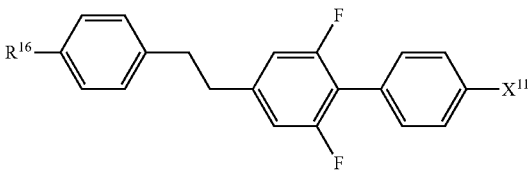
(13-76) 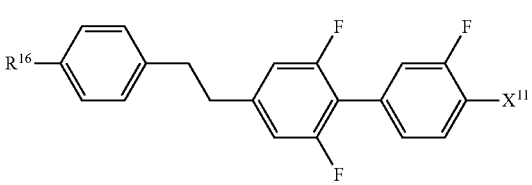
(13-77) 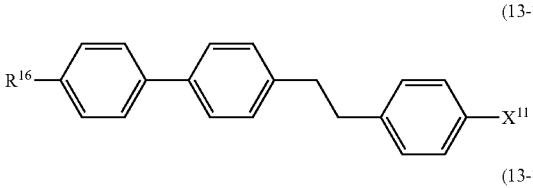
(13-78) 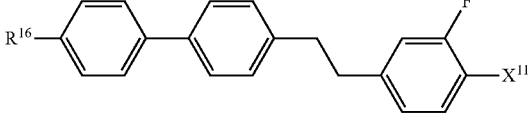
(13-79) 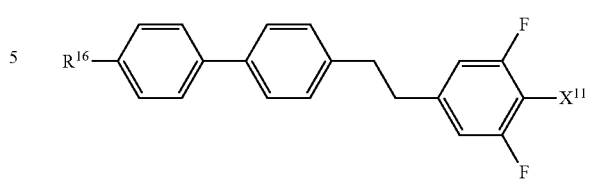
(13-80) 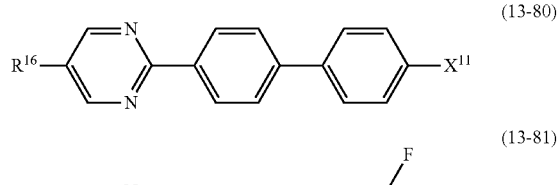
(13-81) 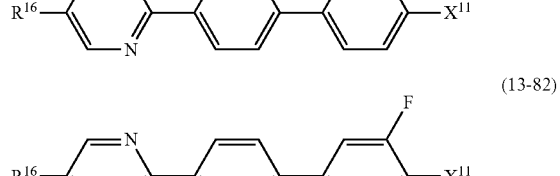
(13-82) 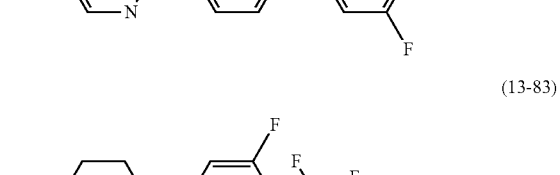
(13-83) 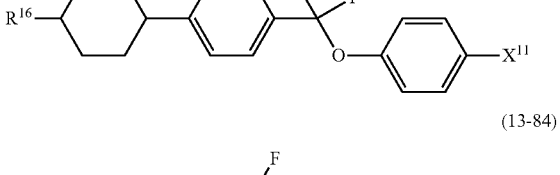
(13-84) 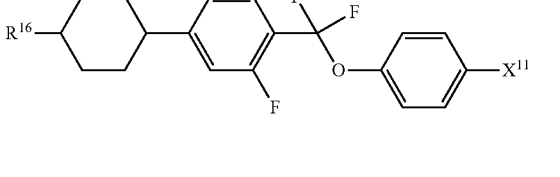
(13-85) 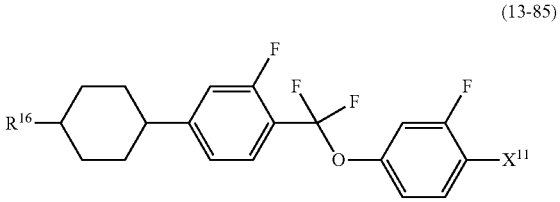
(13-86) 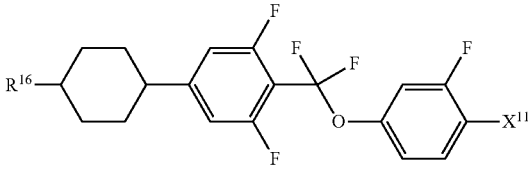

(13-87) 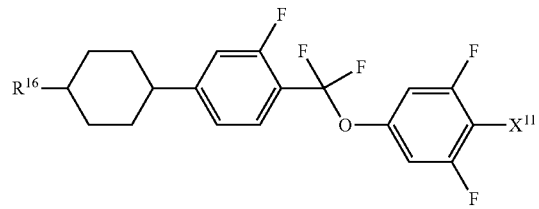
(13-88) 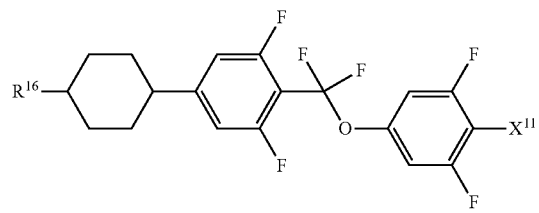
(13-89) 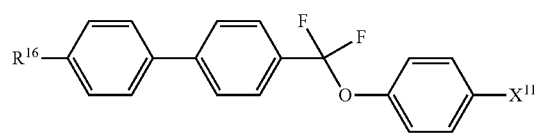
(13-90) 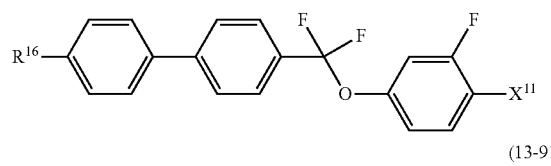
(13-91) 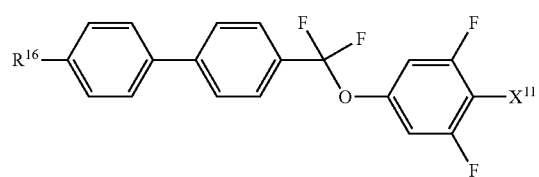
(13-92) 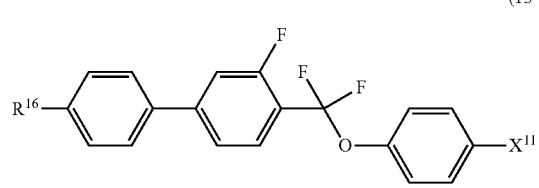
(13-93) 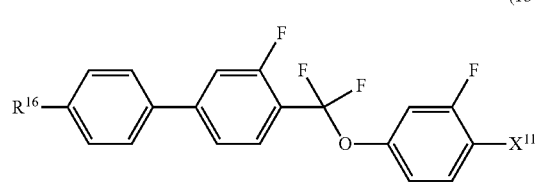
(13-94) 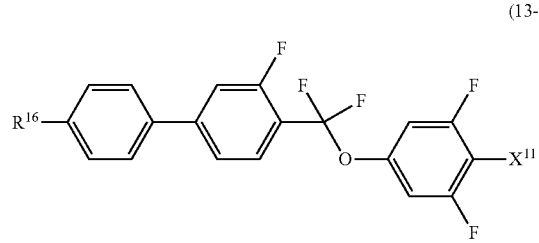
(13-95) 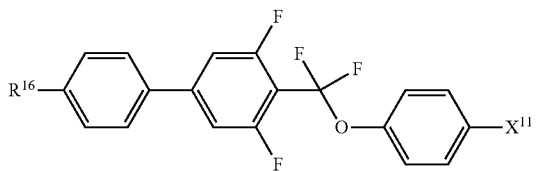
(13-96) 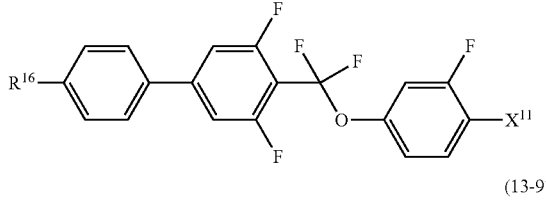
(13-97) 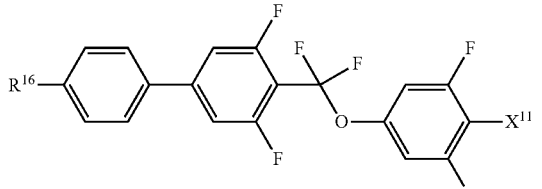
(13-98) 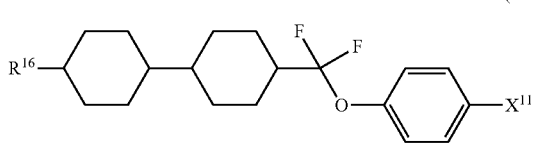
(13-99) 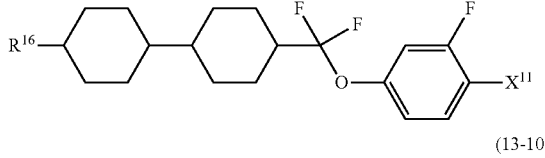
(13-100) 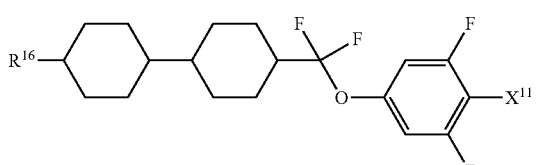
(13-101) 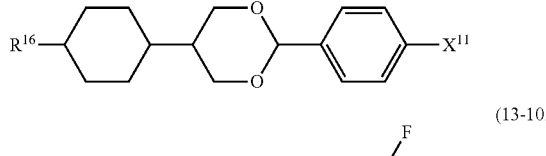
(13-102) 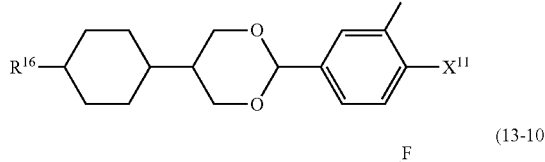
(13-103) 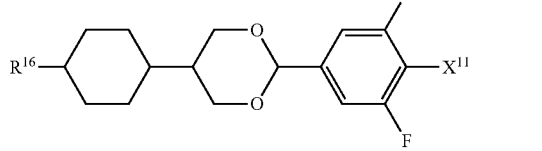

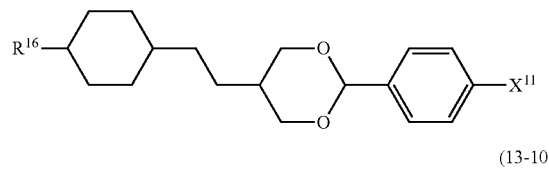 (13-104)
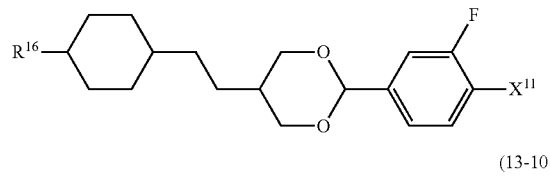 (13-105)
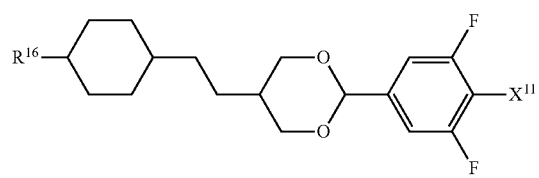 (13-106)
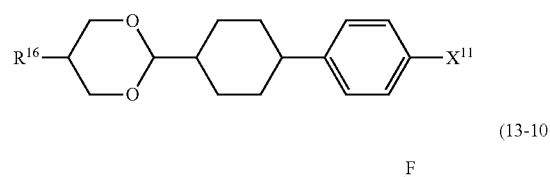 (13-107)
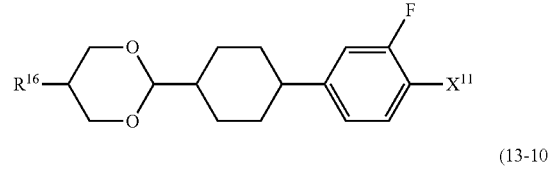 (13-108)
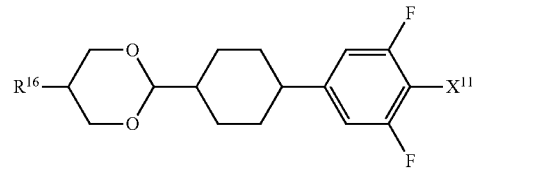 (13-109)
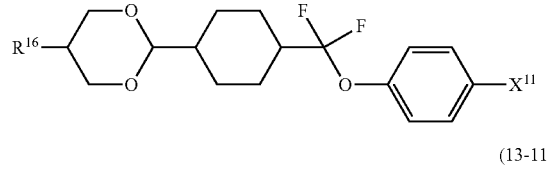 (13-110)
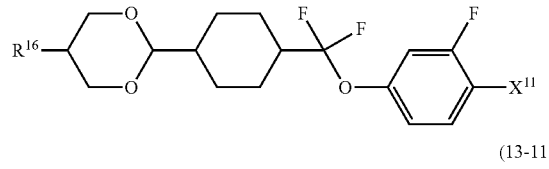 (13-111)
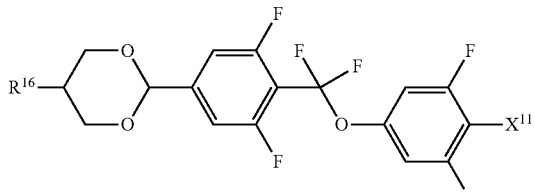 (13-112)
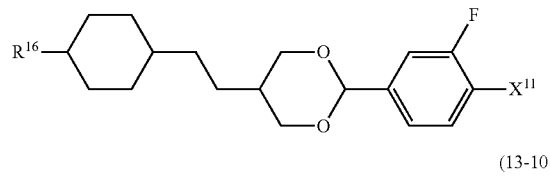 (13-113)
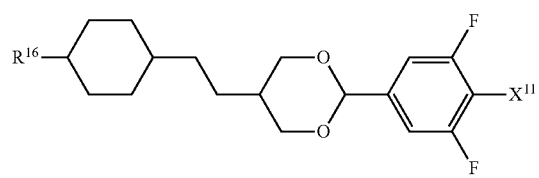 (14-1)
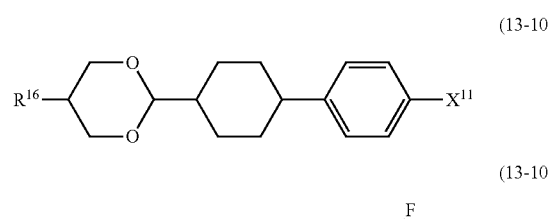 (14-2)
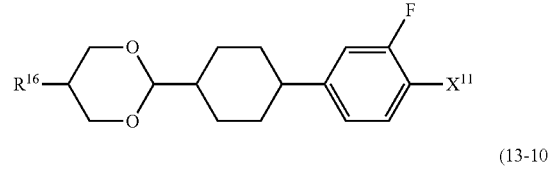 (14-3)
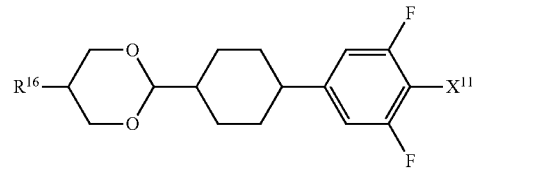 (14-4)
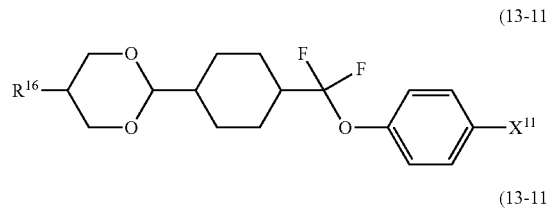 (14-5)
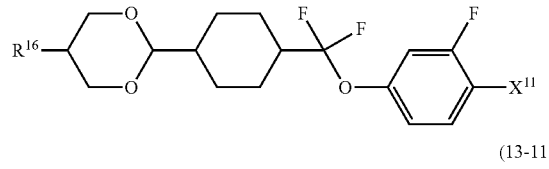 (14-6)
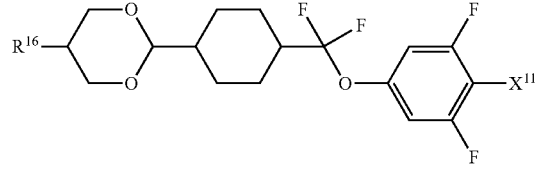 (14-7)
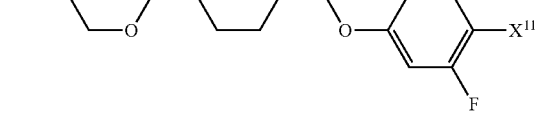 (14-8)
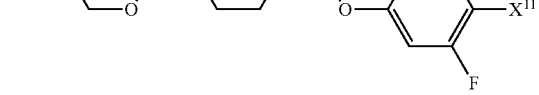

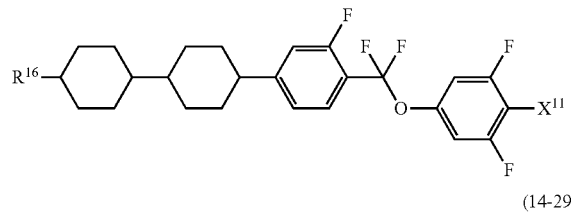
(14-28)
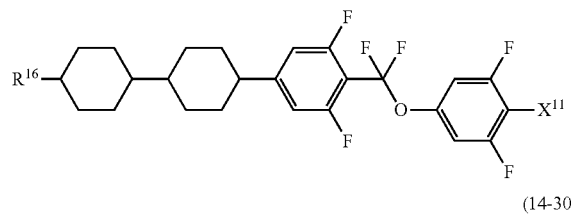
(14-29)
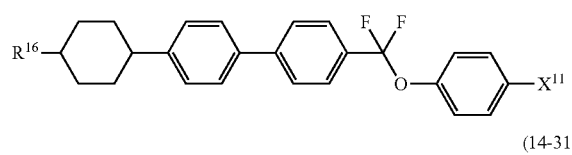
(14-30)
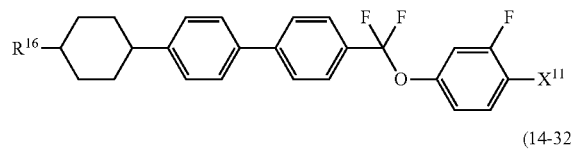
(14-31)
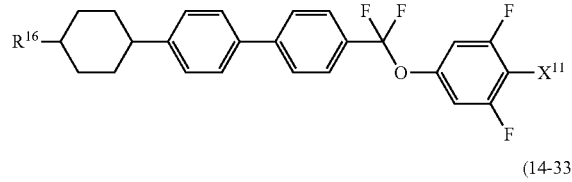
(14-32)
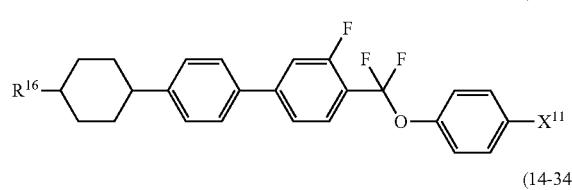
(14-33)
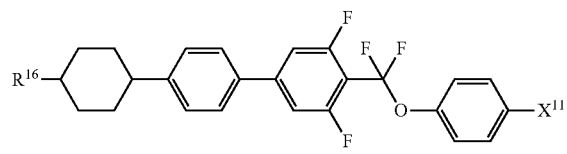
(14-34)
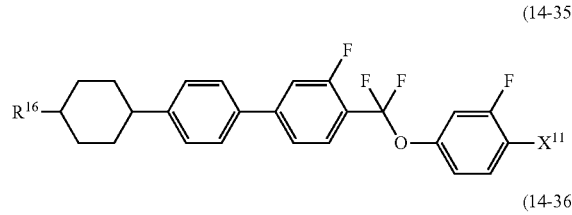
(14-35)
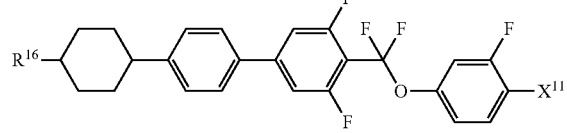
(14-36)
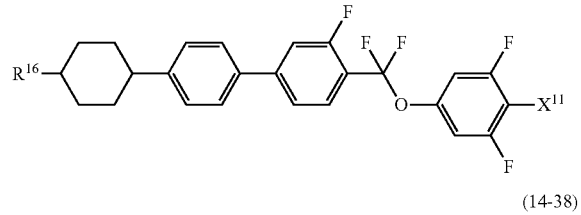
(14-37)
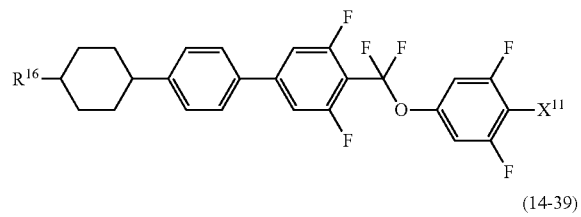
(14-38)
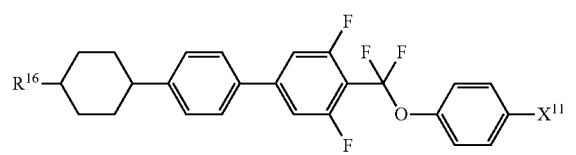
(14-39)
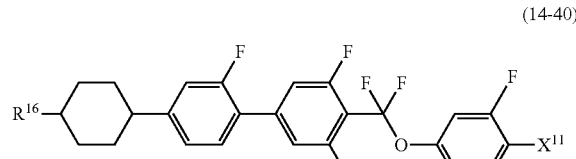
(14-40)
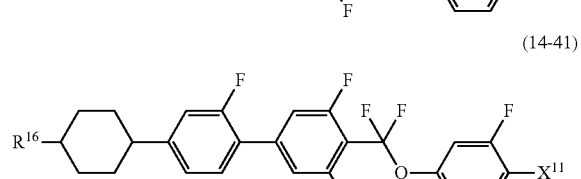
(14-41)
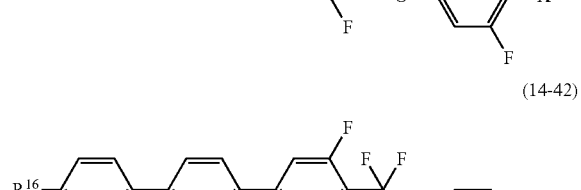
(14-42)
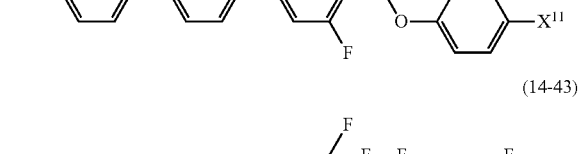
(14-43)
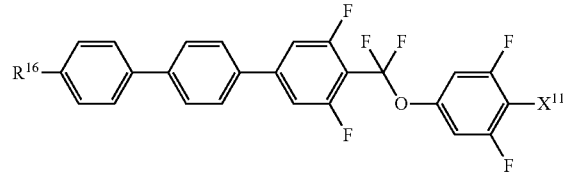
(14-44)

(14-45)
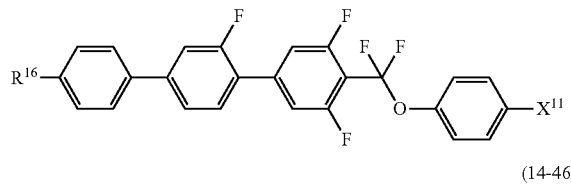

(14-46)
(14-47)
(14-48)
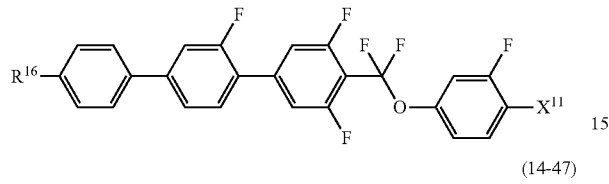

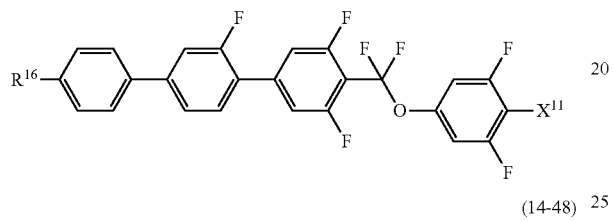

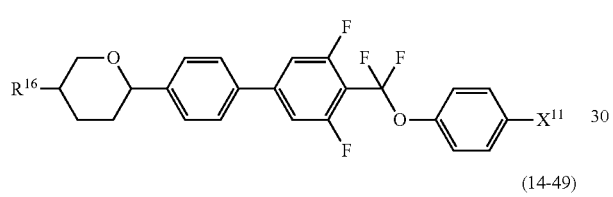

(14-49)
(14-50)
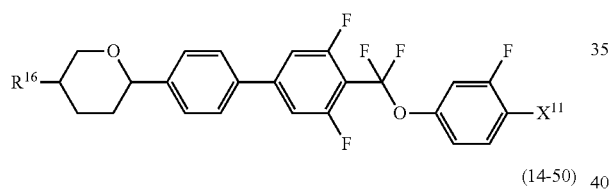

(14-51)
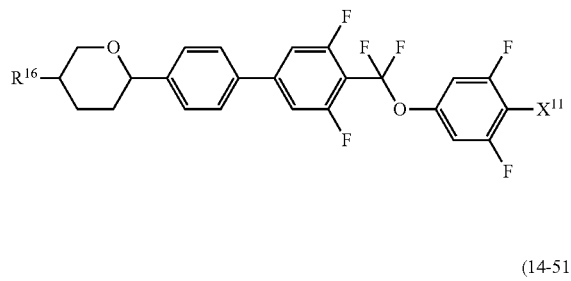

(14-52)
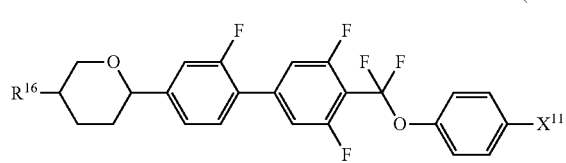

(14-53)
(14-54)
(14-55)
(14-56)
(14-57)
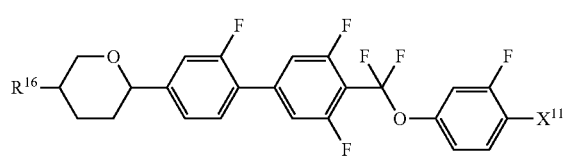

Component (d) has the positive dielectric anisotropy and a superb stability to heat and light, and therefore is used when a composition for the IPS mode, the FFS mode, the OCB mode or the like is prepared. A content of component (d) is suitably in the range of approximately 1 to approximately 99% by weight, preferably in the range of approximately 10 to approximately 97% by weight, and further preferably in the range of approximately 40 to approximately 95% by weight, based on the weight of the composition. When component (d) is added to a composition having the negative dielectric anisotropy, the content of component (d) is preferably approximately 30% by weight or less based on the weight of the composition. The elastic constant of the composition can be adjusted, and the voltage-transmittance curve of the device can be adjusted by adding component (d) thereto.

Component (e) is compound (15) in which a right-terminal group is —C≡N or —C≡C—C≡N. Preferred examples of component (e) include compounds (15-1) to (15-64). In the compounds, $R^{17}$ is alkyl having 1 to 10 carbons or alkenyl having 2 to 10 carbons, and in the alkyl and the alkenyl, at least one piece of —CH$_2$— may be replaced by —O—, and in the groups, at least one piece of hydrogen may be replaced by fluorine. $X^{12}$ is —C≡N or —C≡C—C≡N.

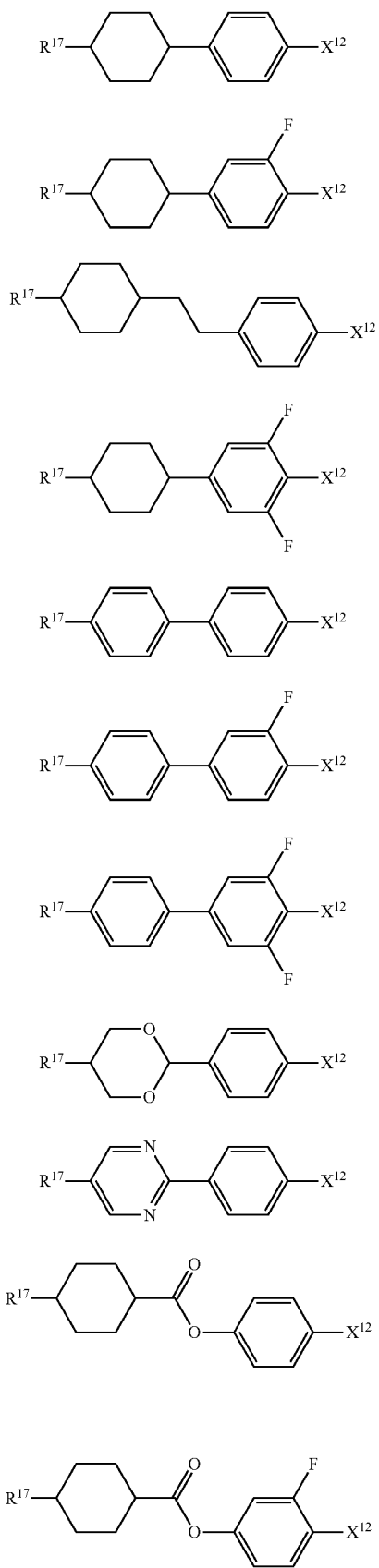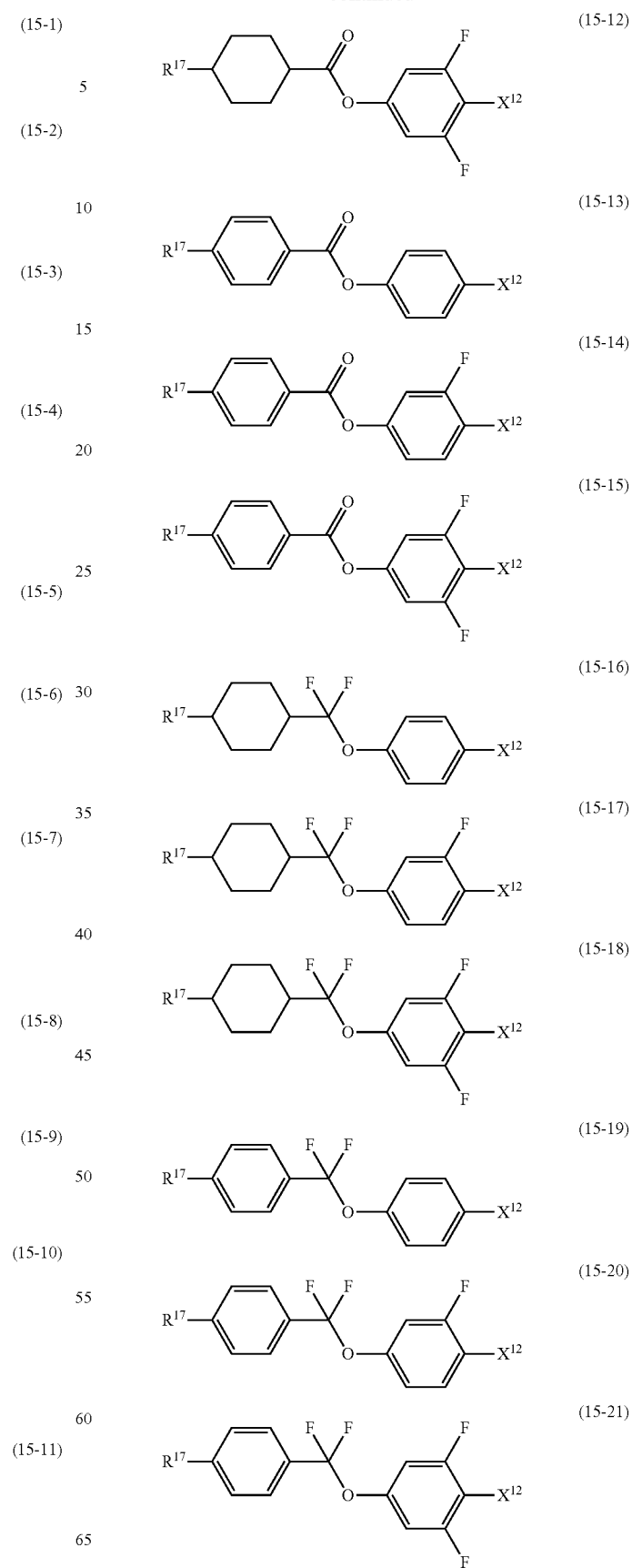

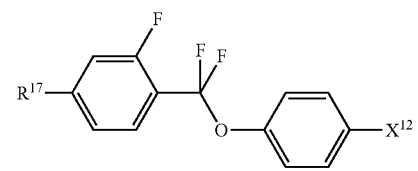 (15-22)
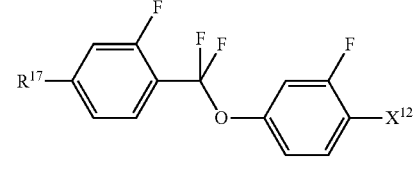 (15-23)
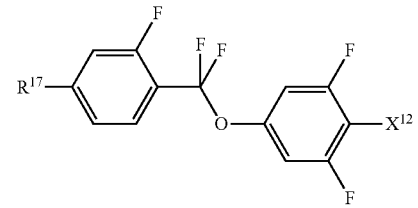 (15-24)
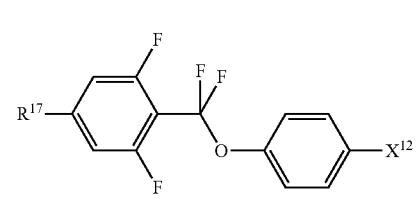 (15-25)
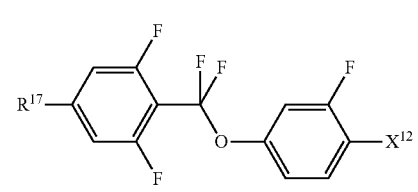 (15-26)
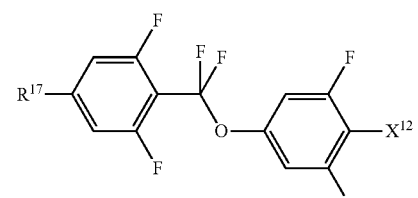 (15-27)
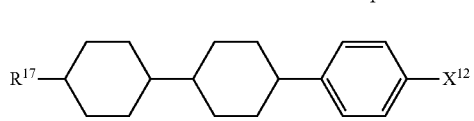 (15-28)
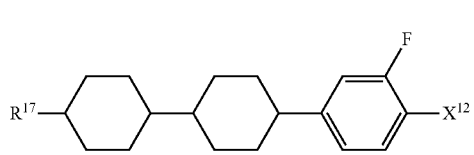 (15-29)
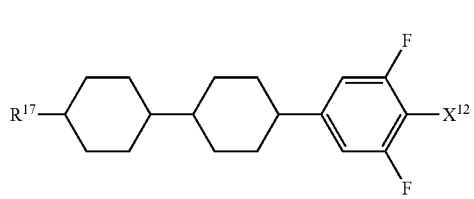 (15-30)
(15-31)
(15-32)
(15-33)
(15-34)
(15-35)
(15-36)
(15-37)
(15-38)
(15-39)
(15-40)

(15-41) 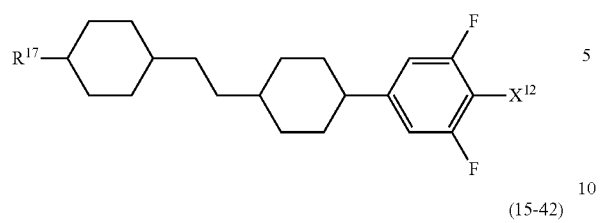
(15-42) 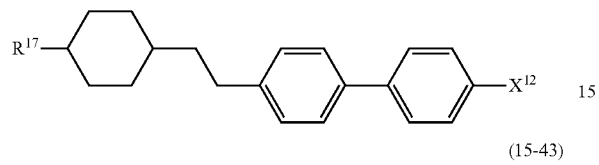
(15-43) 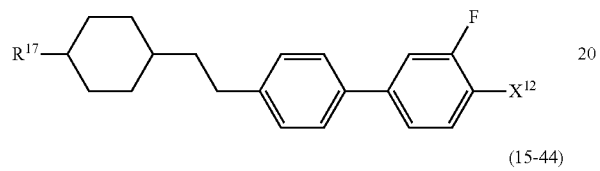
(15-44) 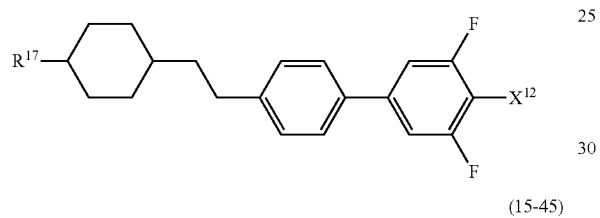
(15-45) 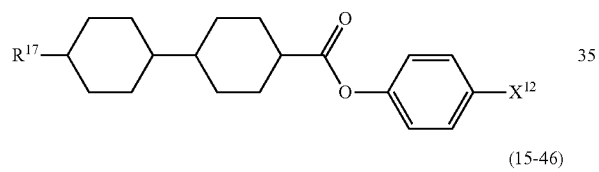
(15-46) 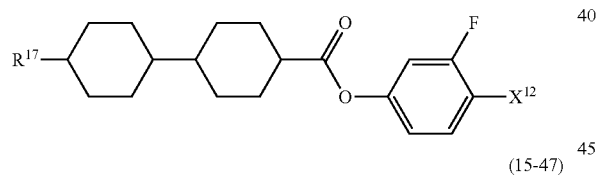
(15-47) 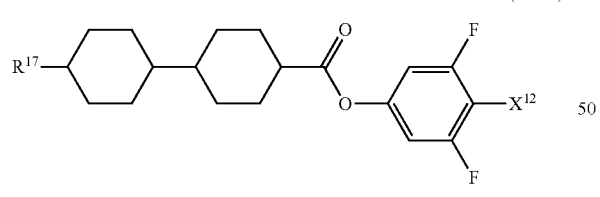
(15-48) 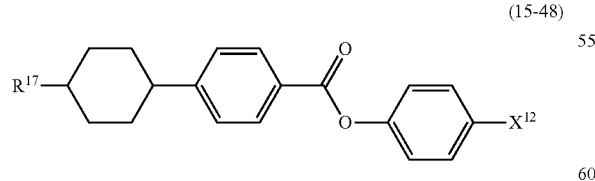
(15-49) 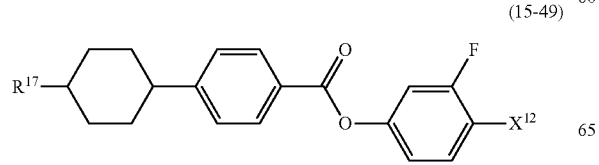
(15-50) 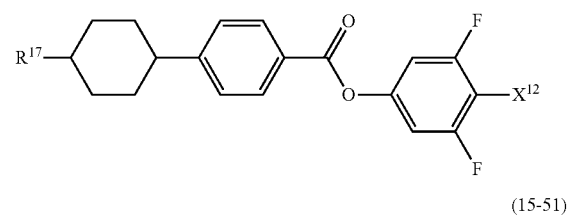
(15-51) 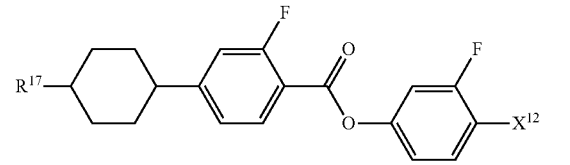
(15-52) 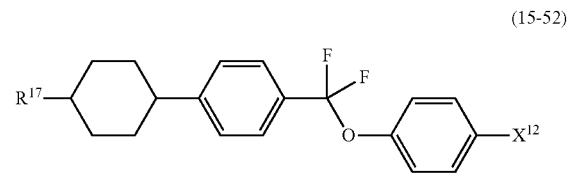
(15-53) 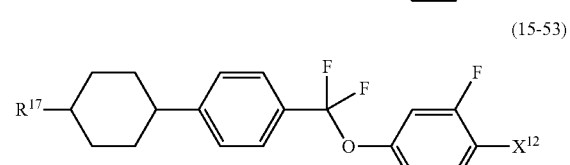
(15-54) 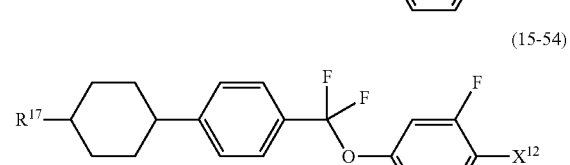
(15-55) 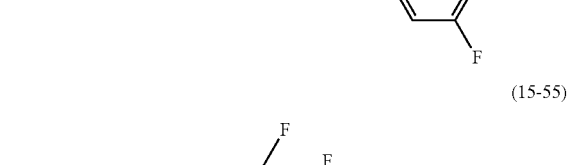
(15-56) 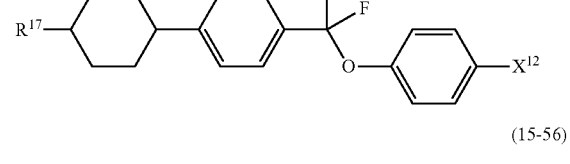
(15-57) 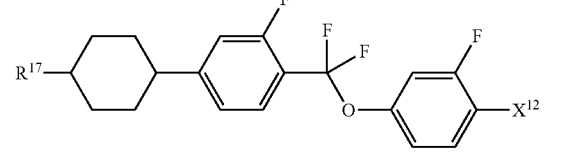
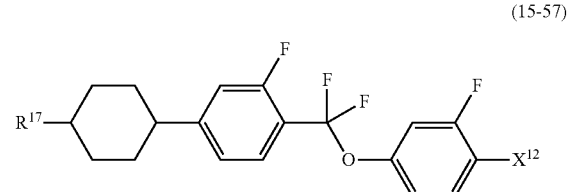

-continued (15-58)
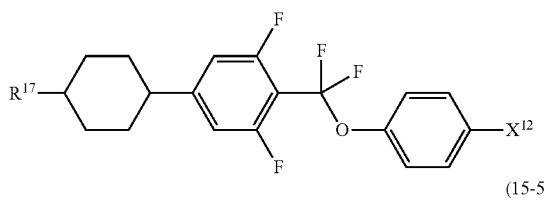

(15-59)
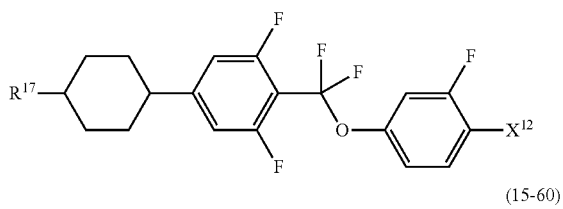

(15-60)
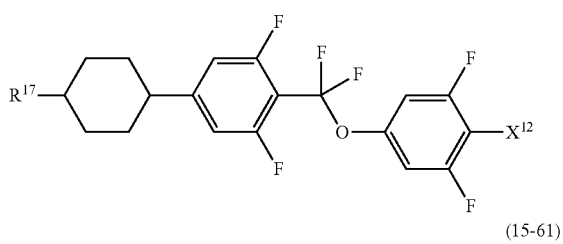

(15-61)
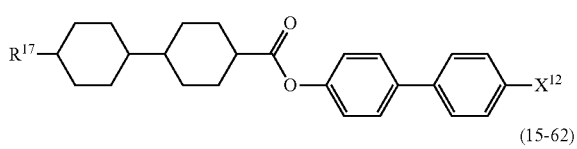

(15-62)
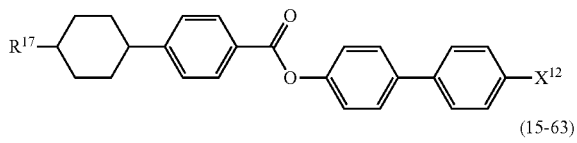

(15-63)
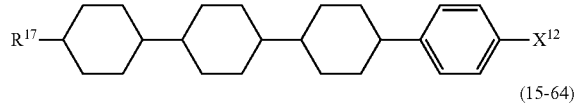

(15-64)
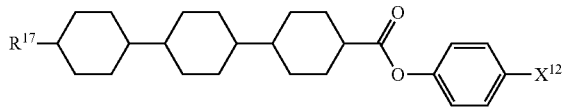

Component (e) has the positive dielectric anisotropy and the large value thereof, and therefore is used when a composition for the TN mode or the like is prepared. The dielectric anisotropy of the composition can be increased by containing of component (e). Containing of component (e) is effective for extending the temperature range of the liquid crystal phase, adjusting the viscosity or adjusting the optical anisotropy. Containing of component (e) is also useful in adjusting the voltage-transmittance curve of the device.

When a composition for the TN mode or the like is prepared, a content of component (e) is suitably in the range of approximately 1 to approximately 99% by weight, preferably in the range of approximately 10 to approximately 97% by weight, and further preferably in the range of approximately 40 to approximately 95% by weight, based on the weight of the composition. When component (e) is added to the composition having the negative dielectric anisotropy, the content of component (e) is preferably approximately 30% by weight or less. The elastic constant of the composition and the voltage-transmittance curve of the device can be adjusted by adding component (e) thereto.

The liquid crystal composition satisfying at least one of physical properties such as the high stability to heat and light, the high maximum temperature, the low minimum temperature, the small viscosity, the suitable optical anisotropy (namely, the large optical anisotropy or small optical anisotropy), the large positive or negative dielectric anisotropy, a large specific resistance and a suitable elastic constant (namely, a large elastic constant or a small elastic constant) can be prepared by appropriately combining components (b) to (e) described above with compound (1). A device including such a composition has the wide temperature range in which the device can be used, a short response time, the large voltage holding ratio, the low threshold voltage, a large contrast ratio and a long service life.

If the device is used for the long period of time, a flicker may be occasionally generated on a display screen. A flicker factor (%) can be represented by an expression described below:

$$(|\text{luminance upon applying a positive voltage}-\text{luminance upon applying a negative voltage}|)/\text{average luminance})\times 100.$$

In the device having the flicker factor in the range of approximately 0 to approximately 1%, the flicker is hard to be generated on the display screen even when the device is used for the long period of time. The flicker is associated with image persistence, and is presumed to be generated according to a potential difference between a positive frame and a negative frame in driving at alternating current. The composition containing compound (1) is also useful to reduce generation of the flicker.

3-2. Additive

The liquid crystal composition is prepared by a known method. For example, the component compounds are mixed and dissolved in each other by heating. According to an application, the additive may be added to the composition. Examples of the additive include the polymerizable compound, the polymerization initiator, the polymerization inhibitor, the optically active compound, the antioxidant, the ultraviolet light absorber, the light stabilizer, the heat stabilizer, the dye and the antifoaming agent. Such additives are well known to those skilled in the art, and described in literature.

In a liquid crystal display device having the PSA (polymer sustained alignment) mode, the composition contains the polymer. The polymerizable compound is added for the purpose of forming the polymer in the composition. The polymer is produced in the composition by irradiating the composition with ultraviolet light in a state in which the voltage is applied between electrodes to polymerize the polymerizable compound. A suitable pretilt angle is achieved by the method, and therefore the device is prepared in which the response time is shortened and the image persistence is improved.

Examples of a preferred polymerizable compound include acrylate, methacrylate, a vinyl compound, a vinyloxy compound, propenyl ether, an epoxy compound (oxirane, oxetane) and vinyl ketone. Examples of a further preferred compound include a compound having at least one piece of acryloyloxy and a compound having at least one piece of methacryloyloxy. Examples of a still further preferred compound include also a compound having both acryloyloxy and methacryloyloxy.

The further preferred examples include compounds (M-1) to (M-18). In the compounds, $R^{25}$ to $R^{31}$ are independently hydrogen or methyl; $R^{32}$, $R^{33}$ and $R^{34}$ are independently hydrogen or alkyl having 1 to 5 carbons, and at least one of $R^{32}$, $R^{33}$ and $R^{34}$ is alkyl having 1 to 5 carbons; s, v and x are independently 0 or 1; and t and u are independently an integer from 1 to 10. $L^{21}$ to $L^{26}$ are independently hydrogen or fluorine; and $L^{27}$ and $L^{28}$ are independently hydrogen, fluorine or methyl.

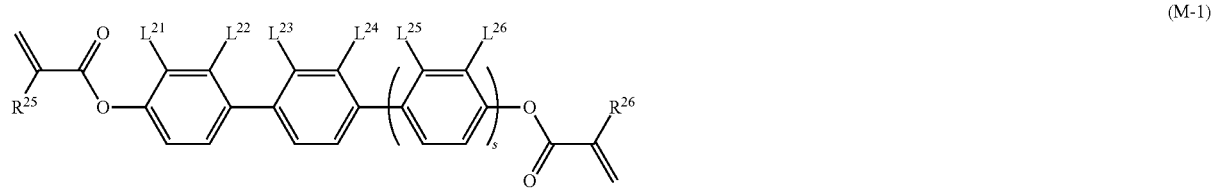
(M-1)

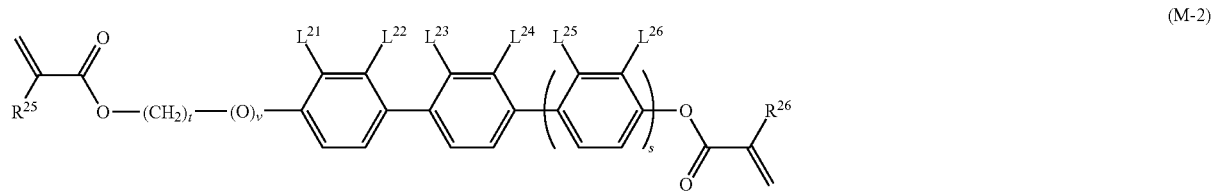
(M-2)

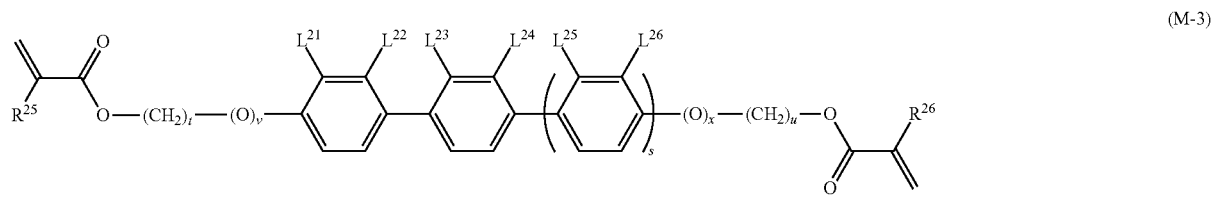
(M-3)

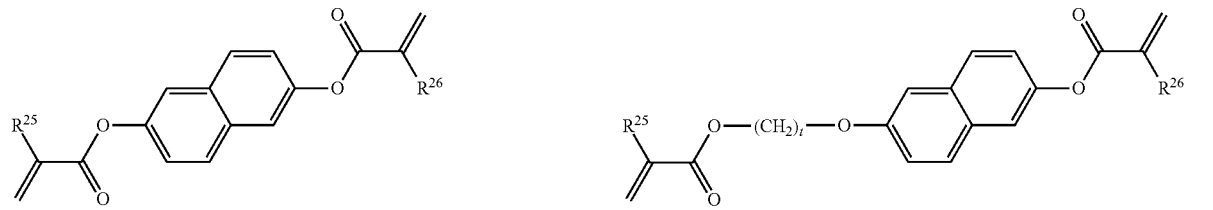
(M-4) (M-5)

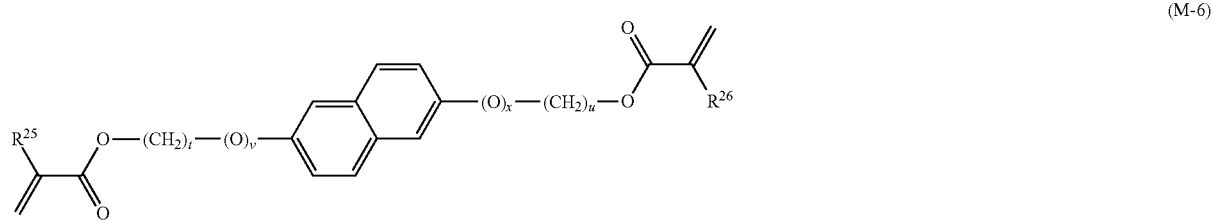
(M-6)

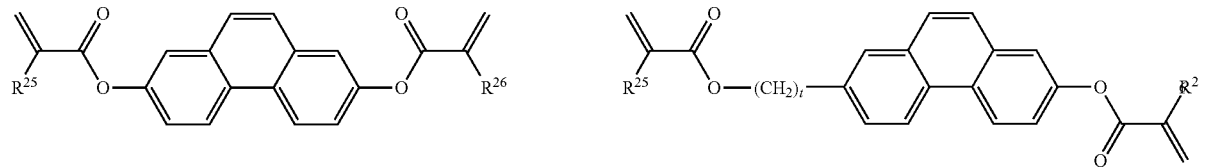
(M-7) (M-8)

(M-9)
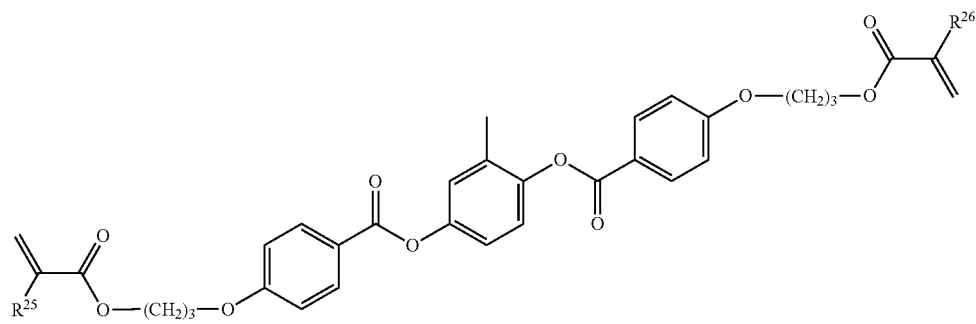
(M-10)
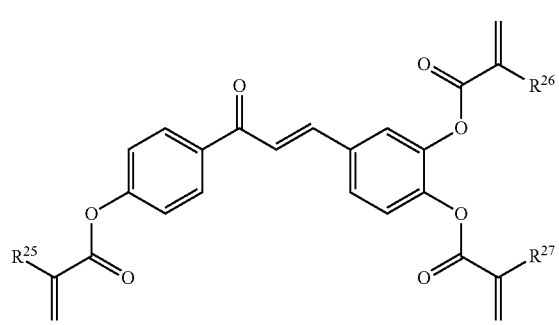
(M-11)
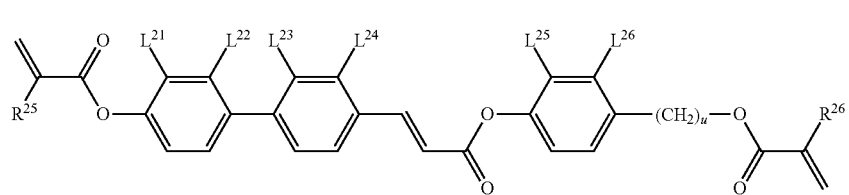
(M-12)
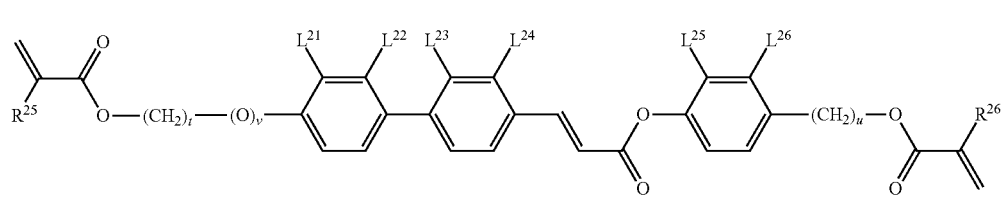
(M-13)
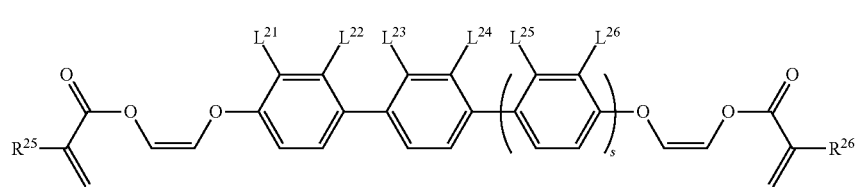
(M-14)
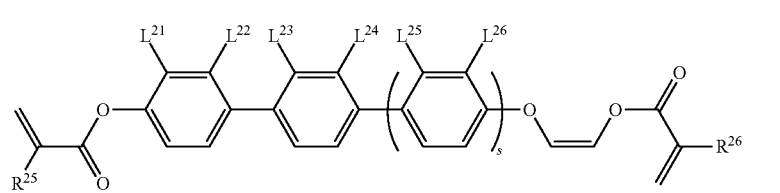

(M-15)
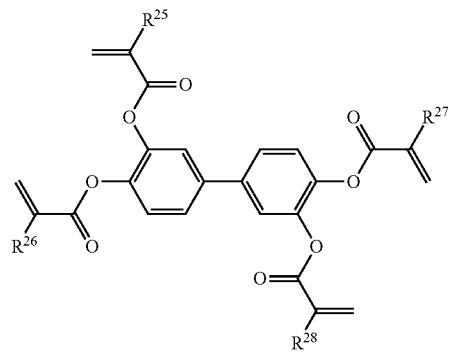

(M-16)
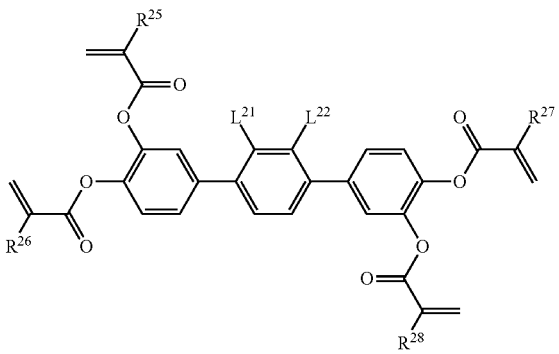

(M-17)
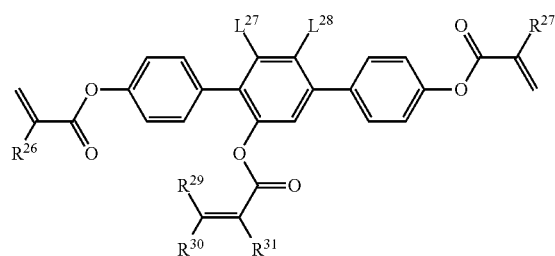

(M-18)
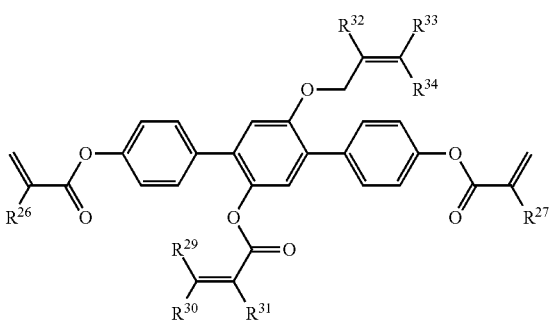

The polymerizable compound can be rapidly polymerized by adding the polymerizable initiator. An amount of a remaining polymerizable compound can be decreased by optimizing reaction conditions. Examples of a photoradical polymerization initiator include TPO, 1173 and 4265 from Darocur series, and 184, 369, 500, 651, 784, 819, 907, 1300, 1700, 1800, 1850 and 2959 from Irgacure series, each being made by BASF SE.

Additional examples of the photoradical polymerization initiator include 2-(4-butoxystyryl)-5-trichloromethyl-1, 3, 4-oxadiazole, 9-phenylacridine, a benzophenone/Michler's ketone mixture, a hexaarylbiimidazole/mercaptobenzimidazole mixture, 1-(4-isopropylphenyl)-2-hydroxy-2-methylpropane-1-one, benzyl dimethyl ketal, 2-methyl-1-[4-(methylthio)phenyl]-2-morpholinopropane-1-one, a 2,4-diethylxanthone/methyl p-dimethylaminobenzoate mixture and a benzophenone/methyltriethanolamine mixture.

After the photoradical polymerization initiator is added to the liquid crystal composition, polymerization can be performed by irradiating the composition with ultraviolet light in a state in which an electric field is applied. However, an unreacted polymerization initiator or a decomposition product of the polymerization initiator may cause poor display such as the image persistence to the device. In order to prevent such poor display, photopolymerization may be performed without adding the polymerization initiator. A preferred wavelength of light to be irradiated is in the range of approximately 150 nanometers to approximately 500 nanometers. A further preferred wavelength is in the range of approximately 250 nanometers to approximately 450 nanometers, and a most preferred wavelength is in the range of approximately 300 nanometers to approximately 400 nanometers.

Upon storing the polymerizable compound, the polymerization inhibitor can be added in order to prevent polymerization. The polymerizable compound is ordinarily added to the composition without removing the polymerization inhibitor. Examples of the polymerization inhibitor include hydroquinone, a hydroquinone derivative such as methylhydroquinone, and 4-tert-butylcatechol, 4-methoxyphenol and phenothiazine.

Addition of the optically active compound is effective in inducing a helical structure in liquid crystal molecules to give a required twist angle, thereby preventing a reverse twist. A helical pitch can be adjusted by adding the optically active compound. Two or more of the optically active compounds can be added for the purpose of adjusting temperature dependence of the helical pitch. Preferred examples of the optically active compound include compounds (Op-1) to (Op-18) below. In compound (Op-18), ring J is 1,4-cyclohexylene or 1,4-phenylene, and $R^{28}$ is alkyl having 1 to 10 carbons. A symbol * represents asymmetrical carbon.

(Op-1)
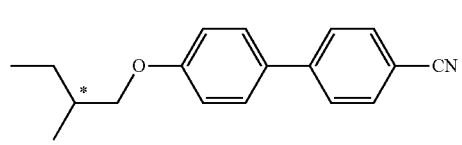

(Op-2)
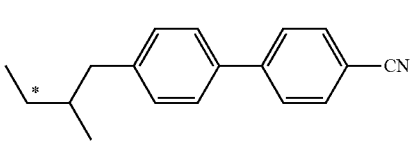

-continued
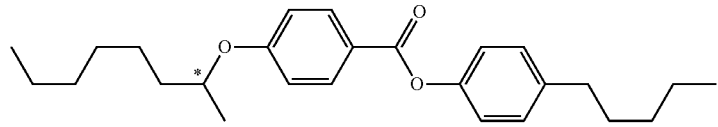
(Op-3)
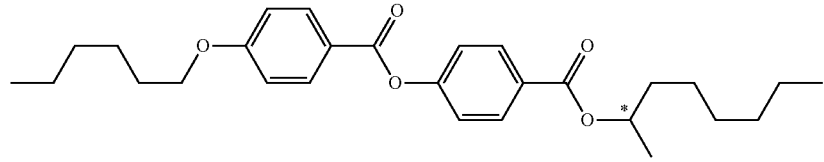
(Op-4)
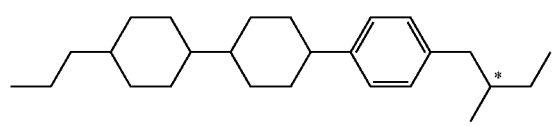
(Op-5)
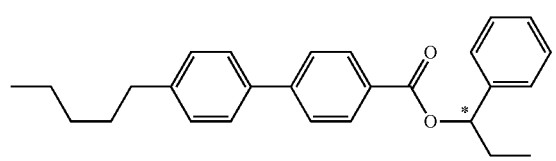
(Op-6)
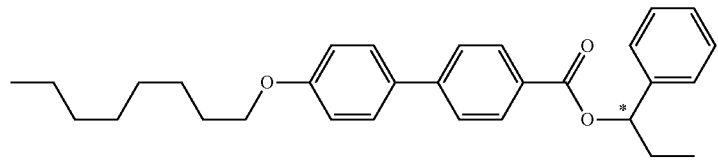
(Op-7)
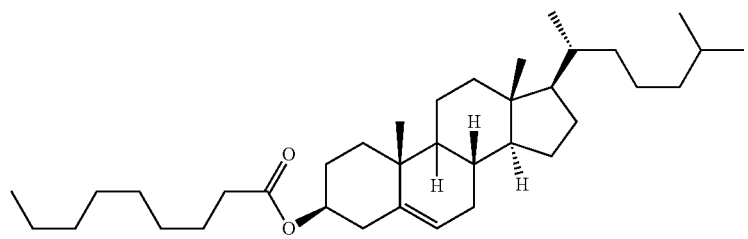
(Op-8)
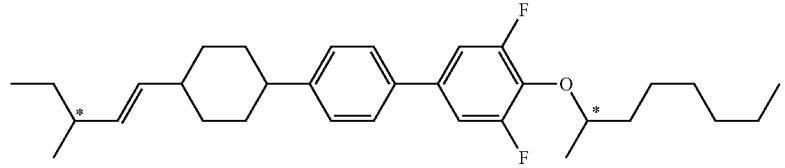
(Op-9)
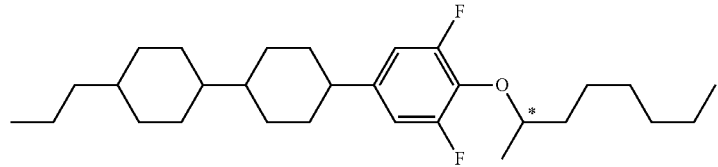
(Op-10)
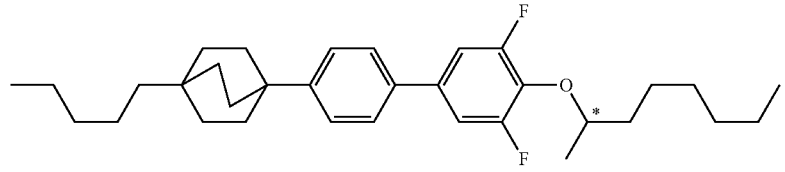
(Op-11)
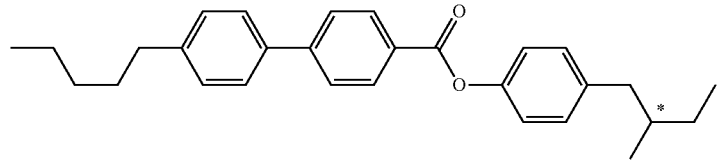
(Op-12)

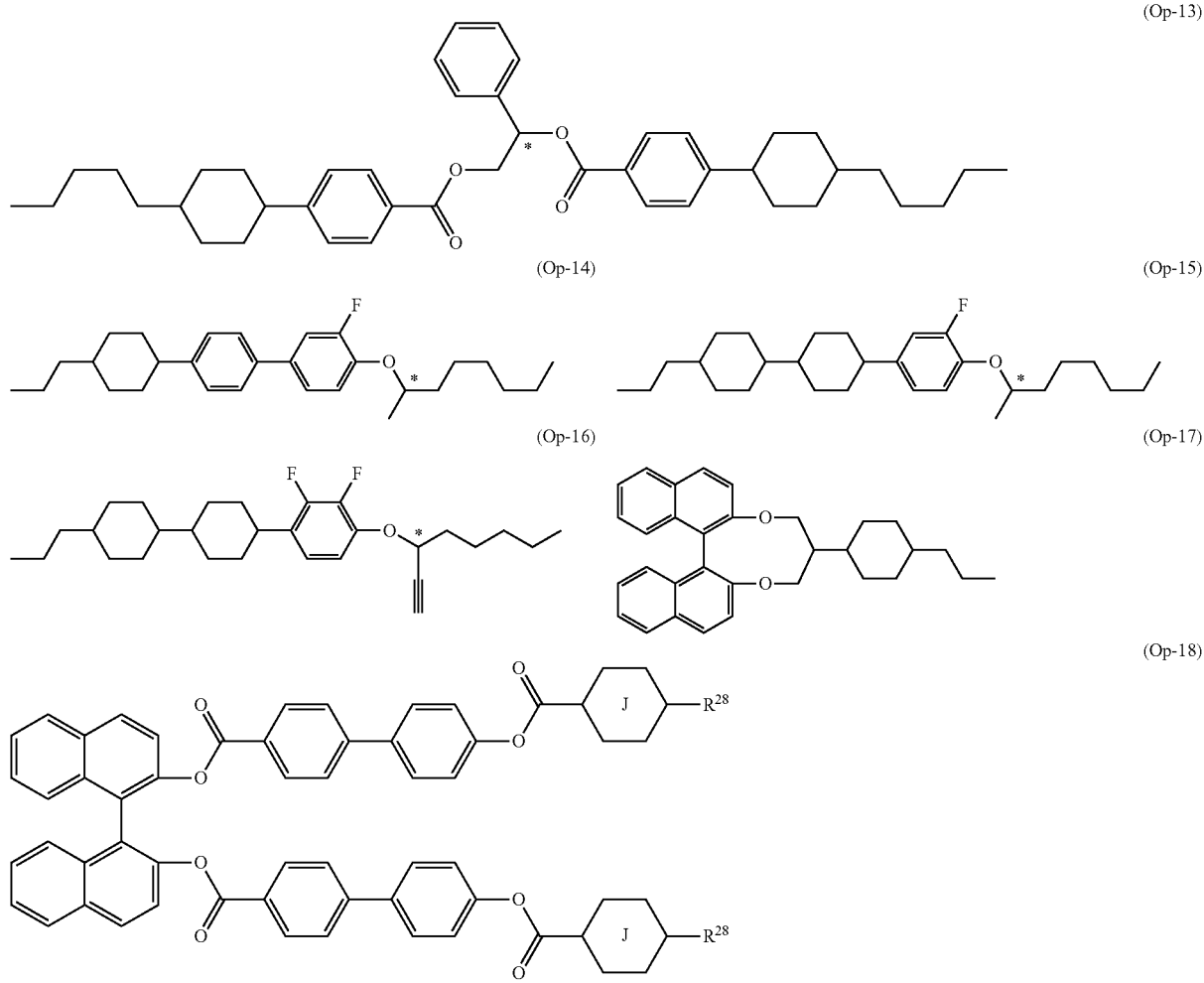

Addition of the antioxidant is effective for maintaining the large voltage holding ratio. Preferred examples of the antioxidant include compounds (AO-1) and (AO-2) below; Irganox 415, Irganox 565, Irganox 1010, Irganox 1035, Irganox 3114 and Irganox 1098 (trade names for all, made by BASF SE). Addition of the ultraviolet light absorber is effective for preventing reduction of the maximum temperature. Preferred examples of the ultraviolet light absorbent include a benzophenone derivative, a benzoate derivative and a triazole derivative, and examples thereof include compounds (AO-3) and (AO-4) below; Tinuvin 329, Tinuvin P, Tinuvin 326, Tinuvin 234, Tinuvin 213, Tinuvin 400, Tinuvin 328 and Tinuvin 99-2 (trade names for all, made by BASF SE); and 1,4-diazabicyclo[2.2.2]octane (DABCO)

Addition of the light stabilizer such as amine having steric hindrance is preferred for maintaining the large voltage holding ratio. Preferred examples of the light stabilizer include compounds (AO-5) and (AO-6) below; Tinuvin 144, Tinuvin 765 and Tinuvin 770DF (trade names for all, made by BASF SE); LA-77Y and LA-77G (trade names for all, made by ADEKA Corporation). Addition of the heat stabilizer is also effective for maintaining the large voltage holding ratio. Preferred examples thereof include IRGAFOS 168 (trade name, made by BASF SE). A dichroic dye such as an azo dye or an anthraquinone dye is mixed with the composition to be adapted to a device having a guest host (GH) mode. The defoaming agent is effective for preventing foam formation. Preferred examples of the defoaming agent include dimethyl silicone oil and methylphenyl silicone oil.

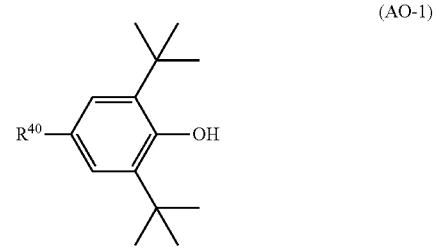

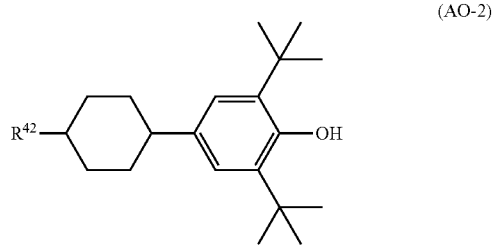

-continued

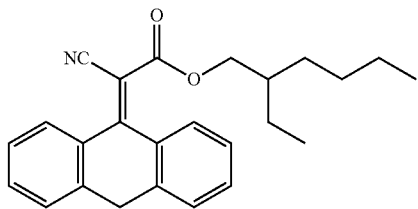
(AO-3)

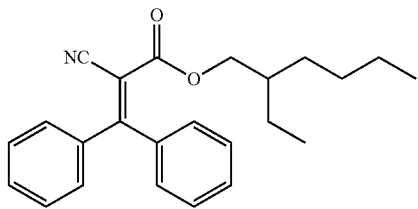
(AO-4)

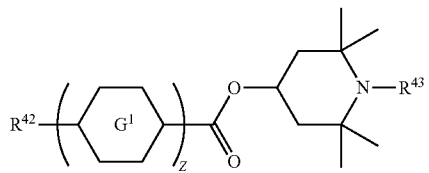
(AO-5)

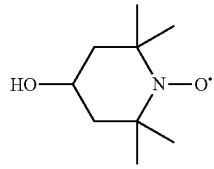
(AO-6)

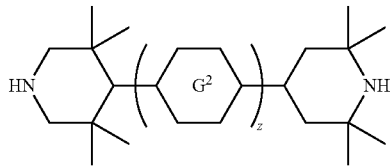
(AO-7)

In compound (AO-1), $R^{40}$ is alkyl having 1 to 20 carbons, alkoxy having 1 to 20 carbons, —COOR$^{41}$ or —CH$_2$CH$_2$COOR$^{41}$, in which $R^{41}$ is alkyl having 1 to 20 carbons. In compounds (AO-2) and (AO-5), $R^{42}$ is alkyl having 1 to 20 carbons. In compound (AO-5), $R^{43}$ is hydrogen, methyl or O˙ (oxygen radical); ring $G^1$ is 1,4-cyclohexylene or 1,4-phenylene; and in compound (AO-7), ring $G^2$ is 1,4-cyclohexylene, 1,4-phenylene or 1,4-phenylene in which at least one piece of hydrogen is replaced by fluorine; and in compounds (AO-5) and (AO-7), z is 1, 2 or 3.

4. Liquid Crystal Display Device

The composition can be used for a liquid crystal display device having an operating mode such as the PC mode, the TN mode, the STN mode, the OCB mode and the PSA mode and driven by an active matrix (AM) mode. The composition can also be used for a liquid crystal display device having the operating mode such as the PC mode, the TN mode, the STN mode, the OCB mode, the VA mode and the IPS mode and driven by a passive matrix mode. The device can be adapted to any of a reflective type, a transmissive type and a transflective type.

The composition is also suitable for a nematic curvilinear aligned phase (NCAP) device in which the composition is microencapsulated. The composition can also be used for a polymer dispersed liquid crystal display device (PDLCD) and a polymer network liquid crystal display device (PN-LCD). In the compositions, the polymerizable compound is added in a large amount. Meanwhile, when a proportion of the polymerizable compound is approximately 10% by weight or less based on the weight of the liquid crystal composition, the liquid crystal display device having the PSA mode is prepared. A preferred proportion of the polymerizable compound is in the range of approximately 0.1% by weight to approximately 2% by weight. A further preferred proportion thereof is in the range of approximately 0.2% by weight to approximately 1.0% by weight. The device having the PSA mode can be driven by a driving mode such as the active matrix mode or the passive matrix mode. Such devices can be adapted to any of the reflective type, the transmissive type and the transflective type.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

1. Example of Compound (1)

The invention will be described in greater detail by way of Examples. The examples are exemplary embodiments and not intended to limit the scope of the invention. Compound (1) was prepared by procedures described below. The thus prepared compound was identified by a method such as NMR analysis. Physical properties of the compound and a composition and characteristics of a device were measured by methods described below.

NMR analysis: As a measuring apparatus, DRX-500 made by Bruker BioSpin Corporation was used. In $^1$H-NMR measurement, a sample was dissolved in a deuterated solvent such as CDCl$_3$, and measurement was carried out under conditions of room temperature, 500 MHz and 16 times of accumulation. Tetramethylsilane was used as an internal standard. In $^{19}$F-NMR measurement, CFCl$_3$ was used as the internal standard, and measurement was carried out under conditions of 24 times of accumulation. In explaining nuclear magnetic resonance spectra obtained, s, d, t, q, quin, sex, m and r stand for a singlet, a doublet, a triplet, a quartet, a quintet, a sextet, a multiplet and br being broad, respectively.

Gas chromatographic analysis: GC-2010 Gas Chromatograph made by Shimadzu Corporation was used for measurement. Capillary column DB-1 (length 60 m, bore 0.25 mm, film thickness 0.25 μm) made by Agilent Technologies, Inc. was used. Helium (1 mL per minute) was used as a carrier gas. A temperature in a sample vaporizing chamber and a detector (FID) each was set to 300° C. A sample was dissolved in acetone to prepare a 1% by weight solution, and 1 μL of the solution obtained was injected into the sample vaporizing chamber. A recorder such as a GC Solution system made by Shimadzu Corporation was used.

HPLC analysis: Prominence (LC-20AD; SPD-20A) made by Shimadzu Corporation was used for measurement. As a column, YMC-Pack ODS-A (length: 150 mm, bore: 4.6 mm, particle diameter: 5 μm) made by YMC GmbH was used. As an eluate, acetonitrile and water were appropriately mixed and used. As a detector, a UV detector, an RI detector, a CORONA detector or the like was appropriately used. When the UV detector was used, a detection wavelength was adjusted to 254 nm. A sample was dissolved in acetonitrile and prepared to be a 0.1% by weight solution, and 1 μL of the solution obtained was injected into the sample injector. C-R7Aplus made by Shimadzu Corporation was used as a recorder.

Ultraviolet visible spectrometry: PharmaSpec UV-1700 made by Shimadzu Corporation was used for measurement. A detection wavelength was adjusted to 190 to 700 nm. A sample was dissolved in acetonitrile, and prepared to be a 0.01 mmol/L solution, and was put in a quartz cell (light path length: 1 cm) and measured.

Sample for measurement: When phase structure and a transition temperature (a clearing point, a melting point, a polymerization starting temperature or the like) were measured, a liquid crystal compound itself was used as a sample. When characteristics such as a maximum temperature of a nematic phase, viscosity, optical anisotropy and dielectric anisotropy were measured, a composition prepared by mixing the compound with a base liquid crystal was used as a sample.

When the sample in which the compound was mixed with the base liquid crystal was used, measurement was carried out according to the method described below. The sample was prepared by mixing 15% by weight of the compound and 85% by weight of the base liquid crystal. Then, extrapolated values were calculated from measured values of the sample, according to the equation described below, and the extrapolated values were described.

{Extrapolated value}={100×(measured value of a sample)−(% by weight of a base liquid crystal)×(measured value of the base liquid crystal)}/(% by weight of the compound).

When crystals (or a smectic phase) precipitated at 25° C. even at the ratio of the compound to the base liquid crystal, a ratio of the compound to the base liquid crystal was changed in the order of (10% by weight:90% by weight), (5% by weight:95% by weight) and (1% by weight:99% by weight), and physical properties of the sample were measured at a ratio at which no crystals (or no smectic phase) precipitated at 25° C. In addition, unless otherwise noted, the ratio of the compound to the base liquid crystal is 15% by weight:85% by weight.

When dielectric anisotropy of the compound was zero or positive, base liquid crystal (A) below was used. Ratios of components are expressed in terms of % by weight.

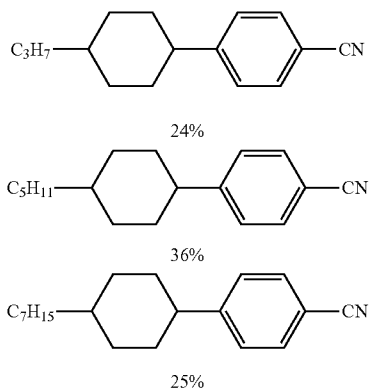

24%

36%

25%

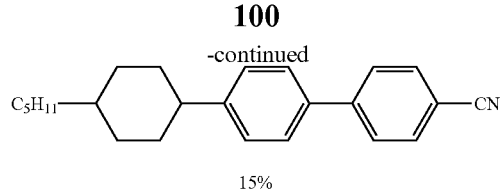

15%

When dielectric anisotropy of the compound was zero or negative, base liquid crystal (B) below was used. Ratios of components are expressed in terms of % by weight.

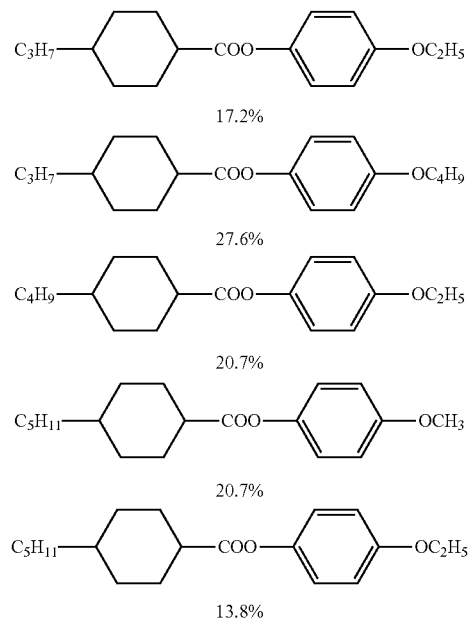

17.2%

27.6%

20.7%

20.7%

13.8%

Measuring methods: Physical properties were measured according to the methods described below. Most of the measuring methods are applied as described in the Standard of the Japan Electronics and Information Technology Industries Association (JEITA EIAJ ED-2521B) discussed and established by JEITA, or modified thereon. Methods modified thereon were also applied. No thin film transistor (TFT) was attached to a TN device used for measurement.

(1) Phase structure: A sample was placed on a hot plate of a melting point apparatus (FP-52 Hot Stage made by Mettler-Toledo International Inc.) equipped with a polarizing microscope, and a state of phase and a change thereof were observed with the polarizing microscope while the sample was heated at a rate of 3° C. per minute, and a kind of the phase was specified.

(2) Transition temperature (° C.): A differential scanning calorimeter, Diamond DSC System, made by PerkinElmer, Inc. or a high sensitivity differential scanning calorimeter, X-DSC7000, made by SII NanoTechnology, Inc. was used for measurement. A sample was heated and then cooled at a rate of 3° C. per minute, a starting point of an endothermic peak or an exothermic peak caused by a phase change of the sample was determined by extrapolation, and thus a transition temperature was determined. A melting point and a polymerization starting temperature of a compound were also measured using the apparatus. Temperature at which a compound undergoes transition from a solid to a liquid crystal phase such as the smectic phase or the nematic phase may be occasionally abbreviated as "minimum temperature of the liquid crystal phase." Temperature at which the compound undergoes transition from the liquid crystal phase to the liquid may be occasionally abbreviated as "clearing point."

The crystals were expressed as C. When the crystals were distinguishable into two kinds, each of the crystals was expressed as $C_1$ or $C_2$. The smectic phase or the nematic phase was expressed as S or N. When smectic A phase, smectic B phase, smectic C phase or smectic F phase was distinguishable, the phases were expressed as $S_A$, $S_B$, $S_C$ or $S_F$, respectively. A liquid (isotropic) was expressed as I. A transition temperature was expressed as "C 50.0 N 100.0 I," for example. The expression indicates that a transition temperature from the crystal to the nematic phase is 50.0° C., and a transition temperature from the nematic phase to the liquid is 100.0° C.

(3) Compatibility of compounds: Some compounds having a similar structure were mixed to prepare a base liquid crystal having a nematic phase. A compound to be measured was added to the base liquid crystal to prepare a sample. One example of a mixing proportion is 15% by weight of the compound and 85% by weight of the base liquid crystal. The sample was kept for 30 days at a low temperature such as −20° C. and −30° C. Whether or not part of the sample changed to crystals (or a smectic phase) was observed. Measuring conditions such as a mixing proportion and a storage temperature were changed when necessary. From the thus measured results, conditions under which the crystals (or the smectic phase) precipitated or conditions under which no crystals (or no smectic phase) precipitated were determined. A measure of compatibility was expressed depending on the conditions.

(4) Maximum temperature of nematic phase ($T_{NI}$ or NI; ° C.): A sample was placed on a hot plate in a melting point apparatus equipped with a polarizing microscope, and heated at a rate of 1° C. per minute. Temperature when part of the sample began to change from a nematic phase to an isotropic liquid was measured. When the sample was a mixture of compound (1) and a base liquid crystal, a maximum temperature was expressed in terms of a symbol $T_{NI}$. When the sample was a mixture of compound (1) and a compound selected from compounds (2) to (15), the maximum temperature was expressed in terms of a symbol NI. A maximum temperature range of the nematic phase may be occasionally abbreviated as "maximum temperature."

(5) Minimum temperature of nematic phase ($T_c$; ° C.): Samples each having a nematic phase were put in glass vials and kept in freezers at temperatures of 0° C., −10° C., −20° C., −30° C. and −40° C. for 10 days, and then liquid crystal phases were observed. For example, when the sample maintained a nematic phase at −20° C. and changed to crystals or a smectic phase at −30° C., $T_c$ was expressed as $T_c$<−20° C. A minimum temperature range of a nematic phase may be occasionally abbreviated as "minimum temperature."

(6) Viscosity (bulk viscosity; η; measured at 20° C.; mPa·s): A cone-plate (E type) rotational viscometer made by Tokyo Keiki, Inc. was used for measurement.

(7) Optical anisotropy (refractive index anisotropy; Δn; measured at 25° C.): Measurement was carried out by an Abbe refractometer with a polarizing plate mounted on an ocular, using light at a wavelength of 589 nm. A surface of a main prism was rubbed in one direction, and then a sample was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of optical anisotropy was calculated from the following equation: Δn=n∥−n⊥.

(8) Specific resistance (ρ; measured at 25° C.; Ωcm): Into a vessel equipped with electrodes, 1.0 mL of a sample was injected. A direct current voltage (10 V) was applied to the vessel, and a direct current after 10 seconds was measured. Specific resistance was calculated by the expression described below.

(Specific resistance)={(voltage)×(electric capacity of a vessel)}/{(direct current)×(dielectric constant of vacuum)}.

(9) Voltage holding ratio (VHR-1; measured at 25° C.; %): A TN device used for measurement had a polyimide alignment film, and a distance (cell gap) between two glass substrates was 5 μm. A sample was put in a device, and the device was sealed with an ultraviolet-curable adhesive. The device was charged by applying a pulse voltage (60 microseconds at 5 V). A decaying voltage was measured for 16.7 milliseconds with a high-speed voltmeter, and area A between a voltage curve and a horizontal axis in a unit cycle was determined. Area B is an area without decay. A voltage holding ratio is expressed in terms of a percentage of area A to area B.

(10) Voltage holding ratio (VHR-2; measured at 80° C.; %): A voltage holding ratio was measured according to procedures identical with the procedures described above except that measurement was carried out at 80° C. in place of 25° C. The thus obtained results were expressed in terms of VHR-2.

(11) Flicker factor (measured at 25 C; %): 3298F Multimedia Display Tester made by Yokogawa Electric Corporation was used for measurement. A light source was LED. A sample was put in a normally black mode FFS device in which a distance (cell gap) between two glass substrates was 3.5 μm and a rubbing direction was anti-parallel. The device was sealed with an ultraviolet-curable adhesive. Voltage was applied to the device and a voltage having a maximum amount of light transmitted through the device was measured. A flicker factor displayed thereon was read by bringing a sensor unit close to the device while voltage was applied to the device.

Measuring methods for the physical properties may be occasionally different between a sample having positive dielectric anisotropy and a sample having negative dielectric anisotropy. When the sample had the positive dielectric anisotropy, the measuring methods described in sections (12a), (13a), (14a), (15a) and (16a) were applied. When the sample had the negative dielectric anisotropy, the measuring methods were described in sections (12b), (13b), (14b), (15b) and (16b) were applied.

(12a) Viscosity of sample having positive dielectric anisotropy (rotational viscosity; γ1; measured at 25° C.; mPa·s): Measurement was carried out according to a method described in M. Imai et al., Molecular Crystals and Liquid Crystals, Vol. 259, p. 37 (1995). A sample was put in a TN device in which a twist angle was 0 degrees and a distance (cell gap) between two glass substrates was 5 μm. Voltage was applied stepwise to the device in the range of 16 V to 19.5 V at an increment of 0.5 V. After a period of 0.2 second with no voltage application, voltage was repeatedly applied under conditions of only one rectangular wave (rectangular pulse; 0.2 second) and no voltage application (2 seconds). A peak current and a peak time of a transient current generated by the applied voltage were measured. A value of rotational viscosity was obtained from the measured values and calculation equation (8) on page 40 of the paper presented by M. Imai et al. A value of dielectric anisotropy required for the calculation was determined using the device by which the rotational viscosity was measured and by the method described below.

(12b) Viscosity of sample having negative dielectric anisotropy (rotational viscosity; γ1; measured at 25° C.; mPa·s): Measurement was carried out according to a method described in M. Imai et al., Molecular Crystals and Liquid Crystals, Vol. 259, p. 37 (1995). A sample was put in a VA device in which a distance (cell gap) between two glass substrates was 20 µm. Voltage was applied stepwise to the device in the range of 39 V to 50 V at an increment of 1 V. After a period of 0.2 second with no voltage application, voltage was repeatedly applied under conditions of only one rectangular wave (rectangular pulse; 0.2 second) and no voltage application (2 seconds). A peak current and a peak time of a transient current generated by the applied voltage were measured. A value of rotational viscosity was obtained by substituting the measured values into the calculation equation (8) on page 40 of the paper presented by M. Imai et al. As dielectric anisotropy required for the calculation, a value measured in the section of dielectric anisotropy described below was used.

(13a) Dielectric anisotropy ($\Delta \epsilon$) of sample having positive dielectric anisotropy: A sample was put in a TN device in which a distance (cell gap) between two glass substrates was 9 µm and a twist angle was 80 degrees. Sine waves (10 V, 1 kHz) were applied to the device, and after 2 seconds, a dielectric constant (I) in the major axis direction of liquid crystal molecules was measured. Sine waves (0.5 V, 1 kHz) were applied to the device, and after 2 seconds, a dielectric constant ($\epsilon \perp$) in the minor axis direction of the liquid crystal molecules was measured. The measurement was carried out at 25° C. A value of dielectric anisotropy was calculated by the following equation: $\Delta \epsilon = \epsilon \| - \epsilon \perp$.

(13b) Dielectric anisotropy ($\Delta \epsilon$) of sample having negative dielectric anisotropy: A value of dielectric anisotropy was calculated from the equation: $\Delta \epsilon = \epsilon \| - \epsilon \perp$. A dielectric constant ($\epsilon \|$ or $\epsilon \perp$) was measured as described below. The measurement was carried out at 25° C.

(1) Measurement of Dielectric Constant ($\epsilon \|$)

An ethanol (20 mL) solution of octadecyl triethoxysilane (0.16 mL) was applied to a well-cleaned glass substrate. After rotating the glass substrate with a spinner, the glass substrate was heated at 150° C. for 1 hour. A sample was put in a VA device in which a distance (cell gap) between two glass substrates was 4 µm, and the device was sealed with an ultraviolet-curable adhesive. Sine waves (0.5 V, 1 kHz) were applied to the device, and after 2 seconds, a dielectric constant ($\epsilon \|$) in the major axis direction of liquid crystal molecules was measured.

(2) Measurement of Dielectric Constant ($\epsilon \perp$)

A polyimide solution was applied to a well-cleaned glass substrate. After calcining the glass substrate, rubbing treatment was applied to the alignment film obtained. A sample was put in a TN device in which a distance (cell gap) between two glass substrates was 9 µm and a twist angle was 80 degrees. Sine waves (0.5 V, 1 kHz) were applied to the device, and after 2 seconds, a dielectric constant ($\epsilon \perp$) in the minor axis direction of the liquid crystal molecules was measured.

(14a) Elastic constant of sample having positive dielectric anisotropy (K): HP4284A LCR Meter made by Yokogawa-Hewlett-Packard Co. was used for measurement. A sample was put in a horizontal alignment device in which a distance (cell gap) between two glass substrates was 20 µm. An electric charge of 0 V to 20 V was applied to the device, and electrostatic capacity (c) and applied voltage (V) were measured. The measurement was performed at 25° C. The measured values were fitted to equation (2.98) and equation (2.101) on page 75 of "Liquid Crystal Device Handbook" (Ekisho Debaisu Handobukku in Japanese; The Nikkan Kogyo Shimbun, Ltd.) and values of $K_{11}$ and $K_{33}$ were obtained from equation (2.99). Next, $K_{22}$ was calculated using the previously determined values of $K_{11}$ and $K_{33}$ in formula (3.18) on page 171. Elastic constant K is a mean value of the thus determined $K_{11}$, $K_{22}$ and $K_{33}$. A unit of elastic constant K is pN.

(14b) Elastic constant of sample having negative dielectric anisotropy ($K_{11}$ and $K_{33}$): Elastic Constant Measurement System Model EC-1 made by TOYO Corporation was used for measurement. A sample was put in a vertical alignment device in which a distance (cell gap) between two glass substrates was 20 µm. An electric charge of 20 V to 0 V was applied to the device, and electrostatic capacity (C) and applied voltage (V) were measured. The measurement was performed at 25° C. The values were fitted to equation (2.98) and equation (2.101) on page 75 of the "Liquid Crystal Device Handbook (Ekisho Debaisu Handobukku, in Japanese)" (The Nikkan Kogyo Shimbun, Ltd.), and a value of elastic constant was obtained from equation (2.100). A unit of elastic constants $K_{11}$ and $K_{33}$ is pN.

(15a) Threshold voltage (Vth) of sample having positive dielectric anisotropy: An LCD-5100 luminance meter made by Otsuka Electronics Co., Ltd. was used for measurement. A light source was a halogen lamp. A sample was put in a normally white mode TN device in which a distance (cell gap) between two glass substrates was 0.45/Δn (µm) and a twist angle was 80 degrees.

A voltage (32 Hz, rectangular waves) to be applied to the device was stepwise increased from 0 V to 10 V at an increment of 0.02 V. On the occasion, the device was irradiated with light from a direction perpendicular to the device, and an amount of light transmitted through the device was measured. The measurement was carried out at 25° C. A voltage-transmittance curve was prepared, in which a maximum amount of light corresponds to 100% transmittance and a minimum amount of light corresponds to 0% transmittance. A threshold voltage is expressed in terms of a voltage at 90% transmittance. A unit of voltage is V.

(15b) Threshold voltage (Vth) of sample having negative dielectric anisotropy: An LCD-5100 luminance meter made by Otsuka Electronics Co., Ltd. was used for measurement. A light source was a halogen lamp. A sample was put in a normally black mode VA device in which a distance (cell gap) between two glass substrates was 4 µm and a rubbing direction was anti-parallel, and the device was sealed with an ultraviolet-curable adhesive. A voltage (60 Hz, rectangular waves) to be applied to the device was stepwise increased from 0 V to 20 V at an increment of 0.02 V. On the above occasion, the device was irradiated with light from a direction perpendicular to the device, and an amount of light transmitted through the device was measured. The measurement was carried out at 25° C. A voltage-transmittance curve was prepared, in which a maximum amount of light corresponds to 100% transmittance and a minimum amount of light corresponds to 0% transmittance. A threshold voltage is expressed in terms of a voltage at 10% transmittance. A unit of voltage is V.

(16a) Response time (τ) of sample having positive dielectric anisotropy: An LCD-5100 luminance meter made by Otsuka Electronics Co., Ltd. was used for measurement. A light source was a halogen lamp. A low-pass filter was set at 5 kHz. A sample was put in a normally white mode TN device in which a distance (cell gap) between two glass substrates was 5.0 µm and a twist angle was 80 degrees. Rectangular waves (60 Hz, 5 V, 0.5 sec) were applied to the device. On the above occasion, the device was irradiated with light from a direction perpendicular to the device, and an amount of light transmitted through the device was measured. A voltage-transmittance curve was prepared, in which a maximum amount of light corresponds to 100% transmittance and a minimum amount of light corresponds to 0% transmittance. A rise time (τr) is a time taken to change 90% transmittance to 10% transmittance. The measurement was performed at 25° C. A fall time (τf) is a time taken to change 10% transmittance to 90% transmittance. Response time was presented by a sum of the thus rise time and fall time. A unit of response time is ms.

(16b) Response time (τ) of sample having negative dielectric anisotropy: An LCD-5100 luminance meter made by Otsuka Electronics Co., Ltd. was used for measurement. A light source was a halogen lamp. A low-pass filter was set at 5 kHz. A sample was put in a normally black mode PVA device in which a distance (cell gap) between two glass substrates was 3.2 µm and a rubbing direction was antiparallel. The device was sealed with an ultraviolet-curable adhesive. The device was applied with a voltage of a little exceeding a threshold voltage for 1 minute, and then was irradiated with an ultraviolet light of 23.5 mW/cm² for 8 minutes, while applying a voltage of 5.6 V. A voltage (60 Hz, rectangular waves) was applied to the device. On the above occasion, the device was irradiated with light from a direction perpendicular to the device, and an amount of light transmitted through the device was measured. The measurement was carried out at 25° C. A voltage-transmittance curve was prepared, in which a maximum amount of light corresponds to 100% transmittance and a minimum amount of light corresponds to 0% transmittance. A response time is a period of time required for a change from 90% transmittance to 10% transmittance (fall time). A unit of response time is ms.

Synthesis Example 1

Synthesis of Compound (1-3-01)

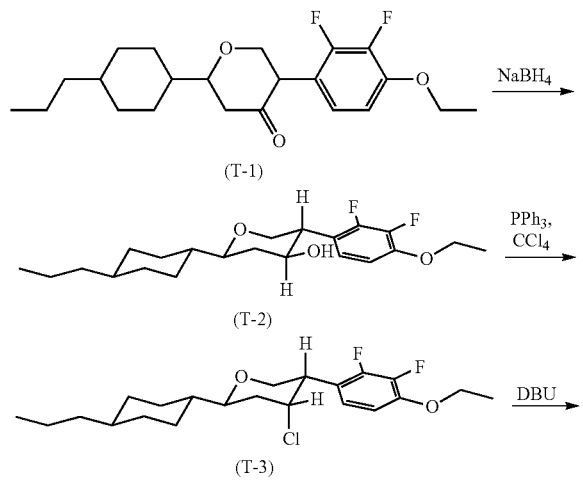

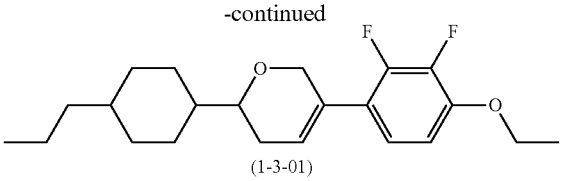

First Step: Synthesis of Compound (T-2)

Compound (T-1) (10.2 g, 26.9 mmol) prepared by a known method was dissolved in ethanol (100 mL) and tetrahydrofuran (200 mL), and the resulting mixture was cooled in an ice bath. Sodium borohydride (0.7 g, 17.5 mmol) was added thereto, and the resulting mixture was stirred at room temperature for 2 hours. After reaction completion, the reaction mixture was poured into a saturated aqueous solution (500 mL) of ammonium chloride, and subjected to extraction with ethyl acetate (200 mL, three times). The combined organic layer was washed with a saturated aqueous solution (500 mL) of sodium chloride and water (500 mL), and then dried over anhydrous magnesium sulfate and concentrated under reduced pressure. The residue was purified by silica gel chromatography (5% ethyl acetate in heptane) to give compound (T-2) (10.3 g, 26.9 mmol) as a colorless solid.

Second Step: Synthesis of Compound (T-3)

Compound (T-2) (10.2 g, 26.9 mmol) and carbon tetrachloride (5.5 mL, 57.2 mmol) were dissolved in methylene chloride (100 mL). A methylene chloride solution (20 mL) of triphenylphosphine (14.4 g, 54.8 mmol) was added dropwise thereto, and then the resulting mixture was refluxed for 3 hours. After the resulting mixture was concentrated under reduced pressure, the residue was purified by silica gel chromatography (toluene) to give compound (T-3) (10.5 g, 26.2 mmol) as a colorless solid.

Third Step: Synthesis of Compound (1-3-01)

Compound (T-3) (10.5 g, 26.2 mmol) was dissolved in tetrahydrofuran (150 mL). Diazabicycloundecen (8.5 mL, 56.7 mmol) was added dropwise thereto at room temperature, and then the resulting mixture was stirred at 40° C. for 6 hours. After reaction completion, the reaction mixture was poured into a saturated aqueous solution (500 mL) of ammonium chloride, and subjected to extraction with toluene (200 mL, three times). The combined organic layer was washed with a saturated aqueous solution (500 mL) of sodium chloride and water (500 mL), and then dried over anhydrous magnesium sulfate and concentrated under reduced pressure. The residue was purified by silica gel chromatography (toluene) and recrystallized (in heptane) to give compound (1-3-01) (7.7 g, 21.0 mmol) as a colorless needle crystal.

$^1$H-NMR (CDCl$_3$; δ ppm): 6.86 (td, 1H), 6.68 (t, 1H), 6.03 (s, 1H), 4.42 (s, 2H), 4.11 (q, 2H), 3.28 (ddd, J=4.3, 7.1, 11.0 Hz, 1H), 2.25-2.15 (m, 2H), 2.05 (d, 1H), 1.79 (d, 2H), 1.73 (d, 1H), 1.45 (t, 3H), 1.41-1.35 (m, 1H), 1.34-1.28 (m, 2H), 1.19-1.14 (m, 3H), 1.10-0.98 (m, 2H), 0.95-0.86 (m, 5H).

$^{19}$F-NMR (δ ppm; CDCl$_3$): −139.61 (dd, J=7.7 Hz, 19.3 Hz, 1F), −159.66 (dd, J=7.7 Hz, 20.6 Hz, 1F).

Phase transition temperature; C 79.0 SA 108.9 N 164.6 I; maximum temperature (NI)=151.3° C.; dielectric anisotropy (Δ∈)=−6.4; optical anisotropy (Δn)=0.140; viscosity (η)=51.0 mPa·s.

Reference Example 1

Synthesis of Compound (R-1)

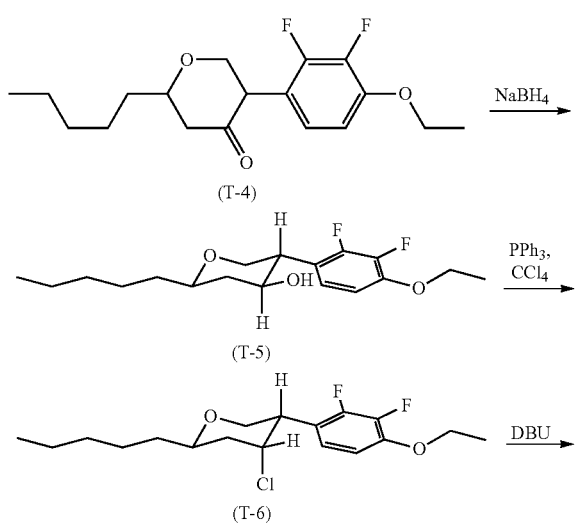
(T-4)
(T-5)
(T-6)

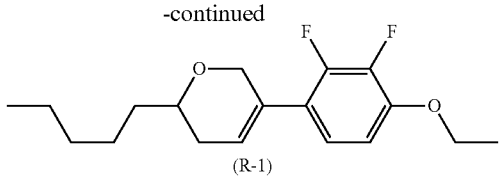
(R-1)

Compound (R-1) was prepared in a manner similar to Synthesis Example 1. When 12.5 g of compound (T-4) prepared by a known method was used as a starting material, an objective compound was obtained as a colorless plate-like crystal (7.4 g)

$^1$H-NMR (CDCl$_3$; δ ppm): 6.86 (td, 1H), 6.68 (t, 1H), 6.02 (s, 1H), 4.47-4.39 (m, 2H), 4.11 (q, 2H), 3.59-3.54 (m, 1H), 2.23-2.11 (m, 2H), 1.65-1.58 (m, 1H), 1.54-1.48 (m, 2H), 1.45 (t, 3H), 1.41-1.29 (m, 5H), 0.91 (t, 3H).

$^{19}$F-NMR (δ ppm; CDCl$_3$): −139.61 (dd, J=7.9-19.3 Hz, 1F), −159.64 (dd, J=7.7 Hz, 18.7 Hz, 1F).

Phase transition temperature; C 20.2 C 38.7 I; maximum temperature (NI)=9.9° C.; dielectric anisotropy (Δ∈)=−6.1; optical anisotropy (Δn)=0.094; viscosity (η)=40.0 mPa·s.

Synthesis Example 2

Synthesis of Compound (1-3-49)

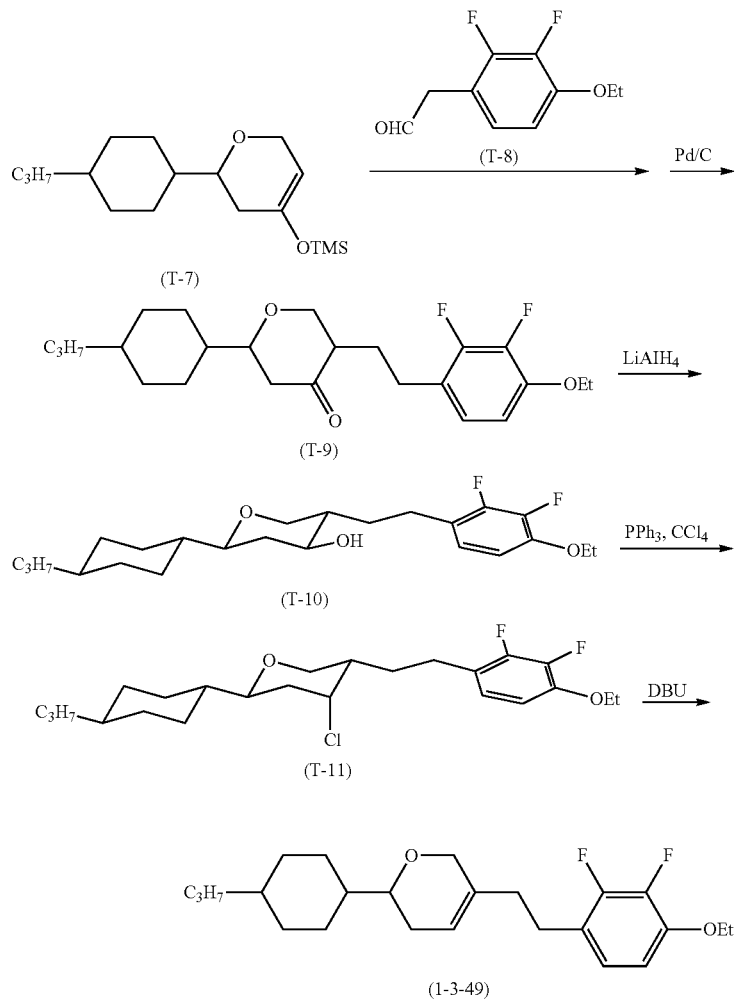
(T-7)
(T-9)
(T-10)
(T-11)
(1-3-49)

First Step: Synthesis of Compound (T-9)

Compound (T-7) (19.0 g, 64.1 mmol) prepared by a known method was dissolved in tetrahydrofuran (150 mL), and the resulting mixture was cooled in an ice bath. A boron trifluoride-diethyl ether complex (17.0 mL, 128.2 mmol) was added thereto, and the resulting mixture was stirred for 15 minutes. A tetrahydrofuran solution (60 mL) of compound (T-8) (12.9 g, 64.1 mmol) was added dropwise thereto, and the resulting mixture was stirred at room temperature for 1 day. After reaction completion, the reaction mixture was poured into 1 N hydrochloric acid (500 mL), and subjected to extraction with ethyl acetate (300 mL, three times). The combined organic layer was washed with a saturated aqueous solution (500 mL) of sodium chloride and water (500 mL), and then dried over anhydrous magnesium sulfate and concentrated under reduced pressure. To an ethyl acetate solution (500 mL) of the residue, 5% palladium on carbon (1.1 g) was added, and the residue was hydrogenated. After the catalyst was filtered off, the resulting mixture was concentrated under reduced pressure and the residue was purified by silica gel chromatography (10% ethyl acetate in heptane) to give compound (T-9) (2.4 g, 5.9 mmol) as a colorless solid.

Second Step: Synthesis of Compound (T-10)

Lithium aluminum hydride (0.3 g, 7.9 mmol) was suspended in tetrahydrofuran (30 mL), and the resulting suspension was cooled in a dry ice-acetone bath. A tetrahydrofuran solution (5 mL) of compound (T-9) (2.3 g, 5.6 mmol) was added dropwise thereto, and the resulting mixture was stirred for 4 hours. After reaction completion, the reaction mixture was poured into a potassium sodium tartrate aqueous solution (100 mL), and the resulting mixture was stirred overnight. The resulting mixture was subjected to extraction with ethyl acetate (50 mL, three times). The combined organic layer was washed with a saturated aqueous solution (100 mL) of sodium chloride and water (100 mL), and then dried over anhydrous magnesium sulfate and concentrated under reduced pressure. The residue was purified by silica gel chromatography (10% ethyl acetate in toluene) to give compound (T-10) (1.0 g, 2.4 mmol) as a colorless solid.

Third Step: Synthesis of Compound (1-3-49)

Compound (1-3-49) was prepared in a manner similar to Synthesis Example 1. When 1.0 g of compound (T-10) was used as a starting material, an objective compound was obtained as a colorless needle crystal (0.6 g).

$^1$H-NMR (CDCl$_3$; δ ppm): 6.79 (td, 1H), 6.64 (t, 1H), 5.51 (s, 1H), 4.11-4.06 (m, 4H), 3.12 (ddd, J=3.8, 7.6-10.7 Hz, 1H), 2.73-2.63 (m, 2H), 2.16 (t, 2H), 2.04-1.88 (m, 3H), 1.77 (d, 2H), 1.68 (td, 1H), 1.44 (t, 3H), 1.35-1.25 (m, 4H), 1.17-1.13 (m, 3H), 1.05-0.93 (m, 3H), 0.87 (t, 3H).

$^{19}$F-NMR (δ ppm; CDCl$_3$): −142.83 (dd, J=7.6 Hz, 19.7 Hz, 1F), −160.10 (dd, J=7.4 Hz, 19.6 Hz, 1F).

Phase transition temperature; C 29.5 S 38.3 SA 40.5 N 105.8 I; maximum temperature (NI)=99.6° C.; dielectric anisotropy (Δ∈)=−5.41; optical anisotropy (Δn)=0.107; viscosity (η)=50.8 mPa·s.

The compounds described below can be prepared with referring to the methods in Synthesis Examples and section "2. Synthesis of compound (1)."

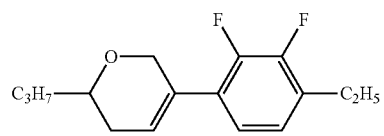
(1-2-01)

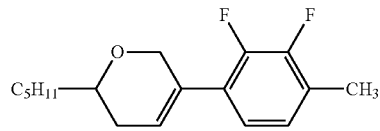
(1-2-02)

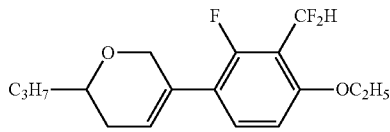
(1-2-03)

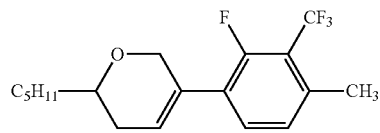
(1-2-04)

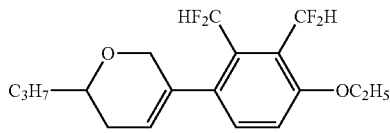
(1-2-05)

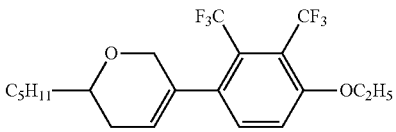
(1-2-06)

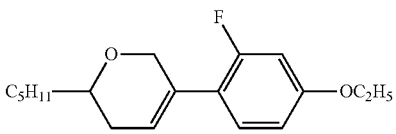
(1-2-07)

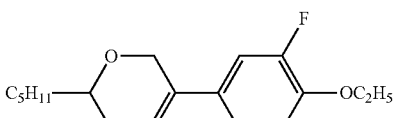
(1-2-08)

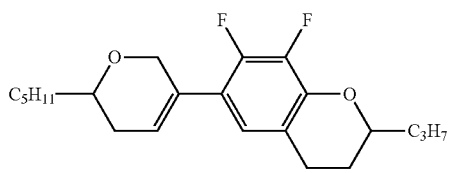
(1-2-09)

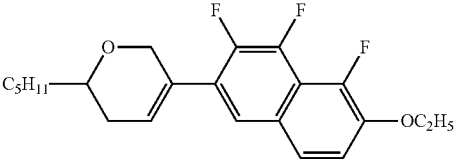
(1-2-10)

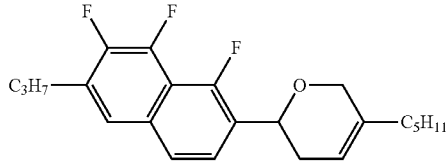
(1-2-11)

-continued (1-2-12)
(1-2-13)
(1-2-14)
(1-2-15)
(1-2-16)
(1-2-17)
(1-2-18)
(1-2-19)

-continued (1-2-20)
(1-2-21)
(1-2-22)
(1-2-23)
(1-2-24)
(1-2-25)
(1-2-26)
(1-2-27)
(1-2-28)
(1-2-29)

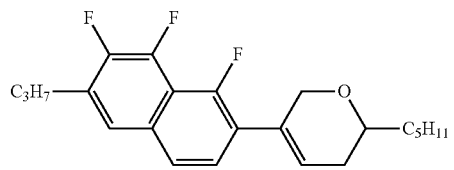
(1-2-30)
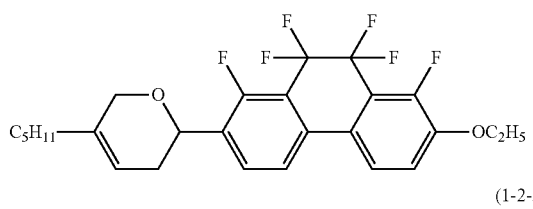
(1-2-31)
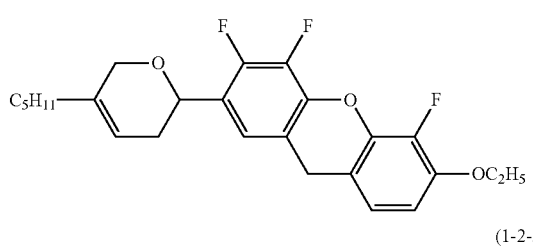
(1-2-32)
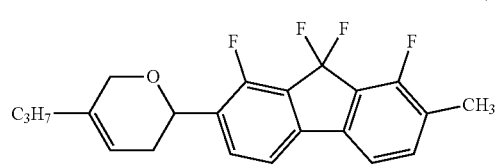
(1-2-33)
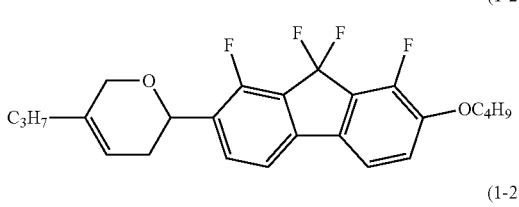
(1-2-34)
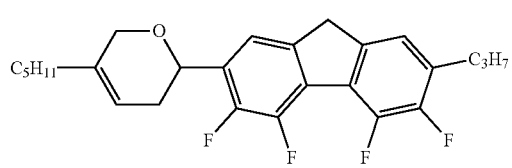
(1-2-35)
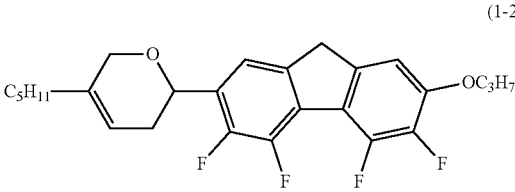
(1-2-36)
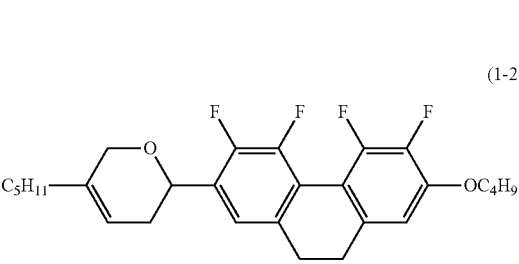
(1-2-37)
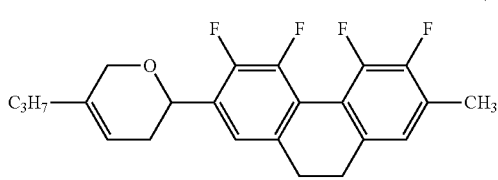
(1-2-38)
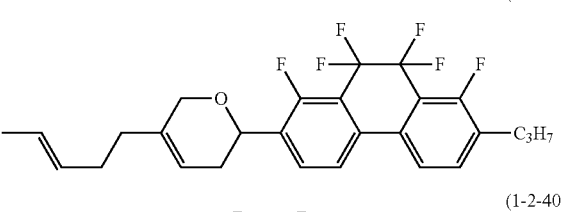
(1-2-39)
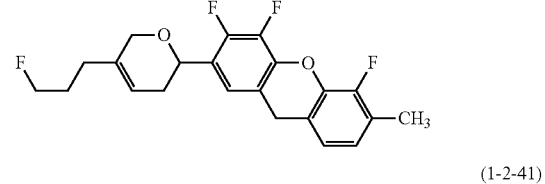
(1-2-40)
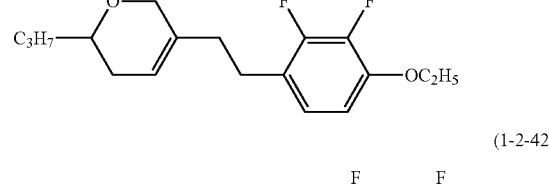
(1-2-41)
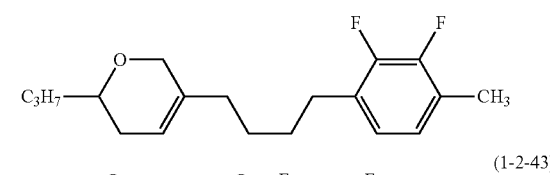
(1-2-42)
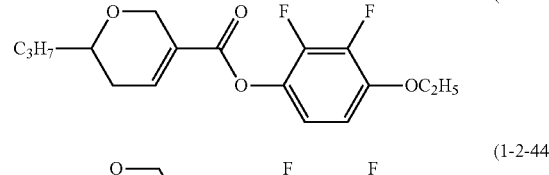
(1-2-43)
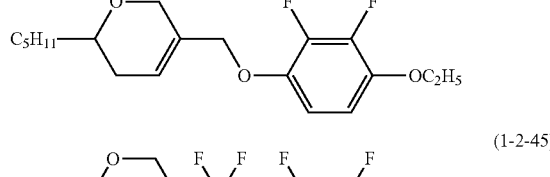
(1-2-44)
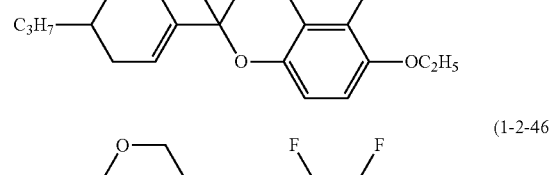
(1-2-45)
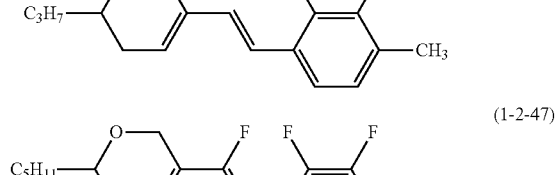
(1-2-46)
(1-2-47)

-continued (1-2-48)
(1-2-49)
(1-2-50)
(1-2-51)
(1-2-52)
(1-2-53)
(1-2-54)
(1-2-55)
(1-2-56)

-continued (1-2-57)
(1-2-58)
(1-2-59)
(1-2-60)
(1-2-61)
(1-2-62)
(1-2-63)
(1-2-64)
(1-2-65)

(1-2-66)
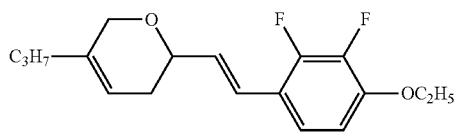
(1-2-67)
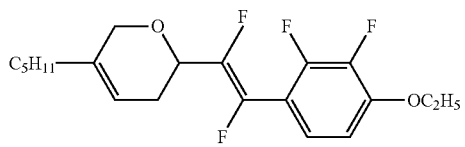
(1-2-68)
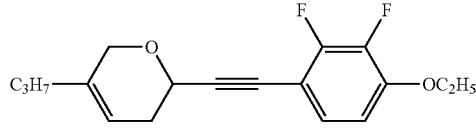
(1-2-69)
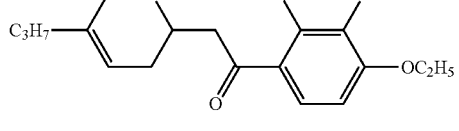
(1-2-70)
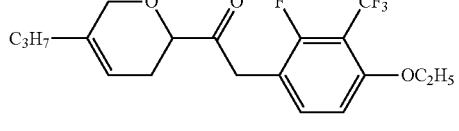
(1-2-71)
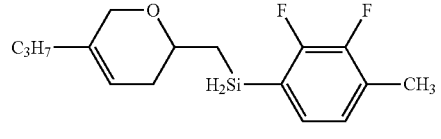
(1-2-72)
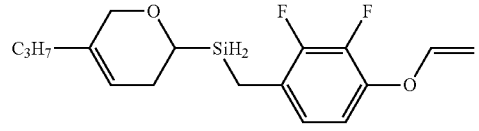
(1-2-73)
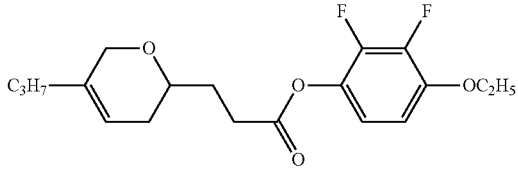
(1-2-74)
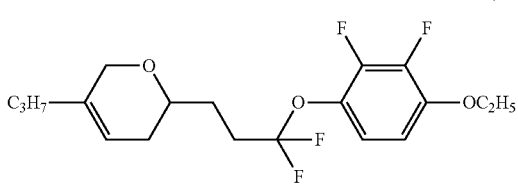
(1-2-75)
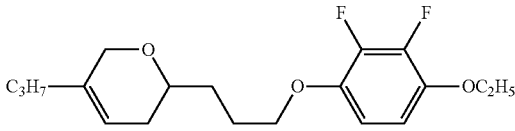
(1-2-76)
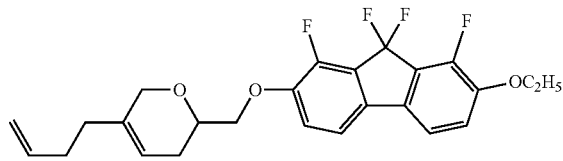
(1-2-77)
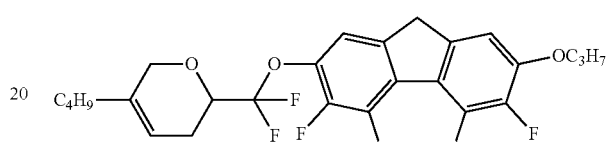
(1-2-78)
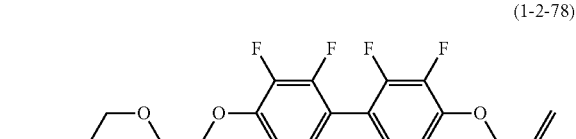
(1-2-79)
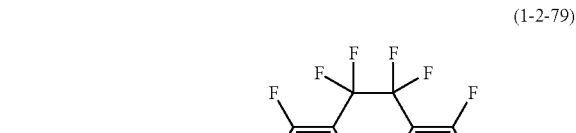
(1-2-80)
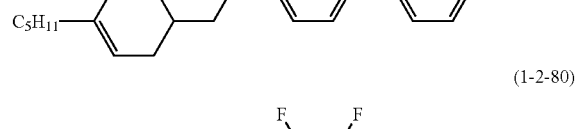
(1-3-01)
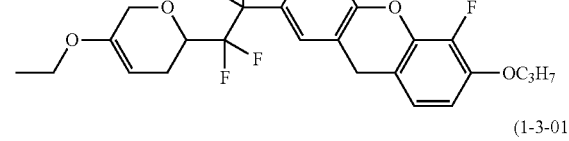
(1-3-02)
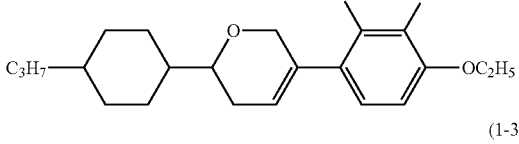
(1-3-03)
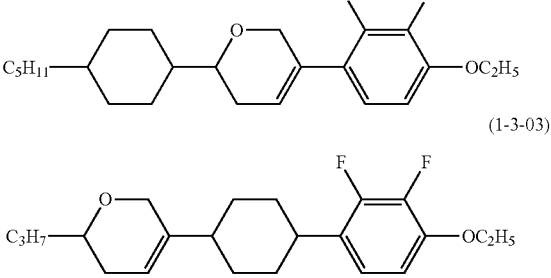

(1-3-04)
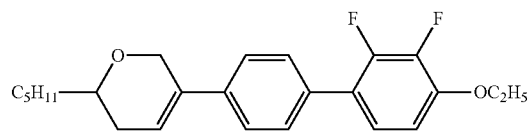
(1-3-05)
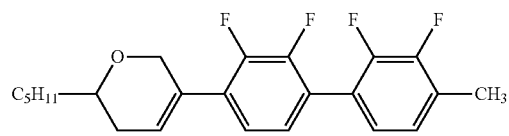
(1-3-06)
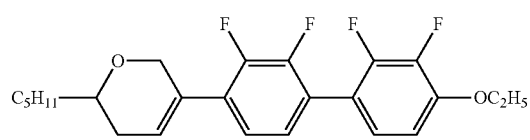
(1-3-07)
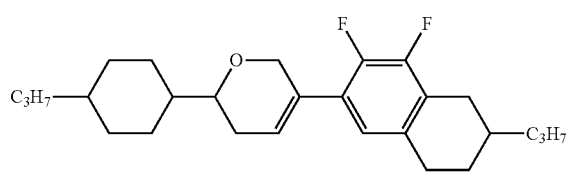
(1-3-8)
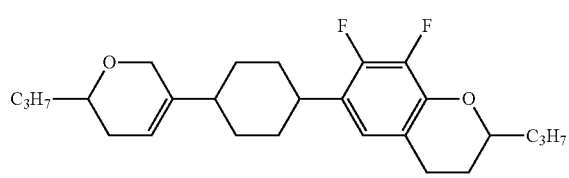
(1-3-9)
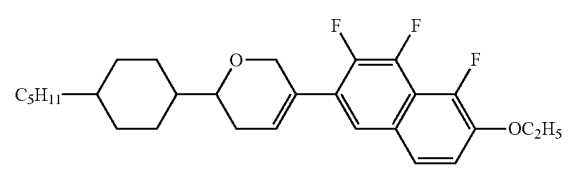
(1-3-10)
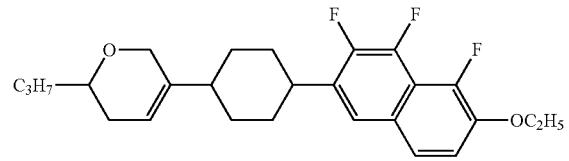
(1-3-11)
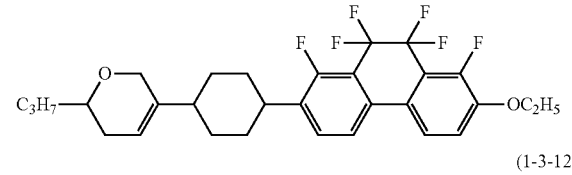
(1-3-12)
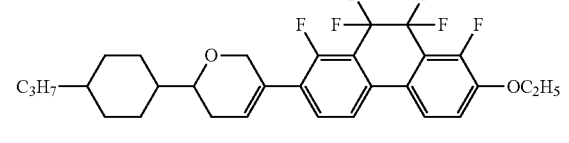
(1-3-13)
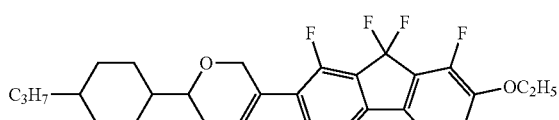
(1-3-14)
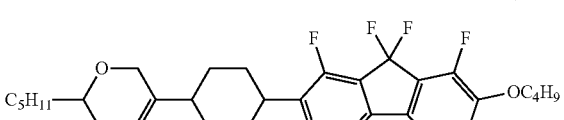
(1-3-15)
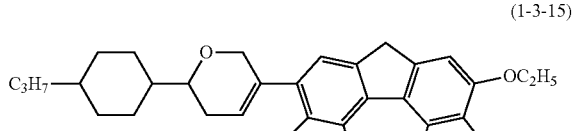
(1-3-16)
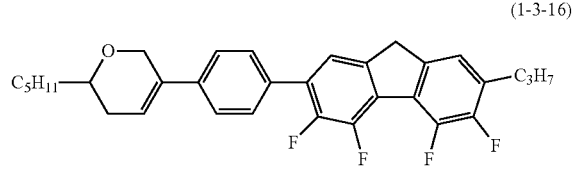
(1-3-17)
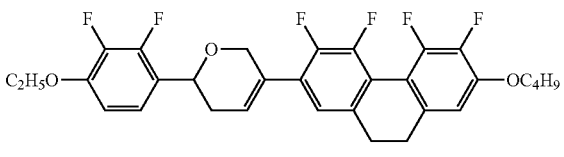
(1-3-18)
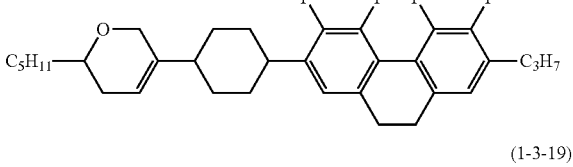
(1-3-19)
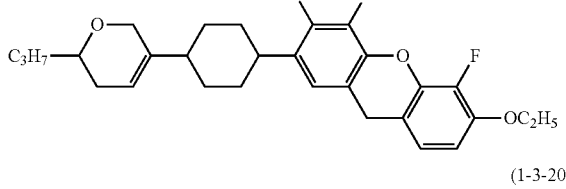
(1-3-20)
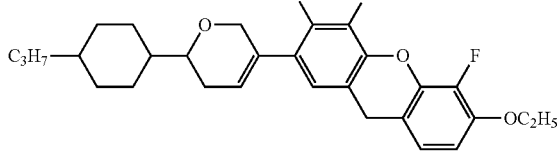
(1-3-21)
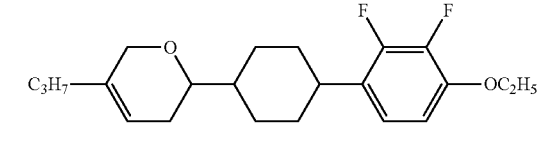

(1-3-22)
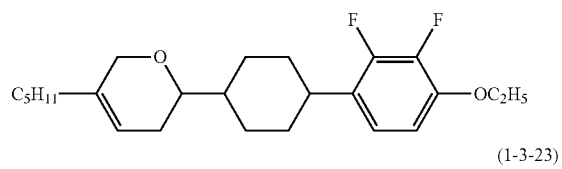
(1-3-23)
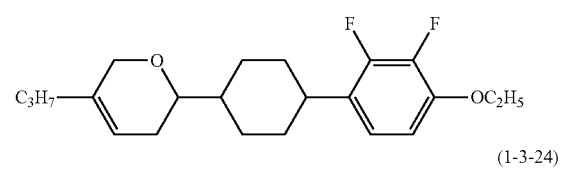
(1-3-24)
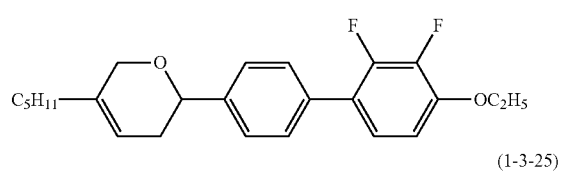
(1-3-25)
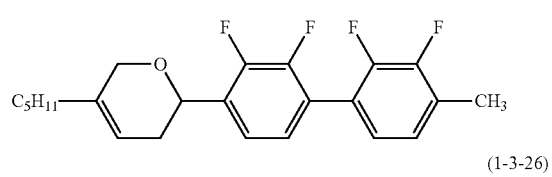
(1-3-26)
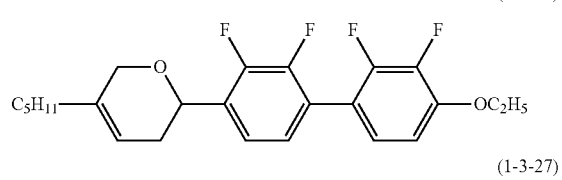
(1-3-27)
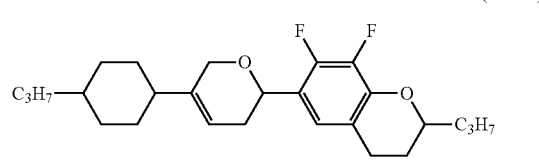
(1-3-28)
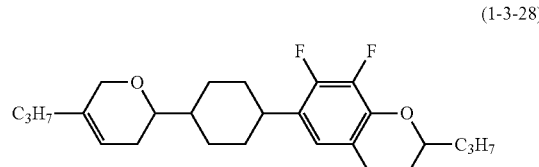
(1-3-29)
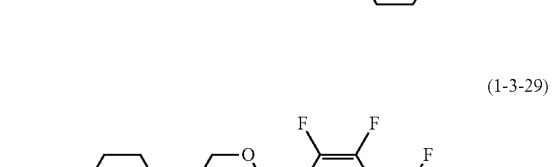
(1-3-30)
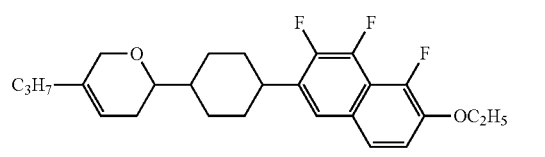
(1-3-31)
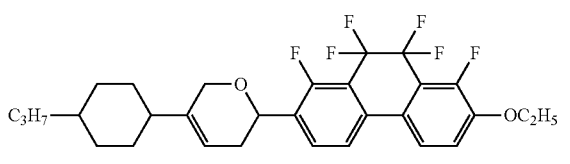
(1-3-32)
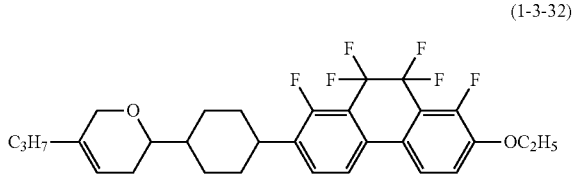
(1-3-33)
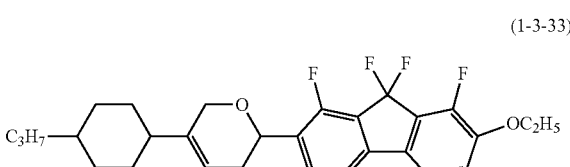
(1-3-34)
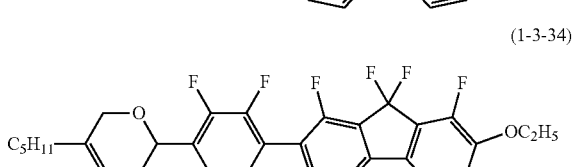
(1-3-35)
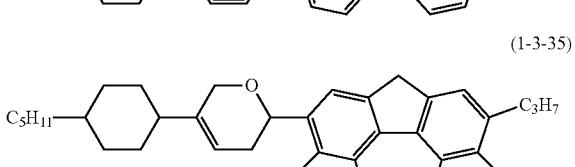
(1-3-36)
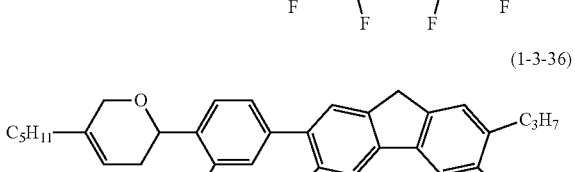
(1-3-37)
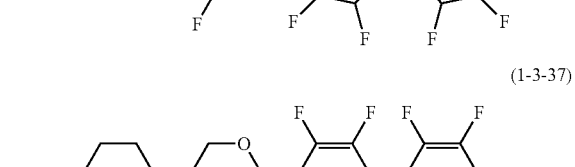
(1-3-38)
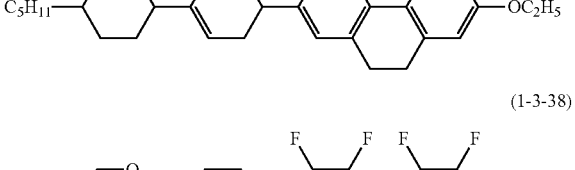
(1-3-39)
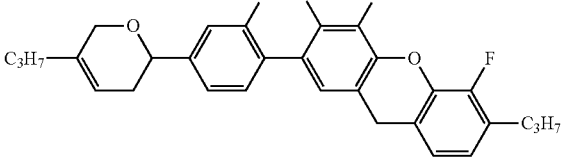

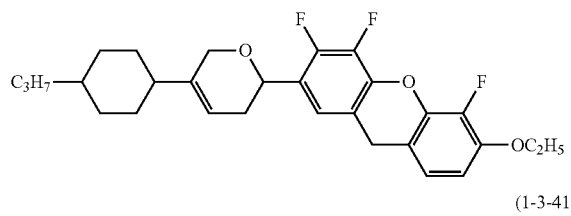 (1-3-40)
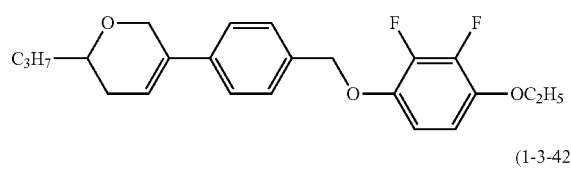 (1-3-41)
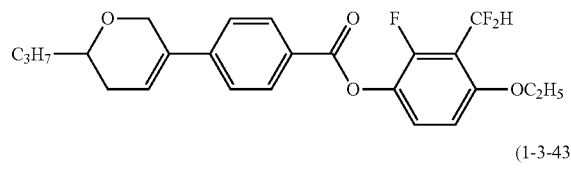 (1-3-42)
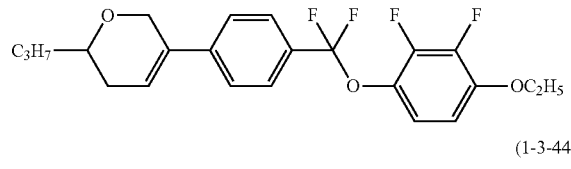 (1-3-43)
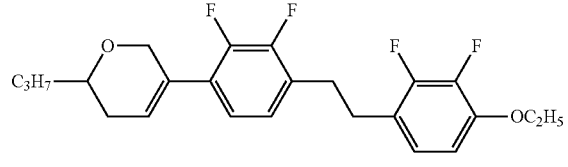 (1-3-44)
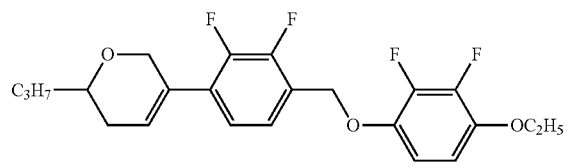 (1-3-45)
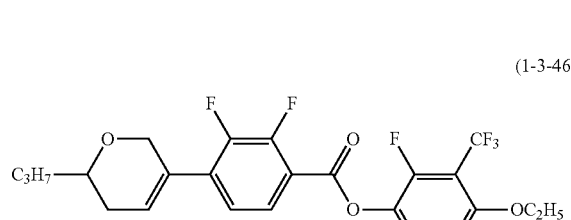 (1-3-46)
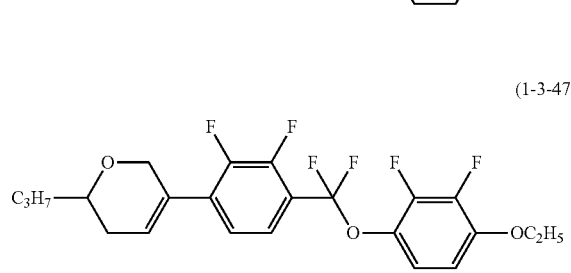 (1-3-47)
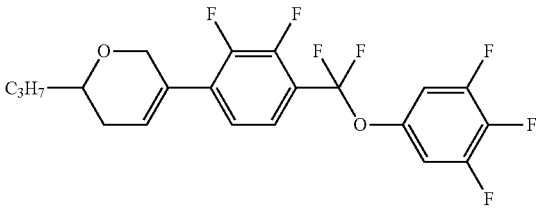 (1-3-48)
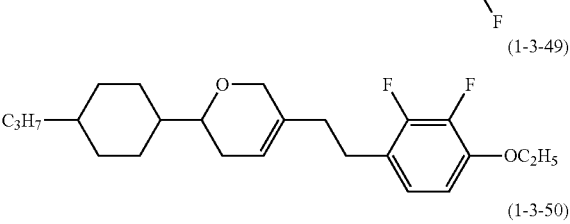 (1-3-49)
 (1-3-50)
 (1-3-51)
 (1-3-52)
 (1-3-53)
 (1-3-54)
 (1-3-55)
 (1-3-56)
 (1-3-57)
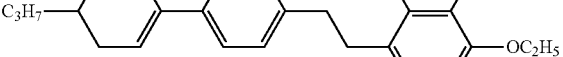

-continued
(1-3-58)
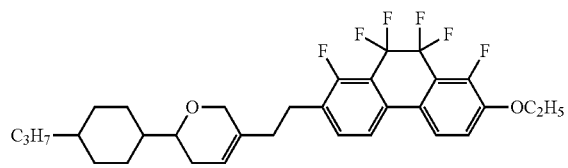
(1-3-59)
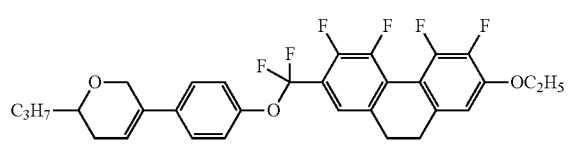
(1-3-60)
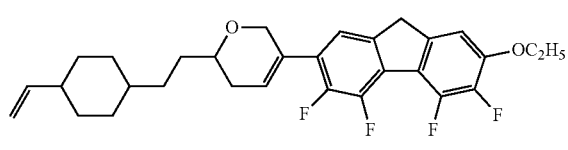
(1-3-61)
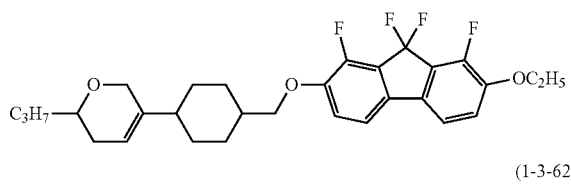
(1-3-62)
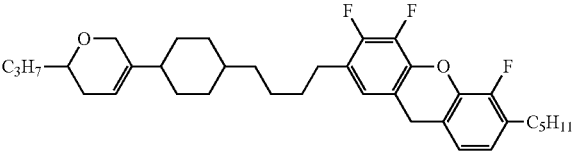
(1-3-63)
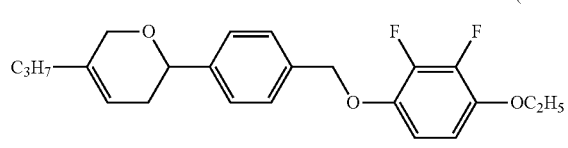
(1-3-64)
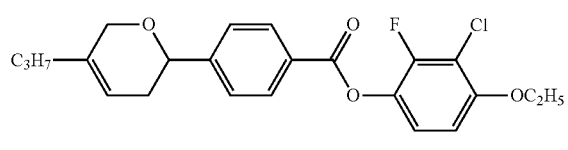
(1-3-65)
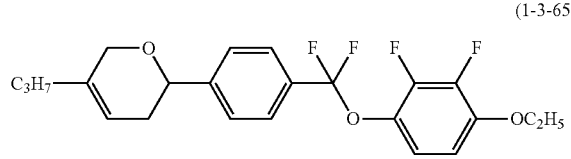
(1-3-66)
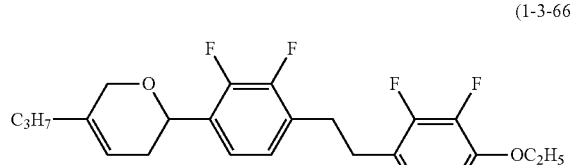
-continued
(1-3-67)
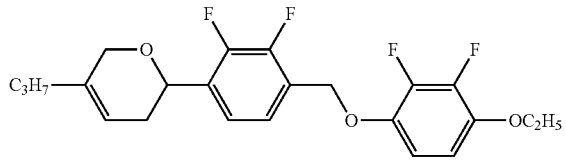
(1-3-68)
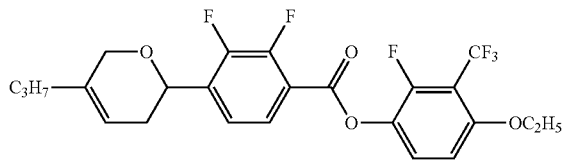
(1-3-69)
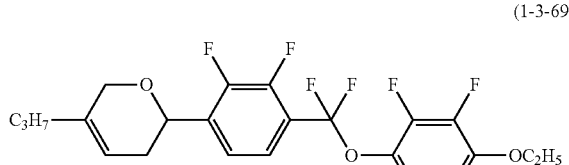
(1-3-70)
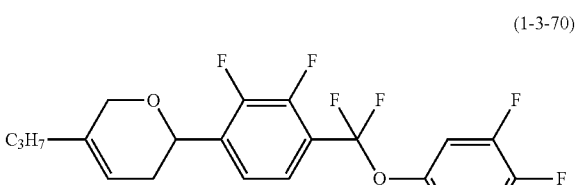
(1-3-71)
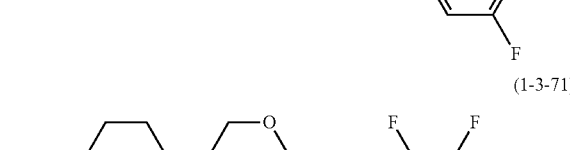
(1-3-72)
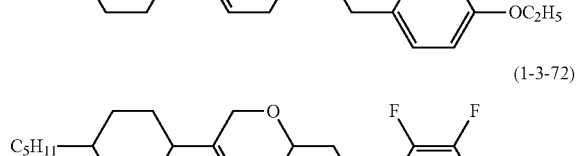
(1-3-73)
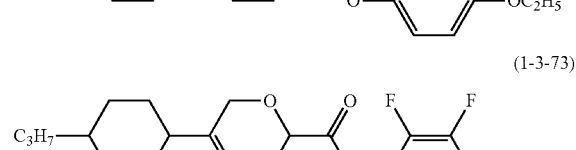
(1-3-74)
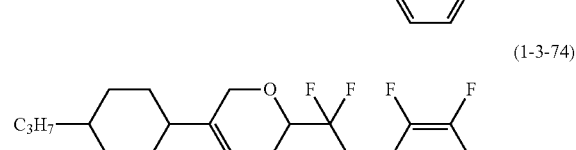
(1-3-75)
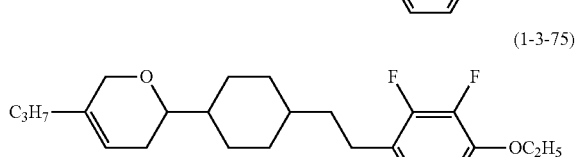

(1-3-76)
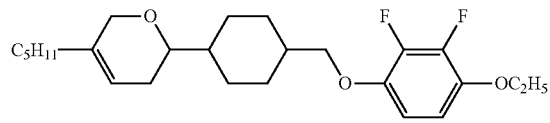
(1-3-77)
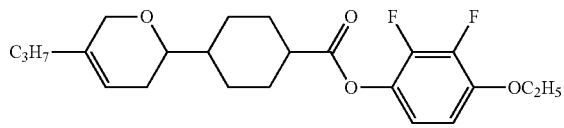
(1-3-78)
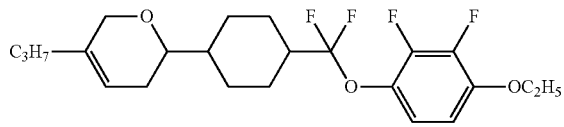
(1-3-79)
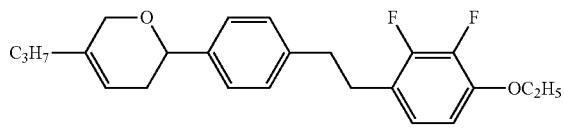
(1-3-80)
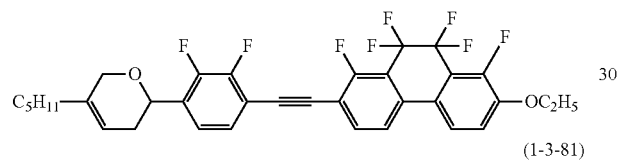
(1-3-81)
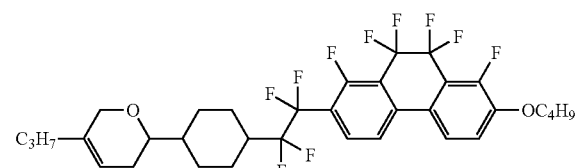
(1-3-82)
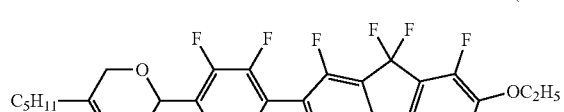
(1-3-83)
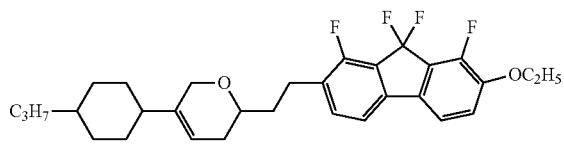
(1-3-84)
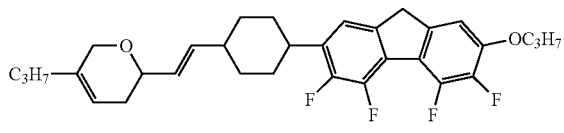
(1-3-85)
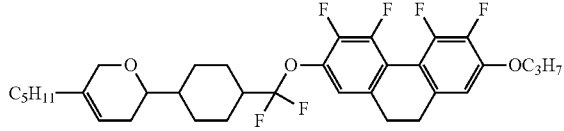
(1-3-86)
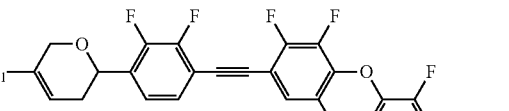
(1-4-01)
(1-4-02)
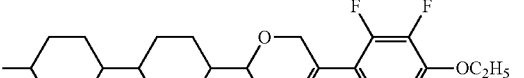
(1-4-03)
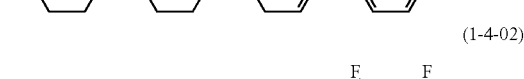
(1-4-04)
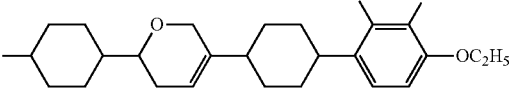
(1-4-05)
(1-4-06)
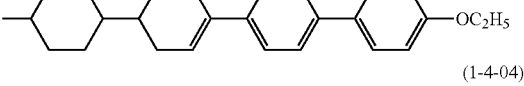
(1-4-07)
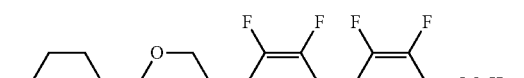
(1-4-08)
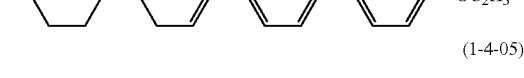
(1-4-09)
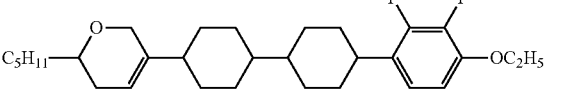
(1-4-10)

(1-4-11)
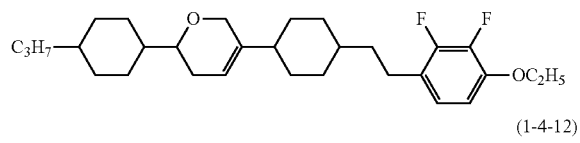
(1-4-12)
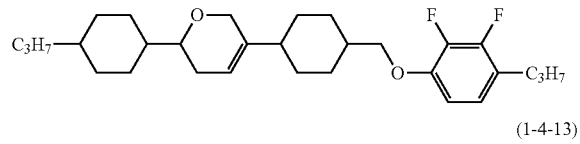
(1-4-13)
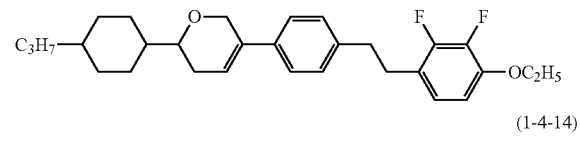
(1-4-14)
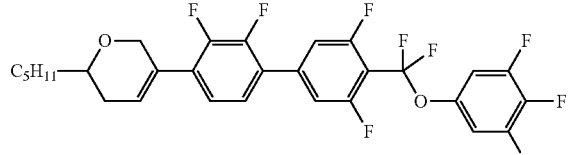
(1-4-15)
(1-4-16)
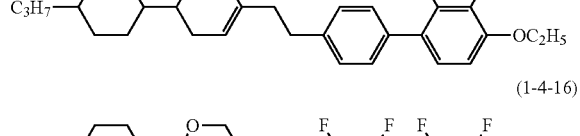
(1-4-17)
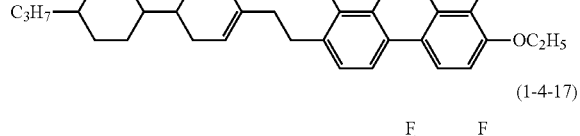
(1-4-18)
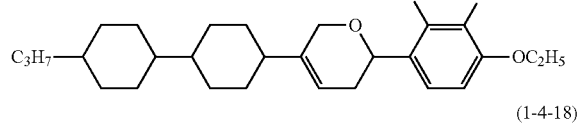
(1-4-19)
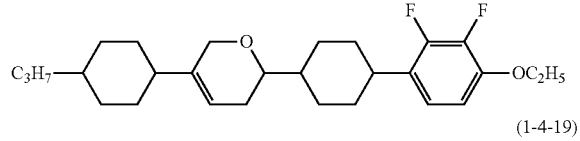
(1-4-20)
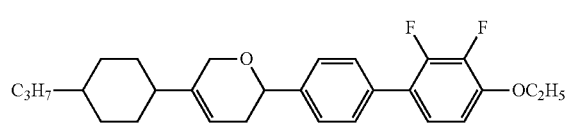
(1-4-21)
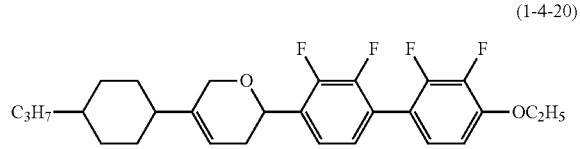
(1-4-22)
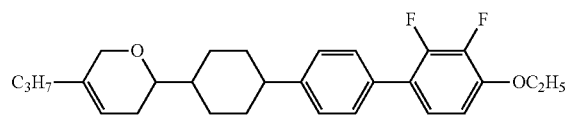
(1-4-23)
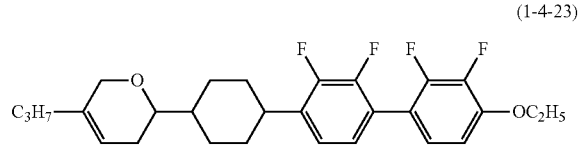
(1-4-24)
(1-4-25)
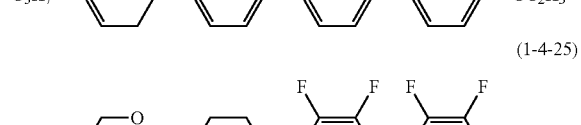
(1-4-26)
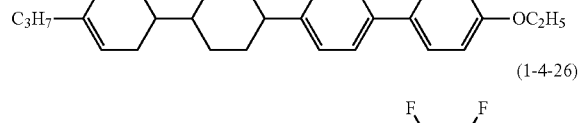
(1-4-27)
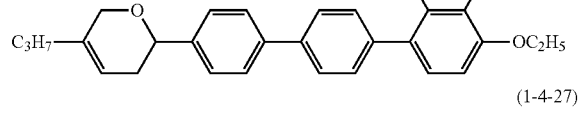
(1-4-28)
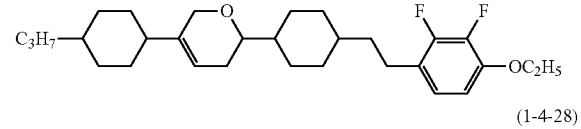
(1-4-29)
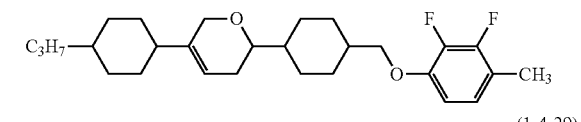
(1-4-30)
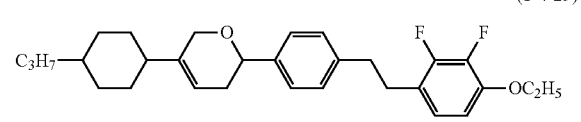
(1-4-31)
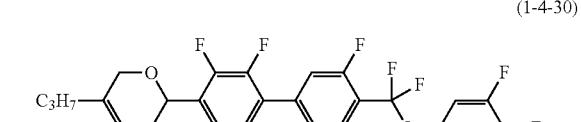
(1-4-32)
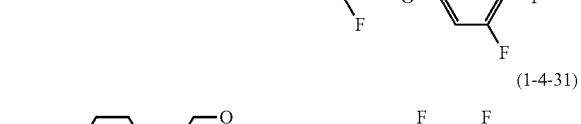

2. Example of Composition

The invention will be described in greater detail by way of Examples. The examples are exemplary embodiments and not intended to limit the scope of the invention. For example, the invention includes a mixture of the composition in Use Example 1 and the composition in Use Example 2 in addition to the compositions in Use Examples. The invention also includes a mixture prepared by mixing at least two compositions in Use Examples. Compounds in Use Examples were described using symbols according to definitions in Table 2 below. In Table 2, a configuration of 1,4-cyclohexylene is trans. A parenthesized number next to a symbolized compound in Use Examples corresponds to the chemical formula to which a compound belongs. A symbol (—) means a liquid crystal compound different from compounds (1) to (15). A proportion (percentage) of a liquid crystal compound was expressed in terms of weight percent (% by weight) based on the weight of the liquid crystal composition containing no additive. In a last part, values of physical properties of the composition are summarized. The physical properties were measured according to the methods described above, measured values are directly described (without extrapolation) as are.

TABLE 2

Method for Description of Compounds using Symbols $$R—(A_1)—Z_1—\ldots—Z_n—(A_n)—R'$$

| | Symbol |
|---|---|
| 1) Left-terminal Group R— | |
| $C_nH_{2n+1}—$ | n- |
| $C_nH_{2n+1}O—$ | nO- |
| $C_mH_{2m+1}OC_nH_{2n}—$ | mOn- |
| $CH_2=CH—$ | V- |
| $C_nH_{2n+1}—CH=CH—$ | nV- |
| $CH_2=CH—C_nH_{2n}—$ | Vn- |
| $C_mH_{2m+1}—CH=CH—C_nH_{2n}—$ | mVn- |
| $CF_2=CH—$ | VFF- |
| $CF_2=CH—C_nH_{2n}—$ | VFFn- |
| 2) Right-terminal Group —R' | |
| $—C_nH_{2n+1}$ | -n |
| $—OC_nH_{2n+1}$ | -On |
| $—COOCH_3$ | -EMe |
| $—CH=CH_2$ | -V |
| $—CH=CH—C_nH_{2n+1}$ | -Vn |
| $—C_nH_{2n}—CH=CH_2$ | -nV |
| $—C_mH_{2m}—CH=CH—C_nH_{2n+1}$ | -mVn |
| $—CH=CF_2$ | -VFF |
| $—F$ | -F |
| $—Cl$ | -CL |
| $—OCF_3$ | -OCF3 |
| $—OCF_2H$ | -OCF2H |
| $—CF_3$ | -CF3 |
| $—OCH=CH—CF_3$ | -OVCF3 |
| $—C≡N$ | -C |
| 3) Bonding Group —Zn— | |
| $—C_nH_{2n}—$ | n |
| $—COO—$ | E |
| $—CH=CH—$ | V |
| $—CH_2O—$ | 1O |
| $—OCH_2—$ | O1 |
| $—CF_2O—$ | X |
| $—C≡C—$ | T |
| 4) Ring Structure —An— | |
| 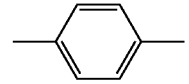 | H |

TABLE 2-continued

Method for Description of Compounds using Symbols $$R—(A_1)—Z_1—\ldots—Z_n—(A_n)—R'$$

| | Symbol |
|---|---|
| 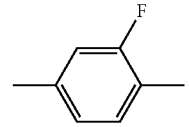 | B |
| 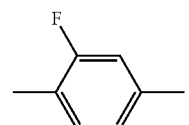 | B(F) |
| 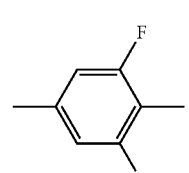 | B(2F) |
| 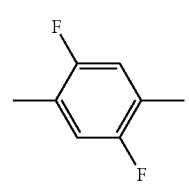 | B(F,F) |
| 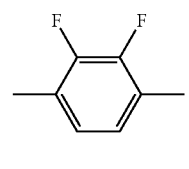 | B(2F,5F) |
| 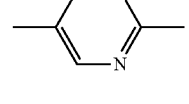 | B(2F,3F) |
| 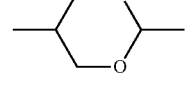 | Py |
| 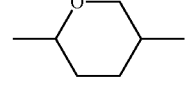 | G |
| 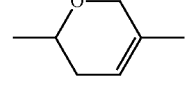 | Dh |

TABLE 2-continued

Method for Description of Compounds using Symbols

R—(A₁)—Z₁— . . . —Zₙ—(Aₙ)—R'

| | Symbol |
|---|---|
| 5) Examples of Description | |
| Example 1 | 3-HDprB(2F,3F)-O2 |

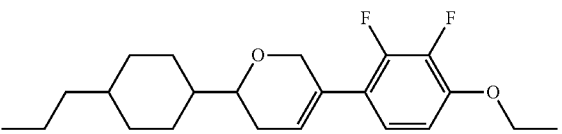 [SMILES: CCCC1CCC(C2CC=C(c3ccc(OCC)c(F)c3F)CO2)CC1]

| Example 2 | 3-BB(F,F)XB(F,F)-F |
|---|---|

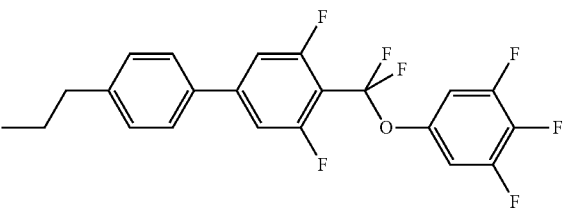 [SMILES: CCCc1ccc(-c2cc(F)c(C(F)(F)Oc3cc(F)c(F)c(F)c3)c(F)c2)cc1]

| Example 3 | 3-HH-4 |
|---|---|

| Example 4 | 3-HH-V |
|---|---|

Use Example 1

| 3-HDprB(2F,3F)-O2 | (1-1) | 9% |
|---|---|---|
| 3-HB-O2 | (2-5) | 10% |
| 5-HB-CL | (12-2) | 10% |
| 3-HBB(F,F)-F | (13-24) | 9% |
| 3-PyB(F)-F | (12-15) | 10% |
| 5-PyB(F)-F | (12-15) | 10% |
| 3-PyBB-F | (13-80) | 10% |
| 4-PyBB-F | (13-80) | 9% |
| 5-PyBB-F | (13-80) | 9% |
| 5-HBB(F)B-2 | (4-5) | 7% |
| 5-HBB(F)B-3 | (4-5) | 7% |

NI=97.1° C.; η=40.8 mPa·s; Δn=0.184; Δ∈=7.5.

Use Example 2

| 3-HDpr2B(2F,3F)-O2 | (1-1) | 8% |
|---|---|---|
| 2-HB-C | (15-1) | 5% |
| 3-HB-C | (15-1) | 11% |
| 3-HB-O2 | (2-5) | 13% |
| 2-BTB-1 | (2-10) | 3% |
| 3-HHB-F | (13-1) | 3% |
| 3-HHB-1 | (3-1) | 8% |
| 3-HHB-O1 | (3-1) | 3% |
| 3-HHB-3 | (3-1) | 12% |
| 3-HHEB-F | (13-10) | 4% |
| 5-HHEB-F | (13-10) | 4% |
| 2-HHB(F)-F | (13-2) | 7% |
| 3-HHB(F)-F | (13-2) | 7% |
| 5-HHB(F)-F | (13-2) | 7% |
| 3-HHB(F,F)-F | (13-3) | 5% |

Use Example 3

| 5-DprB(2F,3F)-O2 | (1-1) | 9% |
|---|---|---|
| 7-HB(F,F)-F | (12-4) | 3% |
| 3-HB-O2 | (2-5) | 7% |
| 2-HHB(F)-F | (13-2) | 8% |
| 3-HHB(F)-F | (13-2) | 9% |
| 5-HHB(F)-F | (13-2) | 9% |
| 2-HBB(F)-F | (13-23) | 8% |
| 3-HBB(F)-F | (13-23) | 9% |
| 5-HBB(F)-F | (13-23) | 14% |
| 2-HBB-F | (13-22) | 5% |
| 3-HBB-F | (13-22) | 4% |
| 5-HBB-F | (13-22) | 3% |
| 3-HBB(F,F)-F | (12-24) | 5% |
| 5-HBB(F,F)-F | (12-24) | 7% |

NI=79.3° C.; η=25.5 mPa·s; Δn=0.114; Δ∈=5.0.

Use Example 4

| 5-DprB(2F,3F)B(2F,3F)-O2 | (1-1) | 10% |
|---|---|---|
| 5-HB-CL | (12-2) | 10% |
| 3-HH-4 | (2-1) | 12% |
| 3-HH-5 | (2-1) | 4% |
| 3-HHB-F | (13-1) | 4% |
| 3-HHB-CL | (13-1) | 3% |
| 4-HHB-CL | (13-1) | 4% |
| 3-HHB(F)-F | (13-2) | 10% |
| 4-HHB(F)-F | (13-2) | 9% |
| 5-HHB(F)-F | (13-2) | 10% |
| 7-HHB(F)-F | (13-2) | 8% |
| 5-HBB(F)-F | (13-23) | 4% |
| 1O1-HBBH-5 | (4-1) | 3% |
| 4-HHBB(F,F)-F | (14-6) | 3% |
| 5-HHBB(F,F)-F | (14-6) | 3% |
| 3-HH2BB(F,F)-F | (14-15) | 3% |

Use Example 5

| 5-DprHHB(2F,3F)-O2 | (1-1) | 3% |
|---|---|---|
| 3-HHB(F,F)-F | (13-3) | 9% |
| 3-H2HB(F,F)-F | (13-15) | 8% |
| 4-H2HB(F,F)-F | (13-15) | 8% |
| 5-H2HB(F,F)-F | (13-15) | 8% |
| 3-HBB(F,F)-F | (12-24) | 18% |
| 5-HBB(F,F)-F | (12-24) | 20% |
| 3-H2BB(F,F)-F | (13-27) | 10% |
| 5-HHBB(F,F)-F | (14-6) | 3% |
| 5-HHEBB-F | (14-17) | 2% |
| 3-HH2BB(F,F)-F | (14-15) | 3% |
| 1O1-HBBH-4 | (4-1) | 4% |
| 1O1-HBBH-5 | (4-1) | 4% |

Use Example 6

| | | |
|---|---|---|
| 3-HDprB(2F,3F)-O2 | (1-1) | 10% |
| 5-HB-F | (12-2) | 12% |
| 6-HB-F | (12-2) | 9% |
| 7-HB-F | (12-2) | 7% |
| 2-HHB-OCF3 | (13-1) | 5% |
| 3-HHB-OCF3 | (13-1) | 5% |
| 4-HHB-OCF3 | (13-1) | 7% |
| 5-HHB-OCF3 | (13-1) | 4% |
| 3-HH2B-OCF3 | (13-4) | 4% |
| 5-HH2B-OCF3 | (13-4) | 4% |
| 3-HHB(F,F)-OCF2H | (13-3) | 4% |
| 3-HHB(F,F)-OCF3 | (13-3) | 4% |
| 3-HH2B(F)-F | (13-5) | 3% |
| 3-HBB(F)-F | (13-23) | 8% |
| 5-HBB(F)-F | (13-23) | 8% |
| 5-HBBH-3 | (4-1) | 3% |
| 3-HB(F)BH-3 | (4-2) | 3% |

NI=90.8° C.; η=17.3 mPa·s; Δn=0.095; Δ∈=3.6.

Use Example 7

| | | |
|---|---|---|
| 3-HDpr2B(2F,3F)-O2 | (1-1) | 9% |
| 5-HB-CL | (12-2) | 11% |
| 3-HH-4 | (2-1) | 8% |
| 3-HHB-1 | (3-1) | 5% |
| 3-HHB(F,F)-F | (13-3) | 6% |
| 3-HBB(F,F)-F | (13-24) | 15% |
| 5-HBB(F,F)-F | (13-24) | 13% |
| 3-HHEB(F,F)-F | (13-12) | 10% |
| 4-HHEB(F,F)-F | (13-12) | 3% |
| 5-HHEB(F,F)-F | (13-12) | 3% |
| 2-HBEB(F,F)-F | (13-39) | 3% |
| 3-HBEB(F,F)-F | (13-39) | 5% |
| 5-HBEB(F,F)-F | (13-39) | 3% |
| 3-HHBB(F,F)-F | (14-6) | 6% |

Use Example 8

| | | |
|---|---|---|
| 5-DprB(2F,3F)-O2 | (1-1) | 7% |
| 5-HB-CL | (12-2) | 4% |
| 3-HHB-OCF3 | (13-1) | 5% |
| 3-H2HB-OCF3 | (13-13) | 5% |
| 5-H4HB-OCF3 | (13-19) | 15% |
| V-HHB(F)-F | (13-2) | 5% |
| 3-HHB(F)-F | (13-2) | 5% |
| 5-HHB(F)-F | (13-2) | 5% |
| 3-H4HB(F,F)-CF3 | (13-21) | 8% |
| 5-H4HB(F,F)-CF3 | (13-21) | 10% |
| 5-H2HB(F,F)-F | (13-15) | 5% |
| 5-H4HB(F,F)-F | (13-21) | 7% |
| 2-H2BB(F)-F | (13-26) | 5% |
| 3-H2BB(F)-F | (13-26) | 9% |
| 3-HBEB(F,F)-F | (13-39) | 5% |

NI=70.0° C.; η=25.8 mPa·s; Δn=0.091; Δ∈=7.9.

Use Example 9

| | | |
|---|---|---|
| 5-DprB(2F,3F)B(2F,3F)-O2 | (1-1) | 8% |
| 5-HB-CL | (12-2) | 14% |
| 7-HB(F,F)-F | (12-4) | 3% |
| 3-HH-4 | (2-1) | 9% |
| 3-HH-5 | (2-1) | 5% |
| 3-HB-O2 | (2-5) | 15% |
| 3-HHB-1 | (3-1) | 8% |
| 3-HHB-O1 | (3-1) | 6% |
| 2-HHB(F)-F | (13-2) | 7% |
| 3-HHB(F)-F | (13-2) | 6% |
| 5-HHB(F)-F | (13-2) | 7% |
| 3-HHB(F,F)-F | (13-3) | 6% |
| 3-H2HB(F,F)-F | (13-15) | 3% |
| 4-H2HB(F,F)-F | (13-15) | 3% |

Use Example 10

| | | |
|---|---|---|
| 5-DprHHB(2F,3F)-O2 | (1-1) | 3% |
| 5-HB-CL | (12-2) | 3% |
| 7-HB(F)-F | (12-3) | 7% |
| 3-HH-4 | (2-1) | 9% |
| 3-HH-EMe | (2-2) | 23% |
| 3-HHEB-F | (13-10) | 8% |
| 5-HHEB-F | (13-10) | 7% |
| 3-HHEB(F,F)-F | (13-12) | 8% |
| 4-HHEB(F,F)-F | (13-12) | 5% |
| 4-HGB(F,F)-F | (13-103) | 5% |
| 5-HGB(F,F)-F | (13-103) | 6% |
| 2-H2GB(F,F)-F | (13-106) | 4% |
| 3-H2GB(F,F)-F | (13-106) | 5% |
| 5-GHB(F,F)-F | (13-109) | 7% |

Use Example 11

| | | |
|---|---|---|
| 3-HDprB(2F,3F)-O2 | (1-1) | 9% |
| 1V2-BEB(F,F)-C | (15-15) | 6% |
| 3-HB-C | (15-1) | 14% |
| 2-BTB-1 | (2-10) | 10% |
| 5-HH-VFF | (2-1) | 25% |
| 3-HHB-1 | (3-1) | 4% |
| VFF-HHB-1 | (3-1) | 8% |
| VFF2-HHB-1 | (3-1) | 11% |
| 3-H2BTB-2 | (3-17) | 5% |
| 3-H2BTB-3 | (3-17) | 4% |
| 3-H2BTB-4 | (3-17) | 4% |

NI=90.8° C.; η=16.1 mPa·s; Δn=0.135; Δ∈=6.0.

Use Example 12

| | | |
|---|---|---|
| 3-HDpr2B(2F,3F)-O2 | (1-1) | 9% |
| 5-HB(F)B(F,F)XB(F,F)-F | (14-41) | 5% |
| 3-BB(F)B(F,F)XB(F,F)-F | (14-47) | 4% |
| 4-BB(F)B(F,F)XB(F,F)-F | (14-47) | 7% |
| 5-BB(F)B(F,F)XB(F,F)-F | (14-47) | 3% |
| 3-HH-V | (2-1) | 38% |
| 3-HH-V1 | (2-1) | 7% |
| 3-HHEH-5 | (3-13) | 3% |
| 3-HHB-1 | (3-1) | 3% |
| V-HHB-1 | (3-1) | 3% |
| V2-BB(F)B-1 | (3-6) | 5% |
| 1V2-BB-F | (12-1) | 3% |
| 3-BB(F,F)XB(F,F)-F | (13-97) | 7% |
| 3-HHBB(F,F)-F | (14-6) | 3% |

Use Example 13

| | | |
|---|---|---|
| 5-DprB(2F,3F)-O2 | (1-1) | 10% |
| 3-GB(F)B(F,F)XB(F,F)-F | (14-57) | 3% |
| 3-BB(F)B(F,F)XB(F,F)-F | (14-47) | 3% |
| 4-BB(F)B(F,F)XB(F,F)-F | (14-47) | 3% |
| 5-BB(F)B(F,F)XB(F,F)-F | (14-47) | 3% |
| 3-HH-V | (2-1) | 40% |
| 3-HH-V1 | (2-1) | 7% |
| 3-HHEH-5 | (3-13) | 3% |
| 3-HHB-1 | (3-1) | 3% |
| V-HHB-1 | (3-1) | 4% |
| V2-BB(F)B-1 | (3-6) | 5% |
| 1V2-BB-F | (12-1) | 3% |
| 3-BB(F,F)XB(F,F)-F | (13-97) | 5% |
| 3-GB(F,F)XB(F,F)-F | (13-113) | 5% |
| 3-HHBB(F,F)-F | (14-6) | 3% |

NI=73.3° C.; η=11.6 mPa·s; Δn=0.098; Δ∈=4.9.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

INDUSTRIAL APPLICABILITY

A liquid crystal compound of the invention has good physical properties. A liquid crystal composition containing the liquid crystal compound can be widely used in a liquid crystal display device for a personal computer, a television and so forth.

What is claimed is:

1. A compound represented by formula (1):

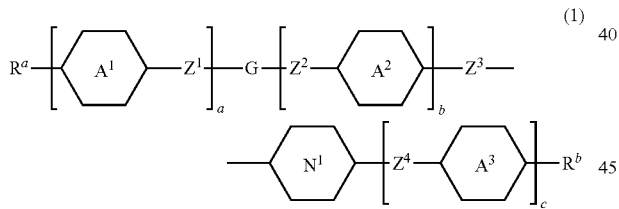

wherein, in formula (1), $R^a$ and $R^b$ are independently hydrogen or alkyl having 1 to 10 carbons, and in the alkyl, at least one —CH$_2$— may be replaced by —O— or —S—, —CO— or —SiH$_2$—, at least one —CH$_2$CH$_2$— may be replaced by —CH=CH— or —C≡C—, and in the groups, at least one hydrogen may be replaced by fluorine or chlorine, and $R^b$ may be fluorine, chlorine, —C≡N or —C≡C—C≡N;

ring $A^1$, ring $A^2$ and ring $A^3$ are independently 1,4-cyclohexylene, decahydronaphthalene-2,6-diyl or 1,4-phenylene, and in the groups, at least one —CH$_2$— may be replaced by —O—, —S—, —CO— or —SiH$_2$—, at least one —CH$_2$CH$_2$— may be replaced by —CH=CH— or —CH=N—, and in the divalent groups, at least one hydrogen may be replaced by fluorine, chlorine, —C≡N, —CF$_3$, —CHF$_2$, —CH$_2$F, —OCF$_3$, —OCHF$_2$ or —OCH$_2$F; and ring $N^1$ is 1,4-cyclohexylene, decahydronaphthalene-2,6-diyl, 1,2,3,4-tetrahydronaphthalene-2,6-diyl, 2,6,7-trioxabicyclo[2.2.2]octane-1,4-diyl, 1,4-phenylene, naphthalene-2,6-diyl, 9,10-dihydrophenanthrene-2,7-diyl, 9H-xanthene-2,6-diyl or 9H-fluorene-2,7-diyl, and in the groups, at least one —CH$_2$— may be replaced by —O—, —S—, —CO— or —SiH$_2$—, at least one —CH$_2$CH$_2$— may be replaced by —CH=CH— or —CH=N—, and in the divalent groups, at least one hydrogen may be replaced by fluorine, chlorine, —C≡N, —CF$_3$, —CHF$_2$, —CH$_2$F, —OCF$_3$, —OCHF$_2$ or —OCH$_2$F;

G is a divalent group represented by formula (pr-1) or (pr-2);

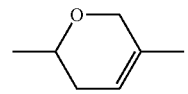

(pr-1)

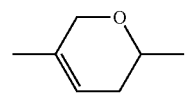

(pr-2)

wherein, $Z^1$ and $Z^2$ are independently a single bond or alkylene having 1 to 6 carbons, and in the alkylene, at least one —CH$_2$— may be replaced by —O—, —S—, —CO— or —SiH$_2$—, one or two pieces of —CH$_2$CH$_2$— may be replaced by —C≡C—, and in the divalent groups, at least one hydrogen may be replaced by fluorine or chlorine;

$Z^3$ and $Z^4$ are independently a single bond or alkylene having 1 to 6 carbons, and in the alkylene, at least one —CH$_2$— may be replaced by —O—, —S—, —CO— or —SiH$_2$—, one or two pieces of —CH$_2$CH$_2$— may be replaced by —CH=CH— or —C≡C—, and in the divalent groups, at least one hydrogen may be replaced by fluorine or chlorine;

a, b and c are independently 0, 1 or 2, and a sum of a, b and c is an integer from 0 to 3;

when $R^a$ is —C$_3$H$_7$, $R^b$ is —OC$_2$H$_5$, a is 1, b and c are 0, ring $A^1$ is tetrahydropyran-2,5-diyl, $Z^1$ and $Z^3$ are a single bond and ring $N^1$ is 2,3-difluoro-1,4-phenylene, G is a divalent group represented by formula (pr-2);

when $R^a$ is —C$_5$H$_{11}$, $R^b$ is —OC$_2$H$_5$, a, b and c are 0, $Z^3$ is a single bond and ring $N^1$ is 2,3-difluoro-1,4-phenylene, G is a divalent group represented by formula (pr-2); and when $R^a$ is —CH=CH$_2$ or —C$_2$H$_5$, $R^b$ is —OC$_2$H$_5$, a, b and c are 0, $Z^3$ is a single bond and ring $N^1$ is 2,3-difluoro-1,4-phenylene, G is a divalent group represented by formula (pr-1).

2. The compound according to claim 1, represented by formula (1-1):

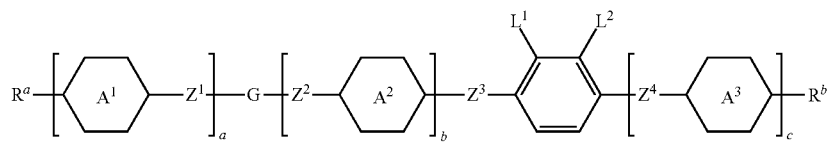

(1-1)

wherein, in formula (1-1),

R$^a$ and R$^b$ are independently hydrogen or alkyl having 1 to 10 carbons, alkoxy having 1 to 9 carbons, alkoxyalkyl having 2 to 9 carbons, alkenyl having 2 to 10 carbons or alkenyloxy having 2 to 9 carbons, and R$^b$ may be fluorine, chlorine, —C≡N, —C≡C—C≡N, alkyl having 1 to 10 carbons in which at least one hydrogen is replaced by fluorine, or chlorine or alkoxy having 1 to 9 carbons in which at least one hydrogen is replaced by fluorine or chlorine;

ring A$^1$, ring A$^2$ and ring A$^3$ are independently 1,4-cyclohexylene, decahydronaphthalene-2,6-diyl or 1,4-phenylene, and in the groups, at least one —CH$_2$— may be replaced by —O—, —S—, —CO— or —SiH$_2$—, at least one —CH$_2$CH$_2$— may be replaced by —CH=CH— or —CH=N—, and in the divalent groups, at least one hydrogen may be replaced by fluorine, chlorine, —C≡N, —CF$_3$, —CHF$_2$, —CH$_2$F, —OCF$_3$, —OCHF$_2$ or —OCH$_2$F;

G is a divalent group represented by formula (pr-1) or (pr-2);

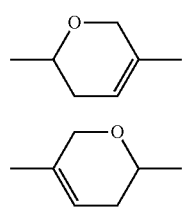

(pr-1)

(pr-2)

wherein,

Z$^1$, Z$^2$, Z$^3$ and Z$^4$ are independently a single bond, —COO—, —COO—, —CH$_2$O—, —OCH$_2$—, —CF$_2$O—, —OCF$_2$— or —CH$_2$CH$_2$—;

L$^1$ and L$^2$ are independently fluorine, chlorine, —CF$_3$, —CHF$_2$, —CH$_2$F, —OCF$_3$, —OCHF$_2$ or —OCH$_2$F;

a, b and c are independently 0, 1 or 2, and a sum of a, b and c is 0, 1 or 2;

when R$^a$ is —C$_3$H$_7$, R$^b$ is —OC$_2$H$_5$, a is 1, b and c are 0, ring A$^1$ is tetrahydropyran-2,5-diyl, Z$^1$ and Z$^3$ are a single bond and L$^1$ and L$^2$ are fluorine, G is a divalent group represented by formula (pr-2);

when R$^a$ is —C$_5$H$_{11}$, R$^b$ is —OC$_2$H$_5$, a, b and c are 0, Z$^3$ is a single bond and L$^1$ and L$^2$ are fluorine, G is a divalent group represented by formula (pr-2); and when R$^a$ is —CH=CH$_2$ or —C$_2$H$_5$, R$^b$ is —OC$_2$H$_5$, a, b and c are 0, Z$^3$ is a single bond and L$^1$ and L$^2$ are fluorine, G is a divalent group represented by formula (pr-1).

3. The compound according to claim 1, represented by formulas (1-2) or (1-3):

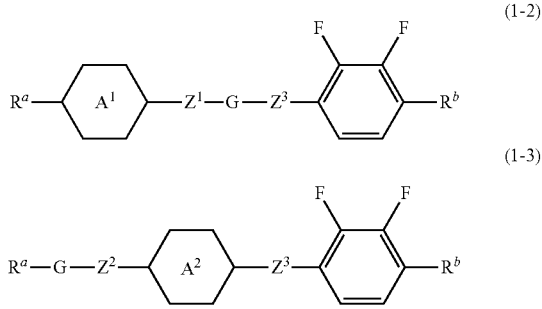

(1-2)

(1-3)

wherein, in formula (1-2) or (1-3),

R$^a$ and R$^b$ are independently hydrogen or alkyl having 1 to 10 carbons, alkoxy having 1 to 9 carbons, alkoxyalkyl having 2 to 9 carbons, alkenyl having 2 to 10 carbons or alkenyloxy having 2 to 9 carbons;

ring A$^1$ and ring A$^2$ are independently 1,4-cyclohexylene, 1,4-cyclohexenylene, 1,4-phenylene, 2-fluoro-1,4-phenylene or 2,3-difluoro-1,4-phenylene;

G is a divalent group represented by formula (pr-1) or (pr-2);

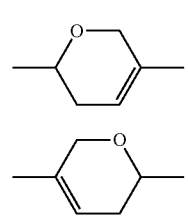

(pr-1)

(pr-2)

wherein,

Z$^1$, Z$^2$ and Z$^3$ are independently a single bond, —COO—, —COO—, —CH$_2$O—, —OCH$_2$— or —CH$_2$CH$_2$—.

4. The compound according to claim 1, represented by any one of formulas (1-2-1) to (1-2-6) and formulas (1-3-1) to (1-3-6):

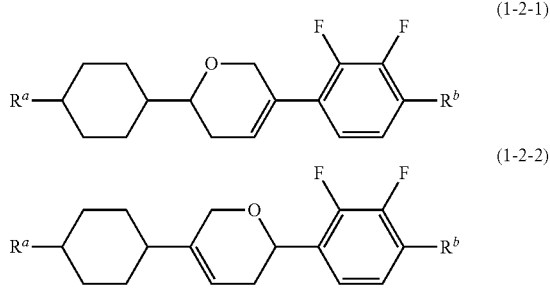

(1-2-1)

(1-2-2)

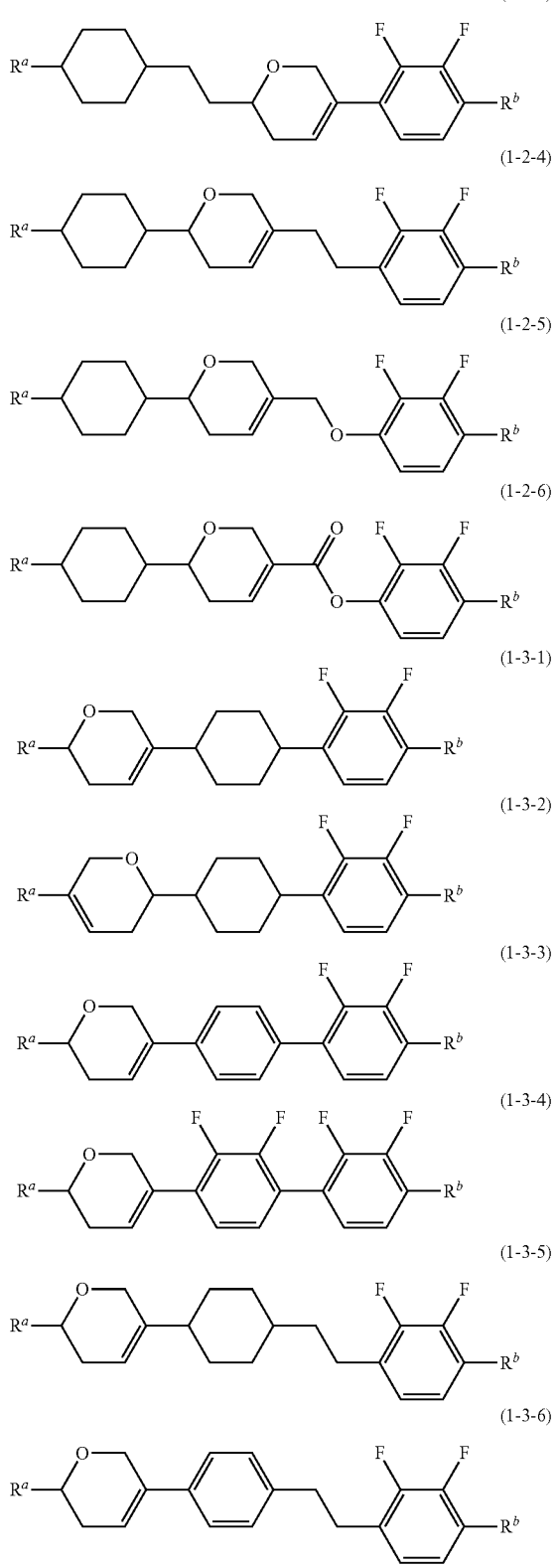

wherein, in formulas (1-2-1) to (1-2-6) and formulas (1-3-1) to (1-3-6),

R$^a$ and R$^b$ are independently hydrogen or alkyl having 1 to 10 carbons, alkoxy having 1 to 9 carbons, alkoxyalkyl having 2 to 9 carbons, alkenyl having 2 to 10 carbons or alkenyloxy having 2 to 9 carbons.

5. The compound according to claim 4, wherein, in formulas (1-2-1) to (1-2-6) and formulas (1-3-1) to (1-3-6) described in claim 4, R$^a$ is alkyl having 1 to 10 carbons, and R$^b$ is alkoxy having carbons 1 to 9.

6. The compound according to claim 1, represented by Formula (1-4):

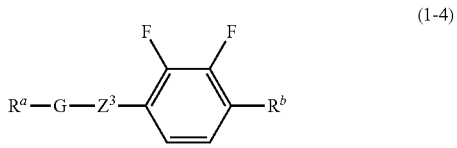

wherein, in formula (1-4),

R$^a$ and R$^b$ are independently hydrogen or alkyl having 1 to 10 carbons, alkoxy having carbons 1 to 9, alkoxyalkyl having 2 to 9 carbons, alkenyl having 2 to 10 carbons or alkenyloxy having carbons 2 to 9;

G is a divalent group represented by formula (pr-1) or (pr-2);

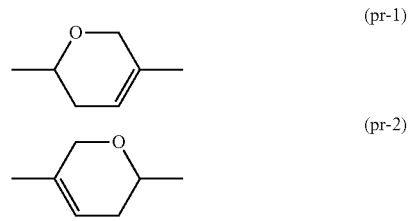

wherein,

Z$^3$ is a single bond, —COO—, —COO—, —CH$_2$O—, —OCH$_2$— or —CH$_2$CH$_2$—;

when R$^a$ is —C$_5$H$_{11}$, R$^b$ is —OC$_2$H$_5$ and Z$^3$ is a single bond, G is a divalent group represented by formula (pr-2); and when R$^a$ is —CH=CH$_2$ or —C$_2$H$_5$, R$^b$ is —OC$_2$H$_5$ and Z$^3$ is a single bond, G is a divalent group represented by formula (pr-1).

7. The compound according to claim 1, represented by any one of formulas (1-4-1) to (1-4-4):

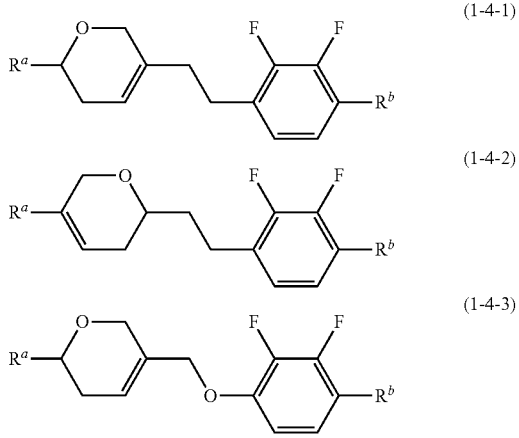

(1-4-4)

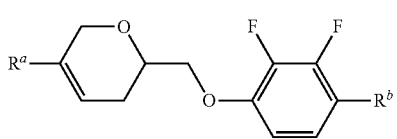

wherein, in formulas (1-4-1) to (1-4-4),
$R^a$ and $R^b$ are independently hydrogen or alkyl having 1 to 10 carbons, alkoxy having carbons 1 to 9, alkoxyalkyl having 2 to 9 carbons, alkenyl having 2 to 10 carbons or alkenyloxy having carbons 2 to 9.

8. The compound according to claim 7, wherein, in formulas (1-4-1) to (1-4-4) described in claim 7, $R^a$ is alkyl having 1 to 10 carbons, and $R^b$ is alkoxy having 1 to 9 carbons.

9. A liquid crystal composition containing at least one compound represented by formula (1) and at least one compound represented by formula (2), (3) or (4)

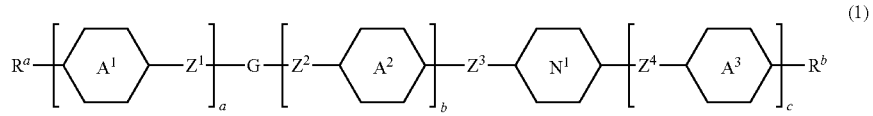

(1)

wherein, in formula (1),
$R^a$ and $R^b$ are independently hydrogen or alkyl having 1 to 10 carbons, and in the alkyl, at least one —CH$_2$— may be replaced by —O—, —S—, —CO— or —SiH$_2$—, at least one —CH$_2$CH$_2$— may be replaced by —CH=CH— or —C≡C—, and in the groups, at least one hydrogen may be replaced by fluorine or chlorine, and $R^b$ may be fluorine, chlorine, —C≡N or —C≡C—C≡N;
ring $A^1$, ring $A^2$ and ring $A^3$ are independently 1,4-cyclohexylene, decahydronaphthalene-2,6-diyl, 1,4-phenylene, and in the groups, at least one —CH$_2$— may be replaced by —O—, —S—, —CO— or —SiH$_2$—, at least one —CH$_2$CH$_2$— may be replaced by —CH=CH— or —CH=N—, and in the divalent groups, at least one hydrogen may be replaced by fluorine, chlorine, —C≡N, —CF$_3$, —CHF$_2$, —CH$_2$F, —OCF$_3$, —OCHF$_2$ or —OCH$_2$F;
ring $N^1$ is 1,4-cyclohexylene, decahydronaphthalene-2,6-diyl, 1,2,3,4-tetrahydronaphthalene-2,6-diyl, 2,6,7-trioxabicyclo[2.2.2]octane-1,4-diyl, 1,4-phenylene, naphthalene-2,6-diyl, 9,10-dihydrophenanthrene-2,7-diyl, 9H-xanthene-2,6-diyl or 9H-fluorene-2,7-diyl, and in the groups, at least one —CH$_2$— may be replaced by —O—, —S—, —CO— or —SiH$_2$—, at least one —CH$_2$CH$_2$— may be replaced by —CH=CH— or —CH=N—, and in the divalent groups, at least one hydrogen may be replaced by fluorine, chlorine, —C≡N; —CF$_3$, —CHF$_2$, —CH$_2$F, —OCF$_3$, —OCHF$_2$ or —OCH$_2$F;
G is a divalent group represented by formula (pr-1) or (pr-2);

(pr-1)

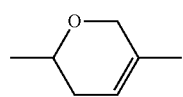

(pr-2)

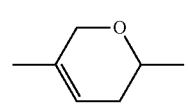

wherein,
$Z^1$ and $Z^2$ are independently a single bond or alkylene having 1 to 6 carbons, and in the alkylene, at least one —CH$_2$— may be replaced by —O—, —S—, —CO— or —SiH$_2$—, one or two pieces of —CH$_2$CH$_2$— may be replaced by —C≡C—, and in the divalent groups, at least one hydrogen may be replaced by fluorine or chlorine;
$Z^3$ and $Z^4$ are independently a single bond or alkylene having 1 to 6 carbons, and in the alkylene, at least one —CH$_2$— may be replaced by —O—, —S—, —CO— or —SiH$_2$—, one or two —CH$_2$CH$_2$— may be replaced by —CH=CH— or —C≡C—, and in the divalent groups, at least one hydrogen may be replaced by fluorine or chlorine; and
a, b and c are independently 0, 1 or 2, and a sum of a, b and c is an integer from 0 to 3; and

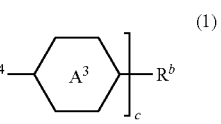

(2)

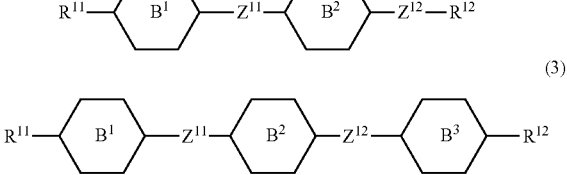

(3)

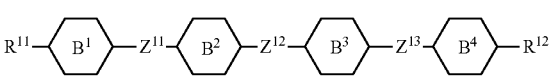

(4)

wherein, in formulas (2) to (4),
$R^{11}$ and $R^{12}$ are independently alkyl having 1 to 10 carbons or alkenyl having 2 to 10 carbons, and in the alkyl and the alkenyl, at least one —CH$_2$— may be replaced by —O—, and in the groups, at least one hydrogen may be replaced by fluorine;
ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl; and
$Z^{11}$, $Z^{12}$ and $Z^{13}$ are independently a single bond, —COO—, —CH$_2$CH$_2$—, —CH=CH— or —C≡C—.

10. The liquid crystal composition according to claim 9, further containing at least one compound selected from the group of compounds represented by formulas (5) to (11):

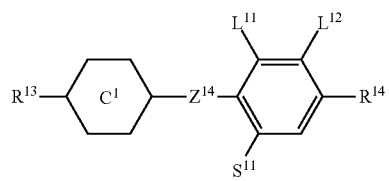
(5)

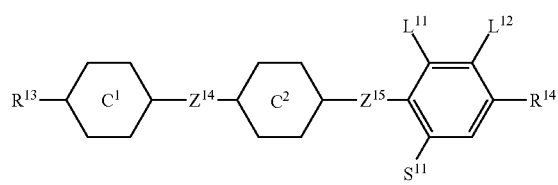
(6)

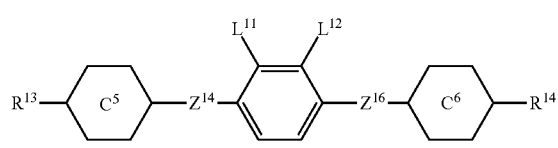
(7)

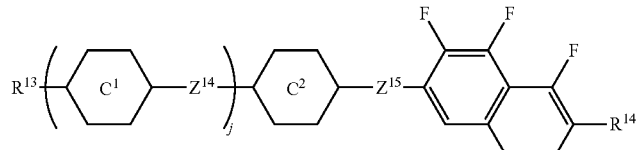
(8)

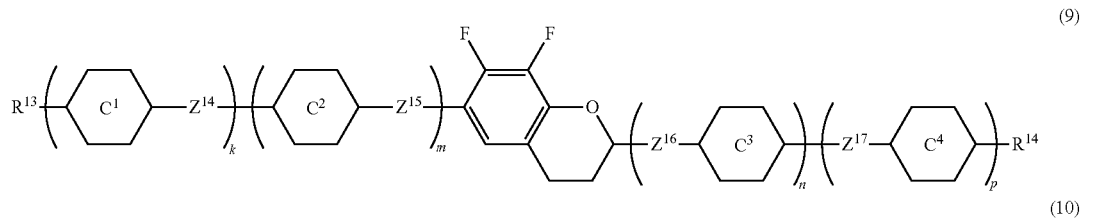
(9)

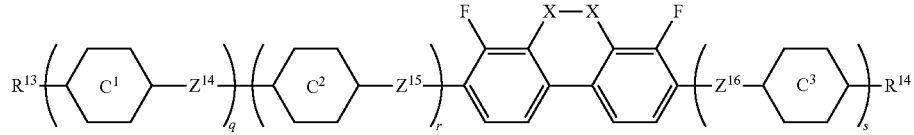
(10)

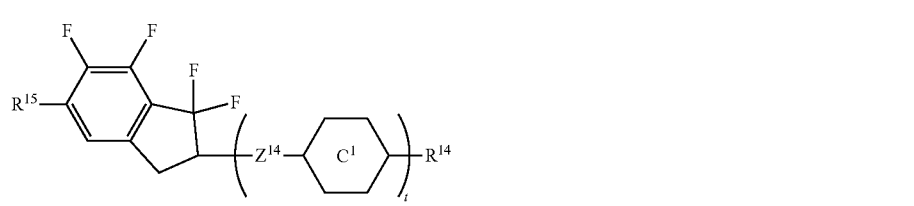
(11)

wherein, in formulas (5) to (11), $R^{13}$, $R^{14}$, and $R^{15}$ are independently alkyl having 1 to 10 carbons or alkenyl having 2 to 10 carbons, and in the alkyl and the alkenyl, at least one —CH$_2$— may be replaced by —O—, and in the groups, at least one hydrogen may be replaced by fluorine and $R^{15}$ may be hydrogen or fluorine;

ring $C^1$, ring $C^2$, ring $C^3$ and ring $C^4$ are independently 1,4-cyclohexylene, 1,4-cyclohexenylene, 1,4-phenylene in which at least one hydrogen may be replaced by fluorine, tetrahydropyran-2,5-diyl or decahydronaphthalene-2,6-diyl;

ring $C^5$ and ring $C^6$ are independently 1,4-cyclohexylene, 1,4-cyclohexenylene, 1,4-phenylene, tetrahydropyran-2,5-diyl or decahydronaphthalene-2,6-diyl;

$Z^{14}$, $Z^{15}$, $Z^{16}$ and $Z^{17}$ are independently a single bond, —COO—, —CH$_2$O—, —OCF$_2$—, —CH$_2$CH$_2$— or —OCF$_2$CH$_2$CH$_2$—;

$L^{11}$ and $L^{12}$ are independently fluorine or chlorine;

$S^{11}$ is hydrogen or methyl;

X is —CHF— or —CF$_2$—; and j, k, m, n, p, q, r and s are independently 0 or 1, a sum of k, m, n and p is 1 or 2, a sum of q, r and s is 0, 1, 2 or 3, and t is 1, 2 or 3.

11. The liquid crystal composition according to claim 9, further containing at least one compound represented by formula (12), (13) or (14);

(12)

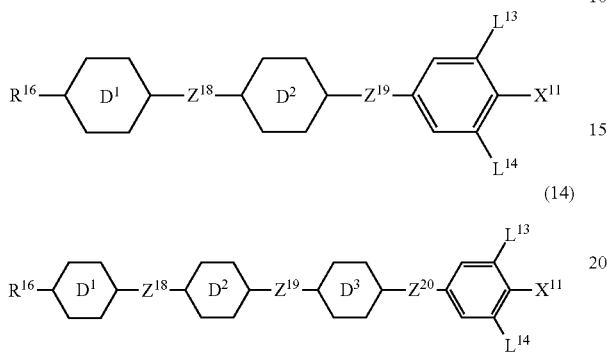

(13)

(14)

wherein, in formulas (12) to (14),
$R^{16}$ is alkyl having 1 to 10 carbons or alkenyl having 2 to 10 carbons, and in the alkyl and the alkenyl, at least one —$CH_2$— may be replaced by —O—, and in the groups, at least one hydrogen may be replaced by fluorine;
$X^{11}$ is fluorine, chlorine, —$CF_3$, —$CHF_2$, —$CH_2F$, —$OCF_3$, —$OCHF_2$, —$OCF_2CHF_2$ or —$OCF_2CHFCF_3$;
ring $D^1$, ring $D^2$ and ring $D^3$ are independently 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;
$Z^{18}$, $Z^{19}$ and $Z^{20}$ are independently a single bond, —COO—, —$CH_2O$—, —$CF_2O$—, —$OCF_2$—, —$CH_2CH_2$—, —CH=CH—, —C≡C— or —$(CH_2)_4$—; and
$L^{13}$ and $L^{14}$ are independently hydrogen or fluorine.

12. The liquid crystal composition according to claim 9, further containing at least one compound represented by formula (15):

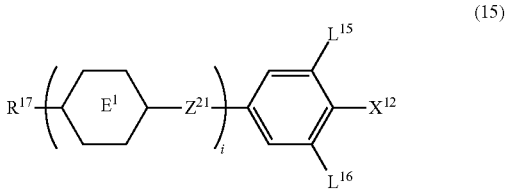

(15)

wherein, in formula (15),
$R^{17}$ is alkyl having 1 to 10 carbons or alkenyl having 2 to 10 carbons, and in the alkyl and the alkenyl, at least one —$CH_2$— may be replaced by —O—, and in the groups, at least one hydrogen may be replaced by fluorine;
$X^{12}$ is —C≡N or —C≡C—C≡N;
ring $E^1$ is 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;
$Z^{21}$ is a single bond, —COO—, —$CH_2O$—, —$CF_2O$—, —$OCF_2$—, —$CH_2CH_2$— or —C≡C—;
$L^{15}$ and $L^{16}$ are independently hydrogen or fluorine; and
i is 1, 2, 3 or 4.

13. A liquid crystal display device comprising the liquid crystal composition according to claim 9.

* * * * *